US009212198B2

(12) United States Patent
Franz et al.

(10) Patent No.: US 9,212,198 B2
(45) Date of Patent: Dec. 15, 2015

(54) METAL COMPLEXES

(75) Inventors: Adam W. Franz, Kelkheim (DE); Rémi Manouk Anémian, Seoul (KR)

(73) Assignee: Merck Patent GmbH, Darmstadt (DE)

( * ) Notice: Subject to any disclaimer, the term of this patent is extended or adjusted under 35 U.S.C. 154(b) by 944 days.

(21) Appl. No.: 13/395,473

(22) PCT Filed: Aug. 18, 2010

(86) PCT No.: PCT/EP2010/005056
§ 371 (c)(1),
(2), (4) Date: Mar. 12, 2012

(87) PCT Pub. No.: WO2011/032626
PCT Pub. Date: Mar. 24, 2011

(65) Prior Publication Data
US 2012/0175561 A1 Jul. 12, 2012

(30) Foreign Application Priority Data

Sep. 16, 2009 (DE) .......................... 10 2009 041 414

(51) Int. Cl.
*C09K 11/06* (2006.01)
*H01L 51/54* (2006.01)
*C07F 15/00* (2006.01)
*H01L 51/00* (2006.01)
*H01L 51/50* (2006.01)

(52) U.S. Cl.
CPC ............. *C07F 15/0033* (2013.01); *C09K 11/06* (2013.01); *H01L 51/0085* (2013.01); *C09K 2211/1029* (2013.01); *C09K 2211/185* (2013.01); *H01L 51/5016* (2013.01); *Y02E 10/549* (2013.01)

(58) Field of Classification Search
CPC ............. C07F 15/0033; C07F 15/0006; C07F 15/006; C07F 15/0073; H01L 51/0084; H01L 51/0085; H01L 51/0087; H01L 51/50; H01L 51/5016; C09K 11/06; C09K 2211/1029–2211/1037; C09K 2211/1044–2211/1051; C09K 2211/185
See application file for complete search history.

(56) References Cited

U.S. PATENT DOCUMENTS

| 2004/0137263 | A1* | 7/2004 | Burn et al. ..................... 428/690 |
| 2005/0247911 | A1* | 11/2005 | Burn et al. .................. 252/301.35 |
| 2006/0127696 | A1 | 6/2006 | Stossel et al. |
| 2006/0220004 | A1* | 10/2006 | Stossel et al. .................. 257/40 |
| 2008/0009627 | A1 | 1/2008 | Tsuboyama et al. |
| 2008/0220265 | A1 | 9/2008 | Xia et al. |
| 2008/0280163 | A1* | 11/2008 | Kwong et al. ................ 428/704 |

FOREIGN PATENT DOCUMENTS

| JP | 2007214175 A | 8/2007 |
| JP | 2008013700 A | 1/2008 |
| TW | 2008-40111 A | 10/2008 |
| WO | WO-2008/140657 A1 | 11/2008 |
| WO | WO-2009/005272 A2 | 1/2009 |
| WO | WO-2009/073245 A1 | 6/2009 |

OTHER PUBLICATIONS

International Search Report for PCT/EP2010/005056 mailed Oct. 21, 2010.
English translation of Japanese Office Action mailed on Oct. 7, 2014 for Patent Application No. 2012-529135.
Taiwan Office Action and IPO Search Report for 099130874 dated Jun. 23, 2014.

* cited by examiner

*Primary Examiner* — Michael H Wilson
(74) *Attorney, Agent, or Firm* — Drinker Biddle & Reath LLP

(57) ABSTRACT

The present invention relates to metal complexes having high solubility and to electronic devices, in particular organic electroluminescent devices, containing these metal complexes.

19 Claims, 1 Drawing Sheet

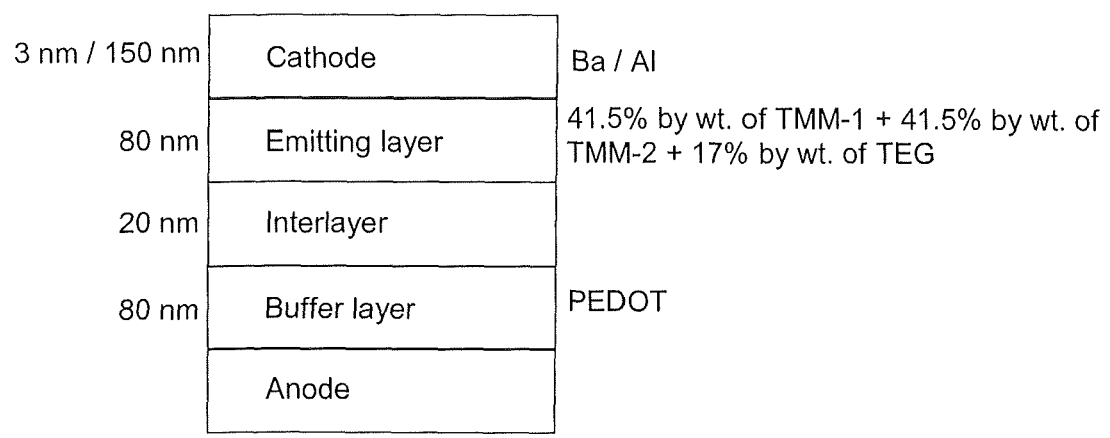

METAL COMPLEXES

CROSS-REFERENCE TO RELATED APPLICATIONS

This application is a national stage application (under 35 U.S.C. §371) of PCT/EP2010/005056, filed Aug. 18, 2010, which claims benefit of German application 10 2009 041 414.2, filed Sep. 16, 2009.

The structure of organic electroluminescent devices (OLEDs) in which organic semiconductors are employed as functional materials is described, for example, in U.S. Pat. No. 4,539,507, U.S. Pat. No. 5,151,629, EP 0676461 and WO 98/27136. The emitting materials employed here are increasingly organometallic complexes which exhibit phosphorescence instead of fluorescence (M. A. Baldo et al., *Appl. Phys. Lett.* 1999, 75, 4-6). For quantum-mechanical reasons, an up to four-fold increase in energy and power efficiency is possible using organometallic compounds as phosphorescence emitters. In general, however, there is still a need for improvement in the case of OLEDs which exhibit triplet emission, in particular with respect to efficiency, operating voltage and lifetime. This applies, in particular, to OLEDs which emit in the relatively short-wave region, i.e. green and blue. Furthermore, many phosphorescent emitters do not have high solubility for processing from solution, meaning that there is also a further need for improvement here.

In accordance with the prior art, the triplet emitters used in phosphorescent OLEDs are, in particular, iridium and platinum complexes, which are usually employed as cyclometallated complexes. The ligands here are frequently derivatives of phenylpyridine. However, the solubility of such complexes is frequently low, which makes processing from solution more difficult or even completely impossible.

The prior art discloses iridium complexes which are substituted by an optionally substituted aryl or heteroaryl group on the phenyl ring of the phenylpyridine ligand in the para-position to the coordination to the metal (WO 2004/026886). Improved solubility of the complexes has thereby been achieved. However, there continues to be a need for improvement here with respect to the solubility and the efficiency and lifetime of the complexes.

SUMMARY OF THE INVENTION

Surprisingly, it has been found that certain metal chelate complexes described in greater detail below have improved solubility and furthermore result in improvements in the organic electroluminescent device, in particular with respect to the efficiency and lifetime. The present invention therefore relates to these metal complexes and to organic electroluminescent devices which contain these complexes.

The invention thus relates to a compound of the formula (1)

$$M(L)_n(L')_m \quad \text{formula (1)}$$

where the compound of the general formula (1) contains a moiety $M(L)_n$ of the formula (2) or formula (3):

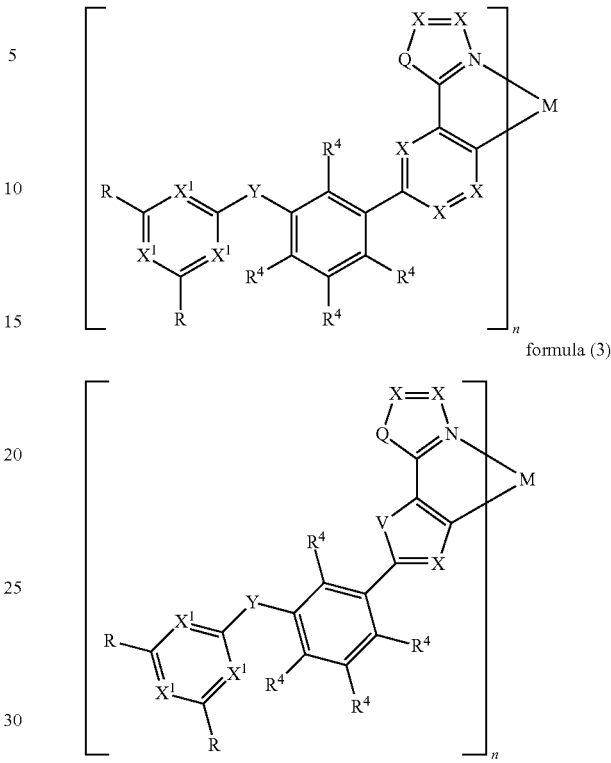

where the following applies to the symbols and indices used:

M is a metal selected from the group consisting of iridium, rhodium, platinum and palladium;

X, $X^1$ are, identically or differently on each occurrence, $CR^1$ or N;

Q is, identically or differently on each occurrence, $R^1C=CR^1$, $R^1C=N$, O, S, Se or $NR^1$;

V is, identically or differently on each occurrence, O, S, Se or $NR^1$;

Y is, identically or differently on each occurrence, a single bond or a divalent group selected from $C(R^1)_2$, $C(=O)$, O, S, SO, $SO_2$, $NR^1$, $PR^1$ or $P(=O)R^1$;

R is, identically or differently on each occurrence, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R^1$, where one or more non-adjacent $CH_2$ groups may be replaced by $R^2C=CR^2$, $C≡C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^1$, or an aryloxy or heteroaryloxy group having 5 to 60 aromatic ring atoms, which may be substituted by one or more radicals $R^1$, or a diarylamino group, diheteroarylamino group or arylheteroarylamino group having 10 to 40 aromatic ring atoms, which may be substituted by one or more radicals $R^1$;

$R^1$ is, identically or differently on each occurrence, H, D, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R^2$, where one or more non-adjacent $CH_2$ groups may be replaced by $R^2C=CR^2$, $C≡C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 60 aromatic ring atoms, which may be substituted by one or more radicals $R^2$, or a diarylamino group, diheteroarylamino group or arylheteroarylamino group having 10 to 40 aromatic ring atoms, which may be substituted by one or more radicals $R^2$, or a combination of two or more of these groups; two or more radicals $R^1$ here may also form a mono- or polycyclic, aliphatic, aromatic and/or benzo-fused ring system with one another;

$R^2$ is, identically or differently on each occurrence, H, D, F, Cl, Br, I, $N(R^3)_2$, CN, $NO_2$, $Si(R^3)_3$, $B(OR^3)_2$, $C(=O)R^3$, $P(=O)(R^3)_2$, $S(=O)R^3$, $S(=O)_2R^3$, $OSO_2R^3$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R^3$, where one or more non-adjacent $CH_2$ groups may be replaced by $R^3C=CR^3$, $C≡C$, $Si(R^3)_2$, $Ge(R^3)_2$, $Sn(R^3)_2$, $C=O$, $C=S$, $C=Se$, $C=NR^3$, $P(=O)(R^3)$, SO, $SO_2$, $NR^3$, O, S or $CONR^3$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^3$, or an aryloxy or heteroaryloxy group having 5 to 60 aromatic ring atoms, which may be substituted by one or more radicals $R^3$, or a diarylamino group, diheteroarylamino group or arylheteroarylamino group having 10 to 40 aromatic ring atoms, which may be substituted by one or more radicals $R^3$, or a combination of two or more of these groups; two or more adjacent radicals $R^2$ here may form a mono- or polycyclic, aliphatic or aromatic ring system with one another;

$R^3$ is, identically or differently on each occurrence, H, D, F or an aliphatic, aromatic and/or heteroaromatic hydrocarbon radical having 1 to 20 C atoms, in which, in addition, one or more H atoms may be replaced by F; two or more substituents $R^3$ here may also form a mono- or polycyclic, aliphatic or aromatic ring system with one another;

$R^4$ is, identically or differently on each occurrence, H or D;

L' is, identically or differently on each occurrence, any desired co-ligand;

n is 1, 2 or 3 when M is iridium or rhodium and is 1 or 2 when M is platinum or palladium;

m is 0, 1, 2, 3 or 4;

it is also possible here for a plurality of ligands L to be linked to one another or for L to be linked to L' via any desired bridge Z and thus to form a tridentate, tetradentate, pentadentate or hexadentate ligand system.

A BRIEF DESCRIPTION OF THE FIGURE

FIG. 1 illustrates the results with solution-processed materials in a device configuration according to the invention.

A DETAILED DESCRIPTION OF THE INVENTION

The indices n and m here are selected so that the coordination number at the metal corresponds to 6 when M is iridium or rhodium and corresponds to 4 when M is platinum or palladium.

An aryl group in the sense of this invention contains 6 to 40 C atoms; a heteroaryl group in the sense of this invention contains 2 to 40 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, etc.

An aromatic ring system in the sense of this invention contains 6 to 60 C atoms in the ring system. A heteroaromatic ring system in the sense of this invention contains 2 to 60 C atoms and at least one heteroatom in the ring system, with the proviso that the sum of C atoms and heteroatoms is at least 5. The heteroatoms are preferably selected from N, 0 and/or S. For the purposes of this invention, an aromatic or heteroaromatic ring system is intended to be taken to mean a system which does not necessarily contain only aryl or heteroaryl groups, but instead in which, in addition, a plurality of aryl or heteroaryl groups may be interrupted by a non-aromatic unit (preferably less than 10% of the atoms other than H), such as, for example, an $sp^3$-hybridised C, N or O atom or a carbonyl group. Thus, for example, systems such as 9,9'-spirobifluorene, 9,9-diarylfluorene, triarylamine, diaryl ether, stilbene, etc., are also intended to be taken to mean aromatic ring systems for the purposes of this invention, and likewise systems in which two or more aryl groups are interrupted, for example, by a linear or cyclic alkyl group or by a silyl group.

A cyclic alkyl, alkoxy or thioalkoxy group in the sense of this invention is taken to mean a monocyclic, bicyclic or polycyclic group.

For the purposes of the present invention, a $C_1$- to $C_{40}$-alkyl group, in which, in addition, individual H atoms or $CH_2$ groups may be substituted by the above-mentioned groups, is taken to mean, for example, the radicals methyl, ethyl, n-propyl, i-propyl, n-butyl, i-butyl, s-butyl, t-butyl, 2-methyl-butyl, n-pentyl, s-pentyl, tert-pentyl, 2-pentyl, neopentyl, cyclopentyl, n-hexyl, s-hexyl, tert-hexyl, 2-hexyl, 3-hexyl, neohexyl, cyclohexyl, 2-methyl-pentyl, n-heptyl, 2-heptyl, 3-heptyl, 4-heptyl, cycloheptyl, 1-methylcyclo-hexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, trifluoromethyl, pentafluoroethyl or 2,2,2-trifluoroethyl. An alkenyl group is taken to mean, for example, ethenyl, propenyl, butenyl, pentenyl, cyclopentenyl, hexenyl, cyclohexenyl, heptenyl, cycloheptenyl, octenyl, cyclooctenyl or cyclocta-dienyl. An alkynyl group is taken to mean, for example, ethynyl, propynyl, butynyl, pentynyl, hexynyl, heptynyl or octynyl. A $C_1$- to $C_{40}$-alkoxy group is taken to mean, for example, methoxy, trifluoromethoxy, ethoxy, n-propoxy, i-propoxy, n-butoxy, i-butoxy, s-butoxy, t-butoxy or 2-methylbutoxy. An aromatic or heteroaromatic ring system having 5-60 aromatic ring atoms, which may also in each case be substituted by the radicals R mentioned above and may be linked to the aromatic or heteroaromatic ring system via any desired positions, is taken to mean, for example, groups derived from benzene, naphthalene, anthracene, benzanthracene, phenanthrene, benzophenanthrene, pyrene, chrysene, perylene, fluoranthene, benzo-fluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

If two adjacent radicals $R^1$ and $R^2$ form a ring system with one another, the ring systems formed are aliphatic or aromatic rings which are condensed onto the ligand. Examples of ring systems of this type are condensed-on cyclohexyl groups or condensed-on phenyl groups. It is also possible for radicals which are bonded to the two different aromatic rings of the ligand, i.e., for example, to the phenyl group and the pyridine group, to form a ring with one another, which can result, for example, in azafluorene structures or phenanthridine structures. It is furthermore possible, for example, if Q stands for $CR^1$=$CR^1$, for these radicals to form an aromatic ring with one another, overall forming, for example, an isoquinoline structure.

Preference is given to compounds of the formula (1), characterised in that they are uncharged, i.e. are electrically neutral. This is achieved in a simple manner through the charge of the ligands L and L' being selected so that they compensate for the charge of the complexed metal atom M.

Preference is furthermore given to compounds of the formula (1), characterised in that the sum of the valence electrons around the metal atom is 16 for platinum and palladium and 18 for iridium or rhodium. This preference is due to the particular stability of these metal complexes.

In a preferred embodiment of the invention, M stands for iridium or platinum. M particularly preferably stands for iridium.

If M stands for platinum or palladium, the index n stands for 1 or 2. If the index n=1, one bidentate or two monodentate ligands L', preferably one bidentate ligand L', are coordinated to the metal M. Correspondingly, the index m=1 for one bidentate ligand U and the index m=2 for two monodentate ligands L'. If the index n=2, the index m=0.

If M stands for iridium or rhodium, the index n stands for 1, 2 or 3, preferably for 2 or 3. If the index n=1, four monodentate or two bidentate or one bidentate and two monodentate or one tridentate and one monodentate or one tetradentate ligand L', preferably two bidentate ligands L', are coordinated to the metal. Correspondingly, the index m is equal to 1, 2, 3 or 4, depending on the ligand L'. If the index n=2, one bidentate or two monodentate ligands L', preferably one bidentate ligand L', are coordinated to the metal. Correspondingly, the index m is equal to 1 or 2, depending on the ligand L'. If the index n=3, the index m=0.

In a preferred embodiment of the invention, the symbol X stands, identically or differently on each occurrence, for $CR^1$.

In a further preferred embodiment of the invention, either all symbols $X^1$ stand, identically or differently on each occurrence, for $CR^1$, or all symbols $X^1$ stand for N.

In a further preferred embodiment of the invention, the symbol Q stands, identically or differently on each occurrence, for $R^1C$=$CR^1$ or $R^1C$=N, particularly preferably for $R^1C$=$CR^1$.

In a further preferred embodiment of the invention, the symbol V stands, identically or differently on each occurrence, for O, S or $NR^1$, particularly preferably for S.

In a further preferred embodiment of the invention, the symbol Y stands, identically or differently on each occurrence, for a single bond or a divalent group selected from C(=O) or $NR^1$, particularly preferably for a single bond.

In a further preferred embodiment of the invention, $R^4$ is equal to H.

It is particularly preferred for the above-mentioned preferences to apply simultaneously. In a particularly preferred embodiment of the invention, the following therefore applies to the symbols used:

M is iridium or platinum, particularly preferably iridium;

X is, identically or differently on each occurrence, $CR^1$;

$X^1$ is selected so that all $X^1$ stand, identically or differently on each occurrence, for $CR^1$ or that all symbols $X^1$ stand for N;

Q is, identically or differently on each occurrence, $R^1C$=$CR^1$ or $R^1C$=N, preferably $R^1C$=$CR^1$;

V is, identically or differently on each occurrence, O, S or $NR^1$, preferably S;

Y is, identically or differently on each occurrence, a single bond or a divalent group selected from C(=O) or $NR^1$, preferably a single bond;

$R^4$ is H.

In a particularly preferred embodiment of the invention, the moieties of the formula (2) or (3) are therefore selected from the moieties of the following formulae (4), (5), (6) and (7):

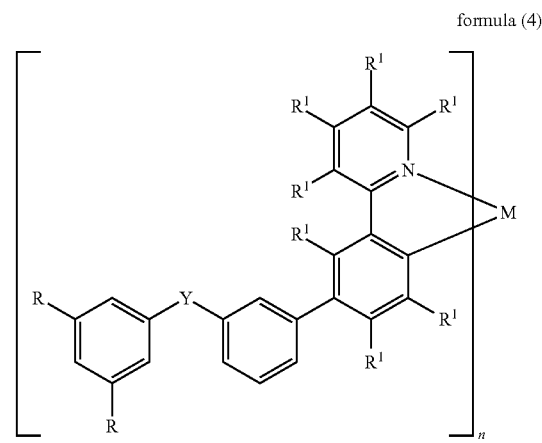

formula (4)

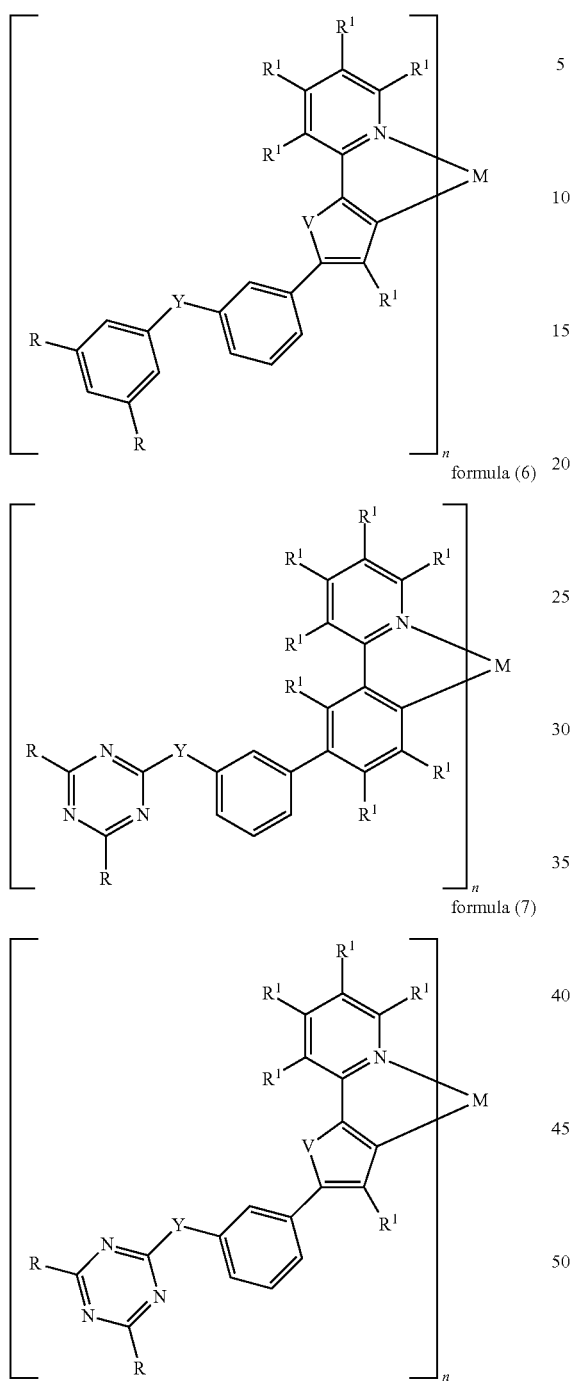

formula (5)

formula (6)

formula (7)

where the symbols and indices used have the meanings given above, in particular the preferred meanings given above.

As already mentioned above, adjacent radicals $R^1$ here may also form a ring with one another. Thus, for example, quinoline or isoquinoline structures, which may be substituted by one or more radicals $R^2$, are accessible from the pyridine rings.

In a preferred embodiment of the invention, the symbol R stands, identically or differently on each occurrence, for a straight-chain alkyl group having 1 to 10 C atoms or for a branched or cyclic alkyl group having 3 to 10 C atoms, each of which may be substituted by one or more radicals $R^1$, and where one or more non-adjacent $CH_2$ groups may be replaced by O and where one or more H atoms may be replaced by D, F or CN, or an aromatic or heteroaromatic ring system having 5 to 30 aromatic ring atoms, which may in each case be substituted by one or more radicals $R^1$. In a particularly preferred embodiment of the invention, the symbol R stands, identically or differently on each occurrence, for an aromatic or heteroaromatic ring system having 5 to 20 aromatic ring atoms, which may in each case be substituted by one or more radicals $R^1$. The group R is very particularly preferably selected from the groups of the following formulae (8) to (24):

formula (8)

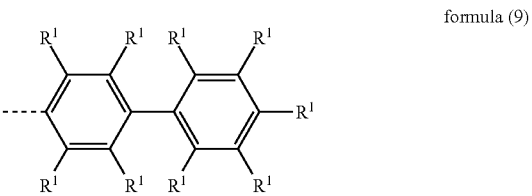

formula (9)

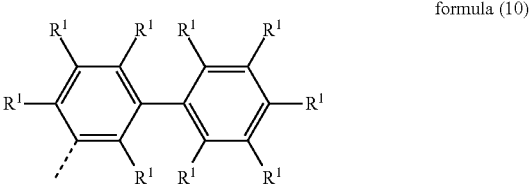

formula (10)

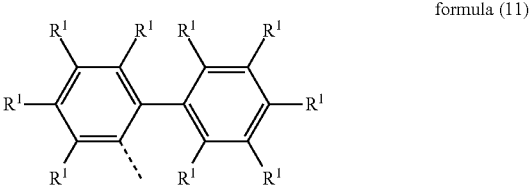

formula (11)

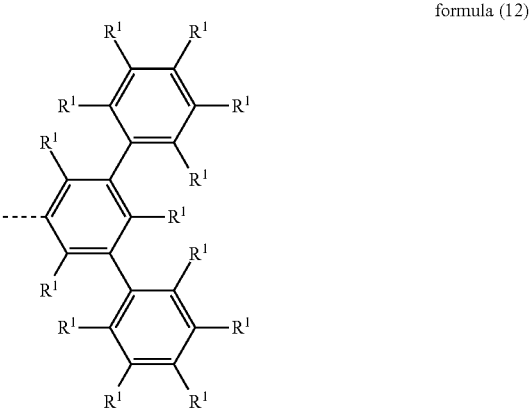

formula (12)

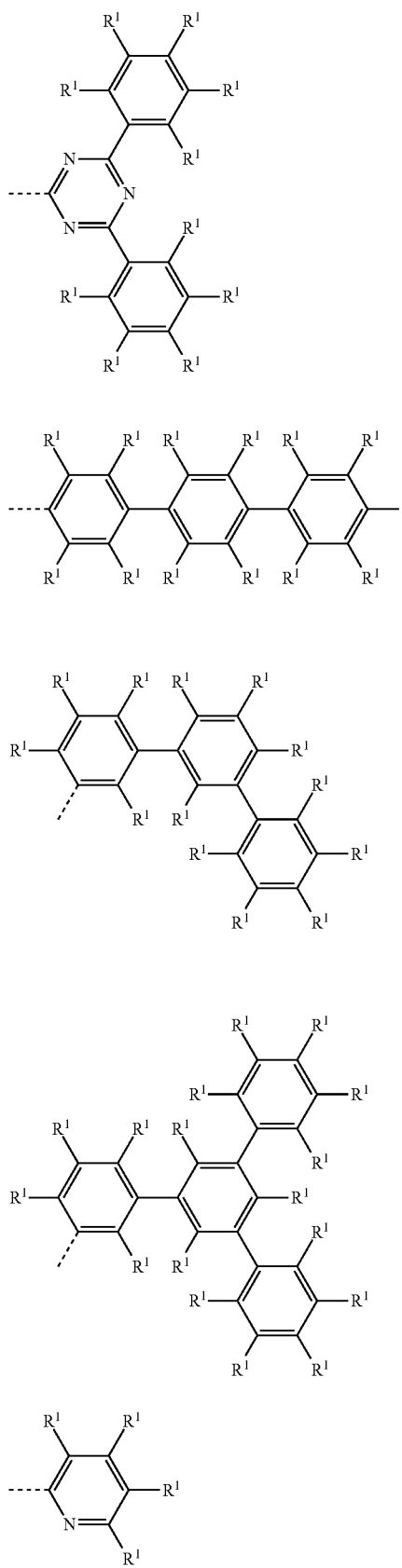
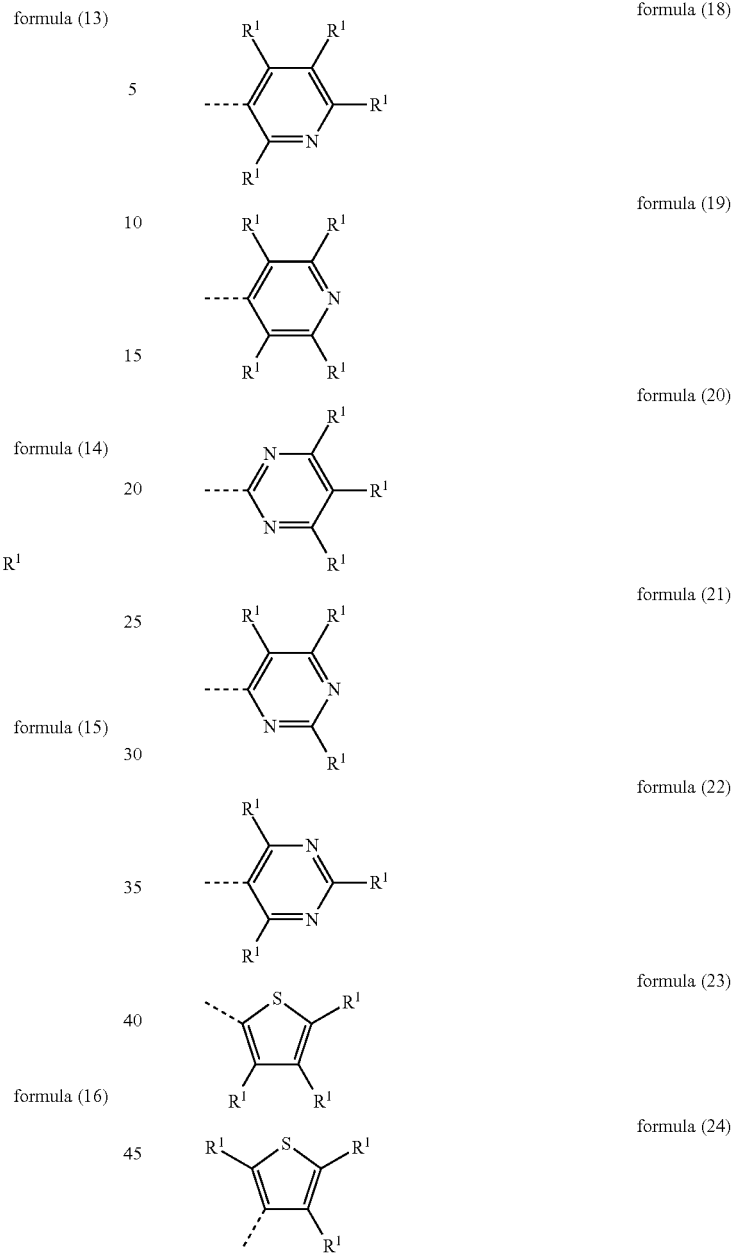

where the symbols used have the meanings given above, and the dashed bond indicates the position via which this group is bonded.

In a preferred embodiment of the compounds according to the invention, one of the radicals $R^1$, either in the compounds of the formulae (4) to (7) or in the groups R of the formulae (8) to (24), stands for a styryl group or for a terminal alkenyl group. Groups of this type are suitable for crosslinking of the compounds according to the invention in the layer. Crosslinking of this type may be appropriate in order to be able to produce multilayered devices from solution.

As described above, a bridging unit Z which links this ligand L to one or more further ligands L or L' may also be present instead of one of the radicals $R^1$. In a preferred embodiment of the invention, a bridging unit Z is present instead of one of the radicals $R^1$, so that the ligands have a tridentate or polydentate or polypodal character. It is also possible for two bridging units Z of this type to be present. This results in the formation of macrocyclic ligands or in the formation of cryptates.

Preferred structures having polydentate ligands are the metal complexes of the following formulae (25) to (28):

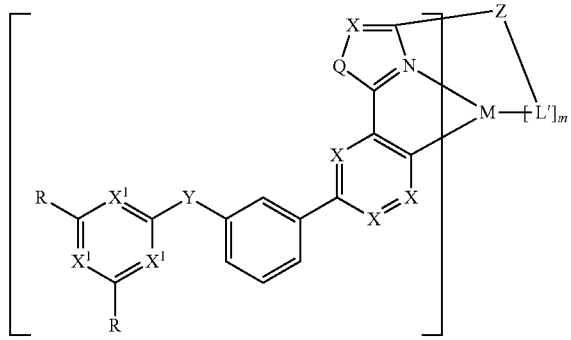

formula (25)

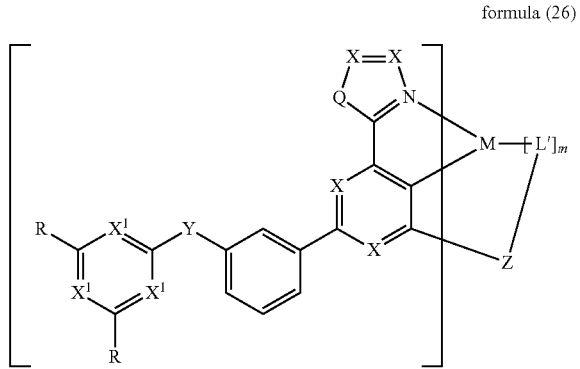

formula (26)

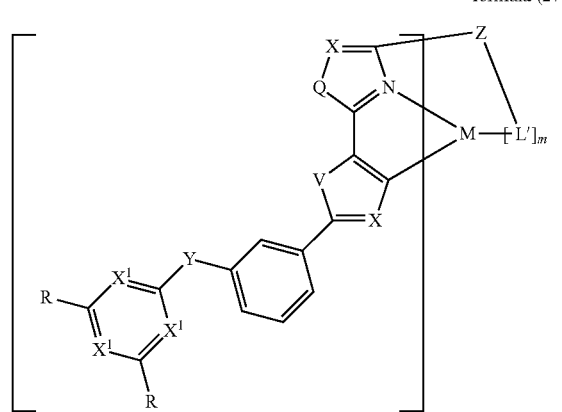

formula (27)

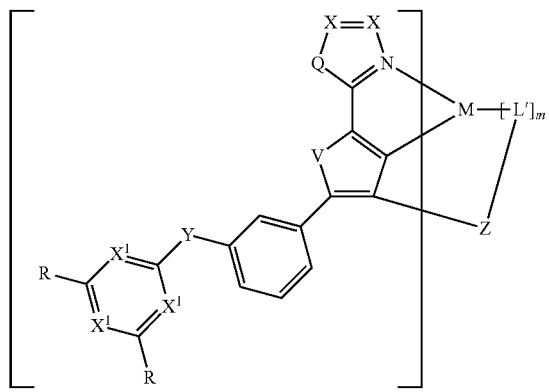

formula (28)

where the symbols used have the meanings given above, and Z preferably represents a bridging unit containing 1 to 80 atoms from the third, fourth, fifth and/or sixth main group (IUPAC group 13, 14, 15 or 16) or a 3- to 6-membered homo- or heterocycle which covalently bonds the part-ligands L to one another or L to L'. The bridging unit V here may also have an asymmetrical structure, i.e. the linking of Z to L or L' need not be identical. The bridging unit Z may be neutral, singly, doubly or triply negatively charged or singly, doubly or triply positively charged. Z is preferably neutral or singly negatively charged or singly positively charged. The charge of Z is preferably selected here in such a way that overall a neutral complex is formed.

The precise structure and chemical composition of the group Z do not have a significant influence on the electronic properties of the complex since the main job of this group is to increase the chemical and thermal stability of the complexes through the bridging of L to one another or to L'.

If Z is a trivalent group, i.e. bridges three ligands L to one another or two ligands L to L' or one ligand L to two ligands L', Z is preferably selected, identically or differently on each occurrence, from the group consisting of B, $B(R^2)^-$, $B(C(R^2)_2)_3$, $(R^2)B(C(R^2)_2)_3^-$, $B(O)_3$, $(R^2)B(O)_3^-$, $B(C(R^2)_2C(R^2)_2)_3$, $(R^2)B(C(R^2)_2C(R^2)_2)_3^-$, $B(C(R^2)_2O)_3$, $(R^2)B(C(R^2)_2 O)_3^-$, $B(OC(R^2)_2)_3$, $(R^2)B(OC(R^2)_2)_3^-$, $C(R^2)$, $CO^-$, $CN(R^2)_2$, $(R^2)C(C(R^2)_2)_3$, $(R^2)C(O)_3$, $(R^2)C(C(R^2)_2C(R^2)_2)_3$, $(R^2)C(C(R^2)_2O)_3$, $(R^2)C(OC(R^2)_2)_3$, $(R^2)C(Si(R^2)_2)_3$, $(R^2)C(Si(R^2)_2C(R^2)_2)_3$, $(R^2)C(C(R^2)_2Si(R^2)_2)_3$, $(R^2)C(Si(R^2)_2Si(R^2)_2)_3$, $Si(R^2)$, $(R^2)Si(C(R^2)_2)_3$, $(R^2)Si(O)_3$, $(R^2)Si(C(R^2)_2C(R^2)_2)_3$, $(R^2)Si(OC(R^2)_2)_3$, $(R^2)Si(C(R^2)_2O)_3$, $(R^2)Si(Si(R^2)_2)_3$, $(R^2)Si(Si(R^2)_2C(R^2)_2)_3$, $(R^2)Si(C(R^2)_2Si(R^2)_2)_3$, $(R^2)Si(Si(R^2)_2Si(R^2)_2)_3$, N, NO, $N(R^2)^+$, $N(C(R^2)_2)_3$, $(R^2)N(C(R^2)_2)_3^+$, $N(C=O)_3$, $N(C(R^2)_2C(R^2)_2)_3$, $(R^2)N(C(R^2)_2C(R^2)_2)^+$, P, $P(R^2)^+$, PO, PS, PSe, PTe, $P(O)_3$, $PO(O)_3$, $P(OC(R^2)_2)_3$, $PO(OC(R^2)_2)_3$, $P(C(R^2)_2)_3$, $P(R^2)(C(R^2)_2)_3^+$, $PO(C(R^2)_2)_3$, $P(C(R^2)_2C(R^2)_2)_3$, $P(R^2)(C(R^2)_2C(R^2)_2)_3^+$, $PO(C(R^2)_2C(R^2)_2)_3$, $S^+$, $S(C(R^2)_2)_3^+$, $S(C(R^2)_2C(R^2)_2)_3^+$, or a unit of the formula (29), (30), (31) or (32):

formula (29)

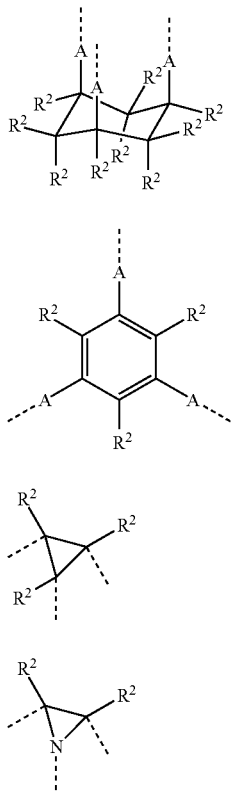

formula (30)

formula (31)

formula (32)

where the dashed bonds each indicate the bond to the part-ligands L or L', and A is selected, identically or differently on each occurrence, from the group consisting of a single bond, O, S, S(=O), S(=O)$_2$, NR$^2$, PR$^2$, P(=O)R$^2$, P(=NR$^2$), C(R$^2$)$_2$, C(=O), C(=NR$^2$), C(=C(R$^2$)$_2$), Si(R$^2$)$_2$ or BR$^2$. The other symbols used have the meanings given above.

If Z is a divalent group, i.e. bridges two ligands L to one another or one ligand L to L', Z is preferably selected, identically or differently on each occurrence, from the group consisting of BR$^2$, B(R$^2$)$_2^-$, C(R$^2$)$_2$, C(=O), Si(R$^2$)$_2$, NR$^2$, PR$^2$, P(R$^2$)$_2^+$, P(=O)(R$^2$), P(=S)(R$^2$), AsR$^2$, As(=O)(R$^2$), As(=S)(R$^2$), O, S, Se, or a unit of the formulae (33) to (41):

formula (33)

formula (34)

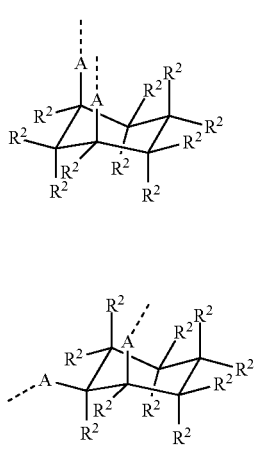

formula (35)

formula (36)

formula (37)

formula (38)

formula (39)

formula (40)

formula (41)

where the dashed bonds each indicate the bond to the part-ligands L or L', and the other symbols used each have the meanings indicated above.

Preferred ligands L' as occur in formula (1) are described below. The ligand groups L' may also be selected correspondingly if they are bonded to L via a bridging unit Z.

The ligands L' are preferably neutral, monoanionic, dianionic or trianionic ligands, particularly preferably neutral or monoanionic ligands. They may be monodentate, bidentate, tridentate or tetradentate and are preferably bidentate, i.e. preferably have two coordination sites. As described above, the ligands L' may also be bonded to L via a bridging group Z.

Preferred neutral, monodentate ligands L' are selected from carbon monoxide, nitrogen monoxide, alkyl cyanides, such as, for example, acetonitrile, aryl cyanides, such as, for example, benzonitrile, alkyl isocyanides, such as, for example, methyl isonitrile, aryl isocyanides, such as, for example, benzoisonitrile, amines, such as, for example, trimethylamine, triethylamine, morpholine, phosphines, in particular halophosphines, trialkylphosphines, triarylphosphines or alkylarylphosphines, such as, for example, trifluorophosphine, trimethylphosphine, tricyclohexylphosphine, tri-tert-butylphosphine, triphenylphosphine, tris(pentafluorophenyl)phosphine, phosphites, such as, for example, trimethyl phosphite, triethyl phosphite, arsines, such as, for example, trifluoroarsine, trimethylarsine, tricyclohexylarsine, tri-tert-butylarsine, triphenylarsine, tris(pentafluorophenyl)arsine, stibines, such as, for example, trifluorostibine, trimethylstibine, tricyclohexylstibine, tri-tert-butylstibine, triphenylstibine, tris(pentafluorophenyl)stibine, nitrogen-containing heterocycles, such as, for example, pyridine, pyridazine, pyrazine, pyrimidine, triazine, and carbenes, in particular Arduengo carbenes.

Preferred monoanionic, monodentate ligands L' are selected from hydride, deuteride, the halides F$^-$, Cl$^-$, Br$^-$ and I$^-$, alkylacetylides, such as, for example, methyl-C≡C$^-$, tert-butyl-C≡C$^-$, arylacetylides, such as, for example, phenyl-C≡C$^-$, cyanide, cyanate, isocyanate, thiocyanate, isothiocyanate, aliphatic or aromatic alcoholates, such as, for example, methanolate, ethanolate, propanolate, isopropanolate, tert-butylate, phenolate, aliphatic or aromatic thioalcoholates, such as, for example, methanethiolate, ethanethiolate, propanethiolate, isopropanethiolate, tert-butanethiolate, thiophenolate, amides, such as, for example, dimethylamide, diethylamide, diisopropylamide, morpholide, carboxylates, such as, for example, acetate, trifluoroacetate, propionate, benzoate, aryl groups, such as, for example, phenyl, naphthyl, and anionic, nitrogen-containing heterocycles, such as pyrrolide, imidazolide, pyrazolide. The alkyl groups in these groups are preferably $C_1$-$C_{20}$-alkyl groups, particularly preferably $C_1$-$C_{10}$-alkyl groups, very particularly preferably $C_1$-$C_4$-alkyl groups. Aryl groups are also taken to mean heteroaryl groups. These groups are as defined above.

Preferred di- or trianionic ligands are O$^{2-}$, S$^{2-}$, carbides, which result in coordination in the form R—C≡M, and nitrenes, which result in coordination in the form R—N=M, where R generally stands for a substituent, or N$^{3-}$.

Preferred neutral or mono- or dianionic, bidentate or polydentate ligands L' are selected from diamines, such as, for example, ethylenediamine, N,N,N',N'-tetramethylethylenediamine, propylenediamine, N,N,N',N'-tetra-methylpropylenediamine, cis- or trans-diaminocyclohexane, cis- or trans-N,N,N',N'-tetramethyldiaminocyclohexane, imines, such as, for example, 2-[(1-(phenylimino)ethyl]pyridine, 2-[(1-(2-methylphenylimino)ethyl]pyridine, 2-[(1-(2,6-diisopropylphenylimino)ethyl]pyridine, 2-[(1-(methylimino)ethyl]-pyridine, 2-[(1-(ethylimino)ethyl]pyridine, 2-[(1-(isopropylimino)ethyl]pyridine, 2-[(1-(tert-butylimino) ethyl]pyridine, diimines, such as, for example, 1,2-bis(methylimino)ethane, 1,2-bis(ethylimino)ethane, 1,2-bis(isopropylimino)ethane, 1,2-bis(tert-butylimino)ethane, 2,3-bis(methylimino)butane, 2,3-bis(ethylimino)butane, 2,3-bis(isopropylimino)butane, 2,3-bis(tert-butylimino)butane, 1,2-bis(phenylimino)ethane, 1,2-bis(2-methylphenylimino) ethane, 1,2-bis(2,6-diisopropylphenylimino)ethane, 1,2-bis(2,6-di-tert-butylphenylimino)ethane, 2,3-bis(phenylimino) butane, 2,3-bis(2-methylphenylimino)butane, 2,3-bis(2,6-diisopropylphenylimino)butane, 2,3-bis(2,6-di-tert-butylphenylimino)butane, heterocycles containing two nitrogen atoms, such as, for example, 2,2'-bipyridine, o-phenanthroline, diphosphines, such as, for example, bis-diphenylphosphinomethane, bisdiphenylphosphinoethane, bis(diphenylphosphino)propane, bis-(diphenylphosphino) butane, bis(dimethylphosphino)methane, bis(dimethylphosphino)ethane, bis(dimethylphosphino)propane, bis(diethylphosphino)methane, bis(diethylphosphino)ethane, bis (diethylphosphino)propane, bis(di-tert-butylphosphino) methane, bis(di-tert-butylphosphino)ethane, bis(tert-butylphosphino)propane, 1,3-diketonates derived from 1,3-diketones, such as, for example, acetylacetone, benzoylacetone, 1,5-diphenylacetylacetone, dibenzoylmethane, bis(1,1,1-trifluoroacetyl)methane, 3-ketonates derived from 3-ketoesters, such as, for example, ethyl acetoacetate, carboxylates derived from aminocarboxylic acids, such as, for example, pyridine-2-carboxylic acid, quinoline-2-carboxylic acid, glycine, N,N-dimethylglycine, alanine, N,N-dimethylaminoalanine, salicyliminates derived from salicylimines, such as, for example, methylsalicylimine, ethylsalicylimine, phenylsalicylimine, dialcoholates derived from dialcohols, such as, for example, ethylene glycol, 1,3-propylene glycol, and dithiolates derived from dithiols, such as, for example, 1,2-ethylenedithiol, 1,3-propylenedithiol.

Preferred tridentate ligands are borates of nitrogen-containing heterocycles, such as, for example, tetrakis(1-imidazolyl)borate and tetrakis(1-pyrazolyl)borate.

Particular preference is furthermore given to bidentate monoanionic ligands L' which form, with the metal, a cyclometallated five-membered or six-membered ring having at least one metal-carbon bond, in particular a cyclometallated five-membered ring. These are, in particular, ligands as generally used in the area of phosphorescent metal complexes for organic electroluminescent devices, i.e. ligands of the phenylpyridine, naphthylpyridine, phenylquinoline, phenylisoquinoline, etc., type, each of which may be substituted by one or more radicals R$^1$. A multiplicity of ligands of this type is known to the person skilled in the art in the area of phosphorescent electroluminescent devices, and he will be able to select further ligands of this type, without inventive step, as ligand L' for compounds of the formula (1). In general, the combination of two groups, as represented by the following formulae (42) to (69), is particularly suitable for this purpose, where one group is bonded via a neutral nitrogen atom or a carbene atom and the other group is bonded via a negatively charged carbon atom or a negatively charged nitrogen atom. The ligand L' can then be formed from the groups of the formulae (42) to (69) by these groups bonding to one another, in each case at the position denoted by #. The position at which the groups coordinate to the metal is denoted by *. These groups may also be bonded to the ligand L via one or two bridging units Z.

formula (42)

formula (43)

-continued
formula (44)
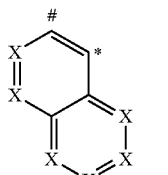
formula (45)
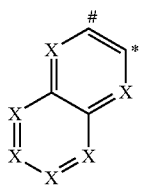
formula (46)
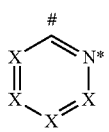
formula (47)
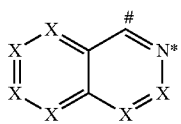
formula (48)
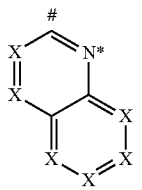
formula (49)
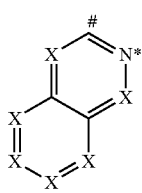
formula (50)
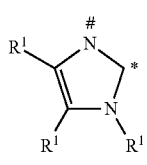
formula (51)
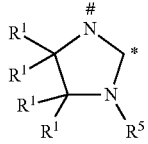
formula (52)
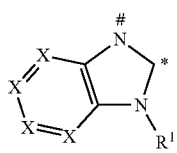
formula (53)
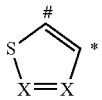
formula (54)
formula (55)
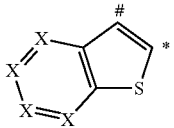
formula (56)
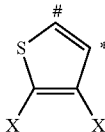
formula (57)
formula (58)
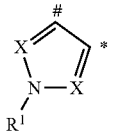
formula (59)
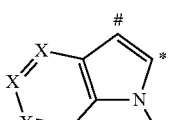
formula (60)
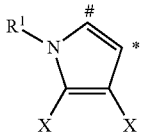
formula (61)
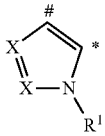
formula (62)
formula (63)

-continued

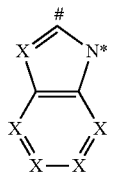
formula (64)

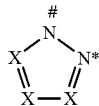
formula (65)

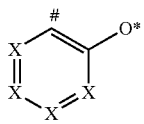
formula (66)

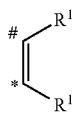
formula (67)

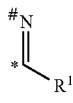
formula (68)

formula (69)

The symbols used here have the same meaning as described above, and preferably a maximum of three symbols X in each group stand for N, particularly preferably a maximum of two symbols X in each group stand for N, very particularly preferably a maximum of one symbol X in each group stands for N. Especially preferably, all symbols X stand, identically or differently on each occurrence, for $CR^1$.

Likewise preferred ligands L' are $\eta^5$-cyclopentadienyl, $\eta^5$-pentamethylcyclopentadienyl, $\eta^6$-benzene or $\eta^7$-cycloheptatrienyl, each of which may be substituted by one or more radicals $R^1$.

Likewise preferred ligands L' are 1,3,5-cis-cyclohexane derivatives, in particular of the formula (70), 1,1,1-tri(methylene)methane derivatives, in particular of the formula (71), and 1,1,1-trisubstituted methanes, in particular of the formulae (72) and (73):

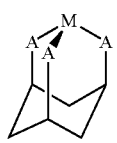
formula (70)

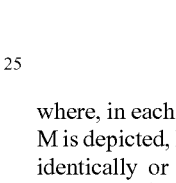
formula (71)

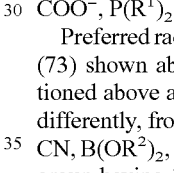
formula (72)

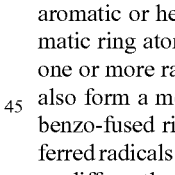
formula (73)

where, in each of the formulae, the coordination to the metal M is depicted, $R^1$ has the meaning given above, and A stands, identically or differently on each occurrence, for $O^-$, $S^-$, $COO^-$, $P(R^1)_2$ or $N(R^1)_2$.

Preferred radicals $R^1$ in the structures of the formulae (2) to (73) shown above and in the preferred embodiments mentioned above are selected on each occurrence, identically or differently, from the group consisting of H, D, F, Br, $N(R^2)_2$, CN, $B(OR^2)_2$, $C(=O)R^2$, $P(=O)(R^2)_2$, a straight-chain alkyl group having 1 to 10 C atoms or a straight-chain alkenyl or alkynyl group having 2 to 10 C atoms or a branched or cyclic alkyl, alkenyl or alkynyl group having 3 to 10 C atoms, each of which may be substituted by one or more radicals $R^2$, where one or more H atoms may be replaced by F, or an aromatic or heteroaromatic ring system having 5 to 14 aromatic ring atoms, which may in each case be substituted by one or more radicals $R^2$; a plurality of radicals $R^1$ here may also form a mono- or polycyclic, aliphatic, aromatic and/or benzo-fused ring system with one another. Particularly preferred radicals $R^1$ are selected on each occurrence, identically or differently, from the group consisting of H, F, Br, CN, $B(OR^2)_2$, a straight-chain alkyl group having 1 to 6 C atoms, in particular methyl, or a branched or cyclic alkyl group having 3 to 10 C atoms, in particular isopropyl or tertbutyl, where one or more H atoms may be replaced by F, or an aromatic or heteroaromatic ring system having 5 to 12 aromatic ring atoms, which may in each case be substituted by one or more radicals $R^2$; a plurality of radicals $R^1$ here may also form a mono- or polycyclic, aliphatic, aromatic and/or benzo-fused ring system with one another.

The metal complexes according to the invention can in principle be prepared by various processes. However, the processes described below have proven particularly suitable.

The present invention therefore furthermore relates to a process for the preparation of the metal-complex compounds of the formula (1) by reaction of the corresponding free ligands with metal alkoxides of the formula (74), with metal ketoketonates of the formula (75), with metal halides of the formula (76) or with dimeric metal complexes of the formula (77):

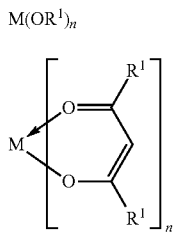  formula (74)

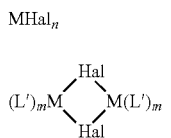  formula (75)

MHal$_n$  formula (76)

$(L')_m M \genfrac{}{}{0pt}{}{\text{Hal}}{\text{Hal}} M(L')_m$  formula (77)

where the symbols M, m, n and R$^1$ have the meanings indicated above, and Hal=F, Cl, Br or I.

It is likewise possible to use metal compounds, in particular iridium compounds, which carry both alcoholate and/or halide and/or hydroxyl radicals as well as ketoketonate radicals. These compounds may also be charged. Corresponding iridium compounds which are particularly suitable as starting materials are disclosed in WO 2004/085449. [IrCl$_2$(acac)$_2$]$^-$, for example Na[IrCl$_2$(acac)$_2$], is particularly suitable.

The complexes are preferably synthesised as described in WO 2002/060910 and in WO 2004/085449. Heteroleptic complexes can also be synthesised, for example, in accordance with WO 2005/042548. The synthesis can also be activated, for example, thermally, photochemically and/or by microwave radiation.

These processes enable the compounds of the formula (1) according to the invention to be obtained in high purity, preferably greater than 99% (determined by means of $^1$H-NMR and/or HPLC).

The synthetic methods explained here enable the preparation of, inter alia, structures 1 to 154 according to the invention depicted below.

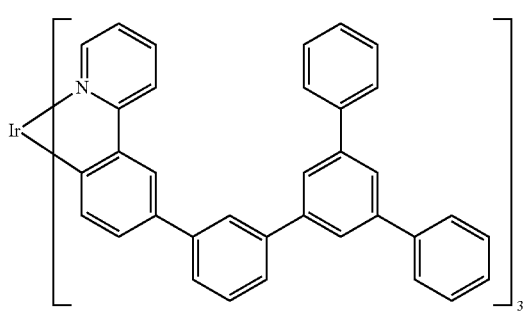

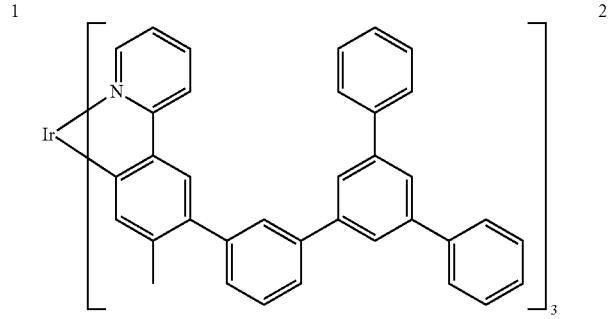

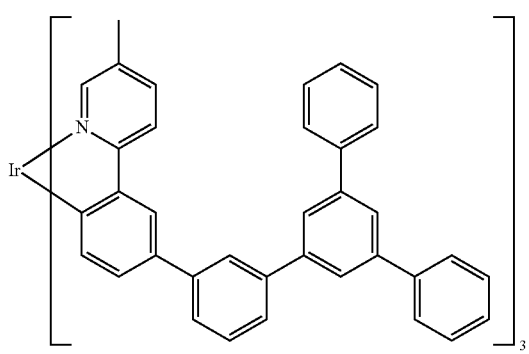

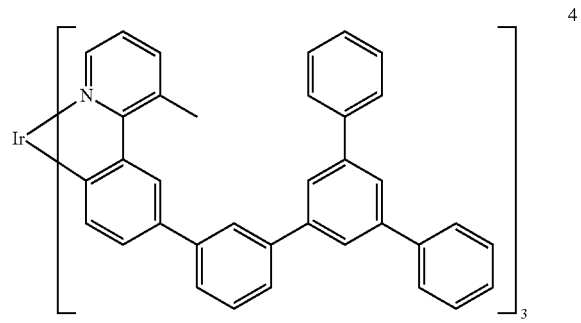

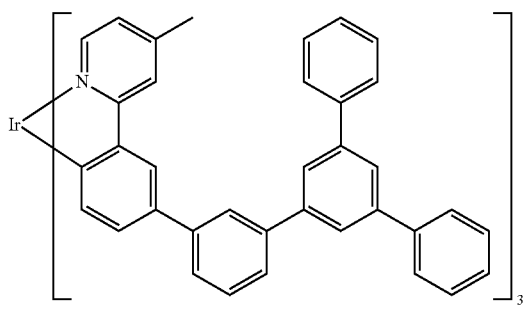

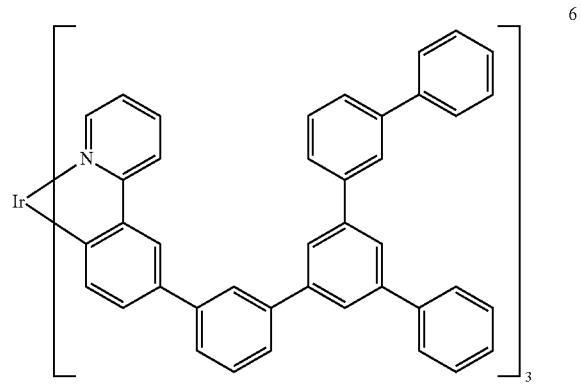

-continued
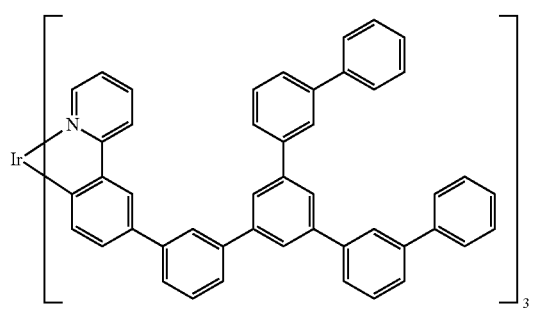
7
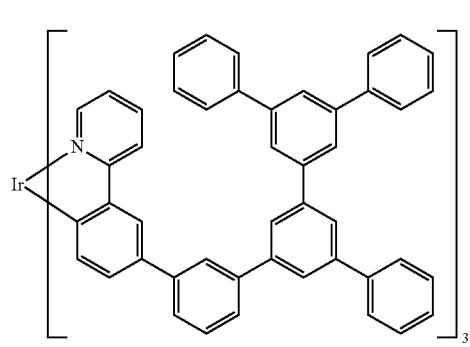
8
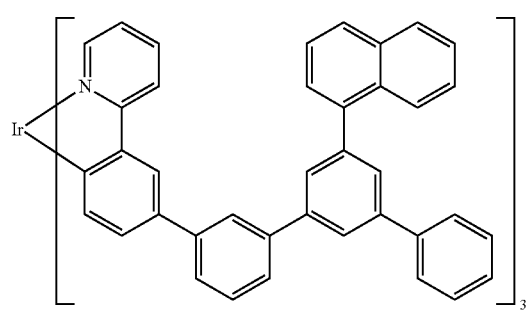
9
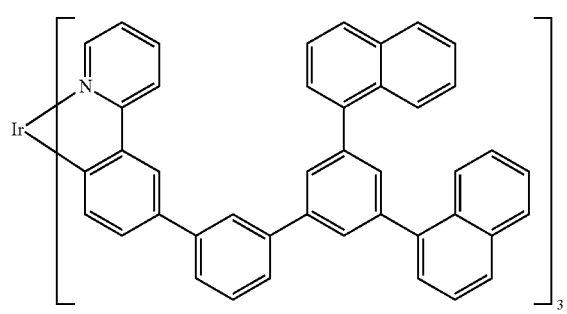
10
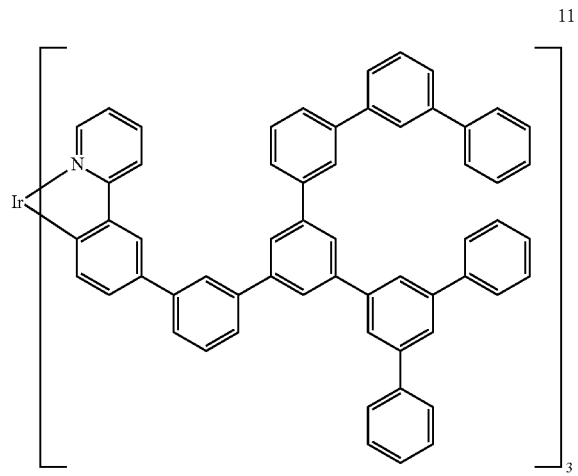
11
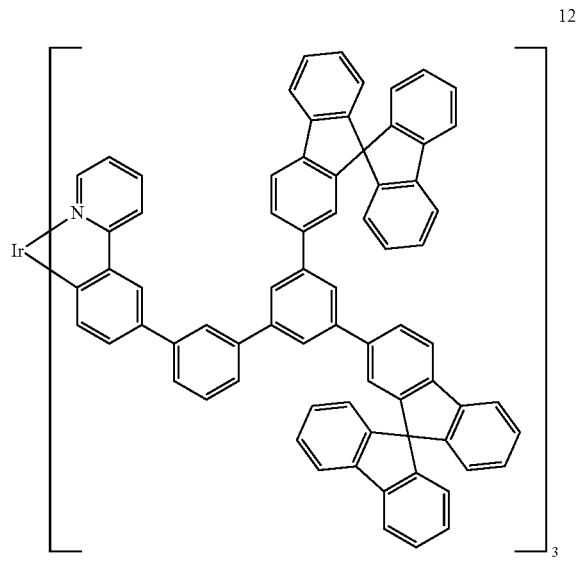
12
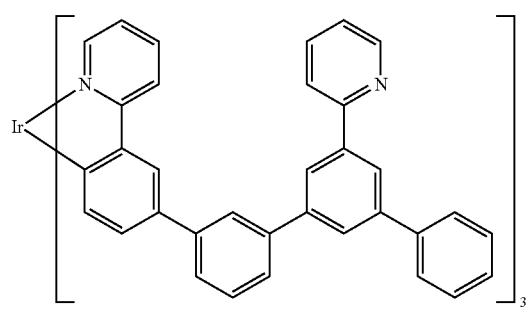
13
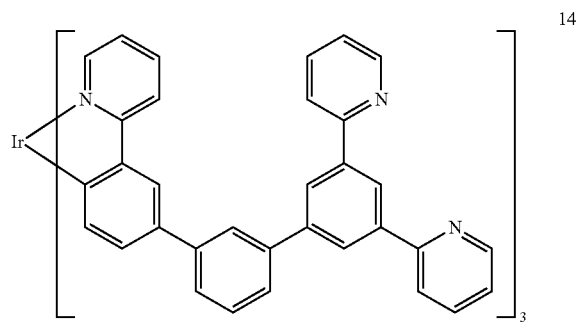
14

-continued
15
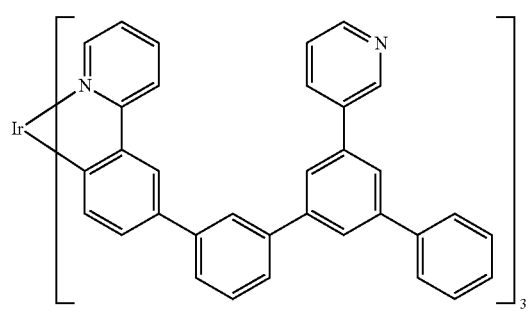
16
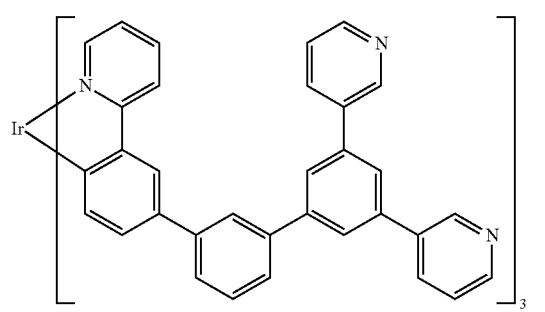
17
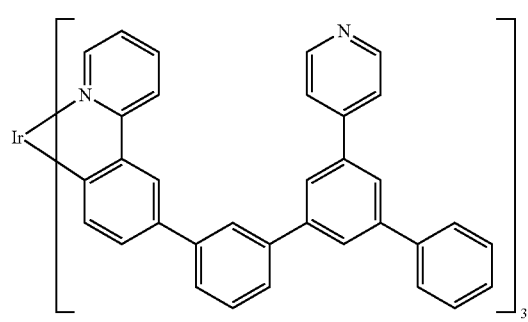
18
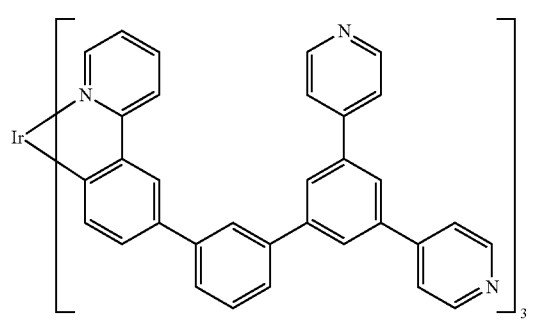
19
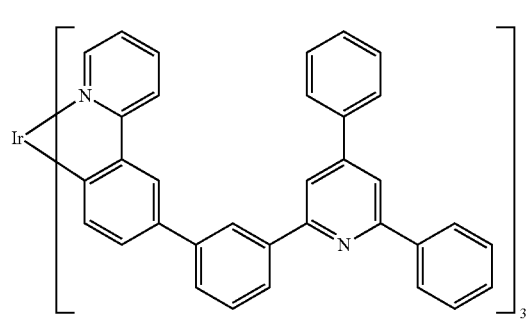
20
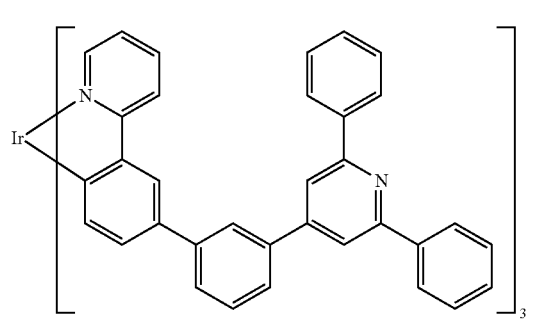
21
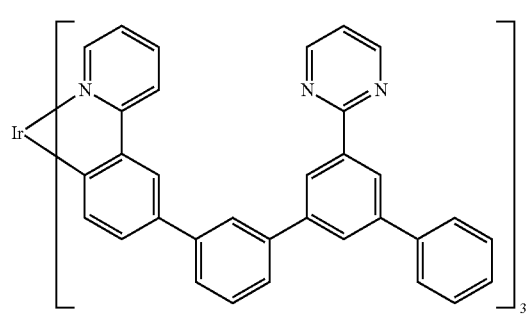
22
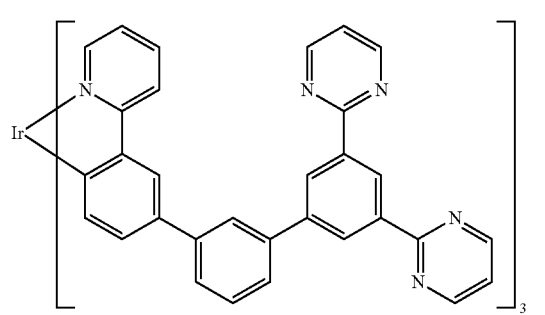
23
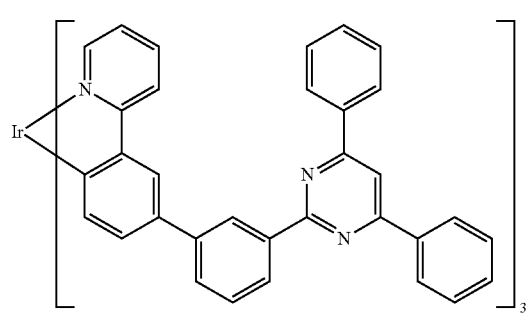
24
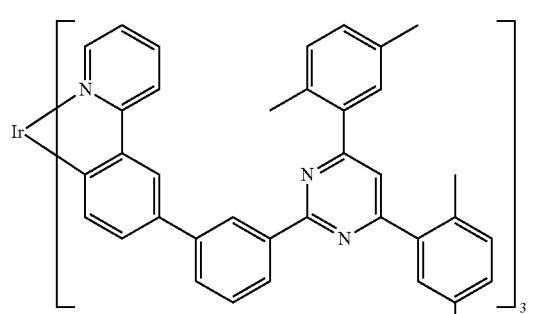

-continued
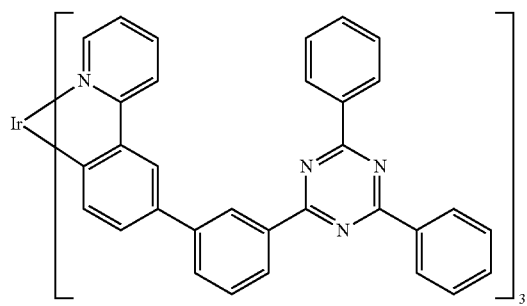
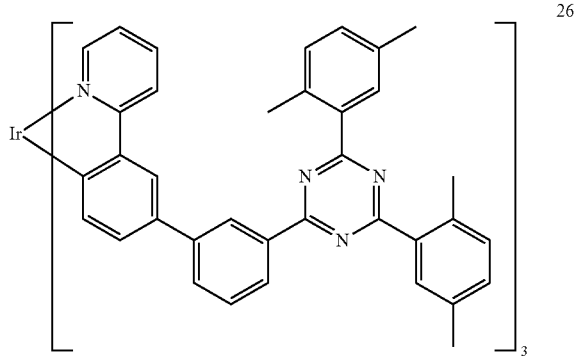
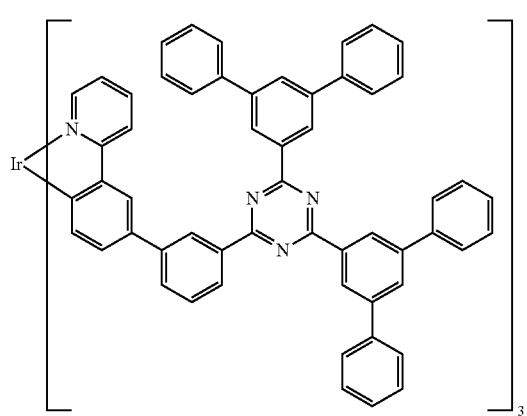
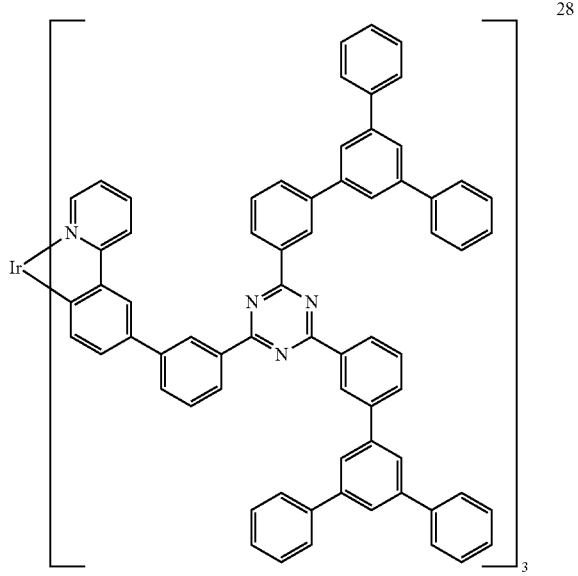
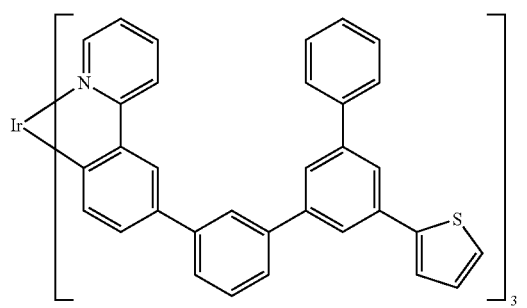
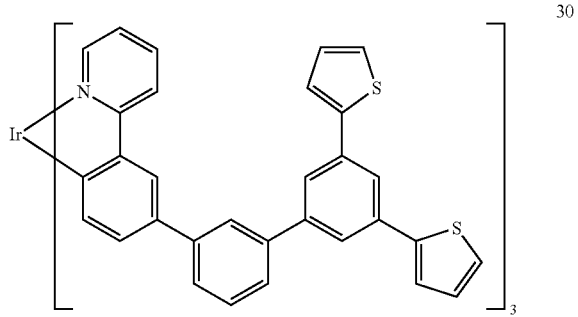
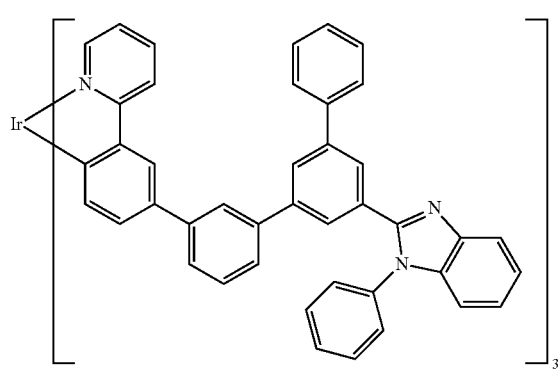
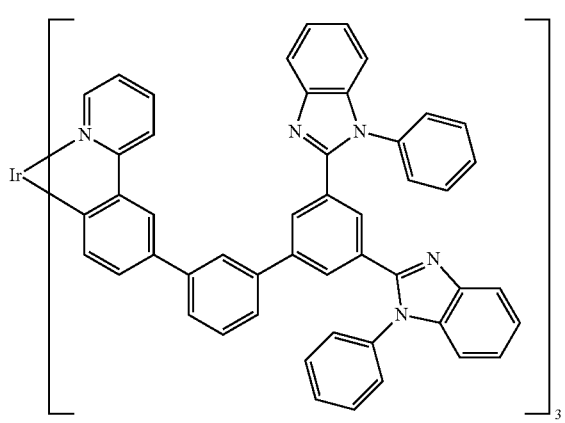

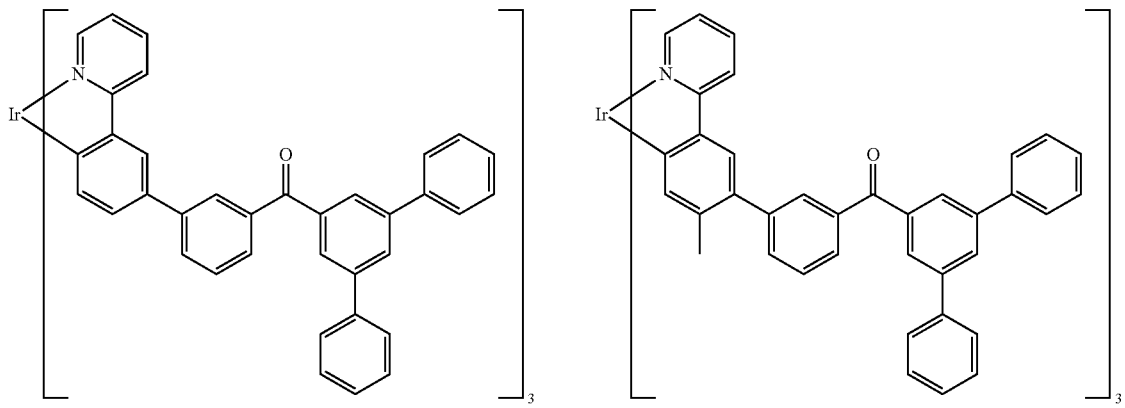
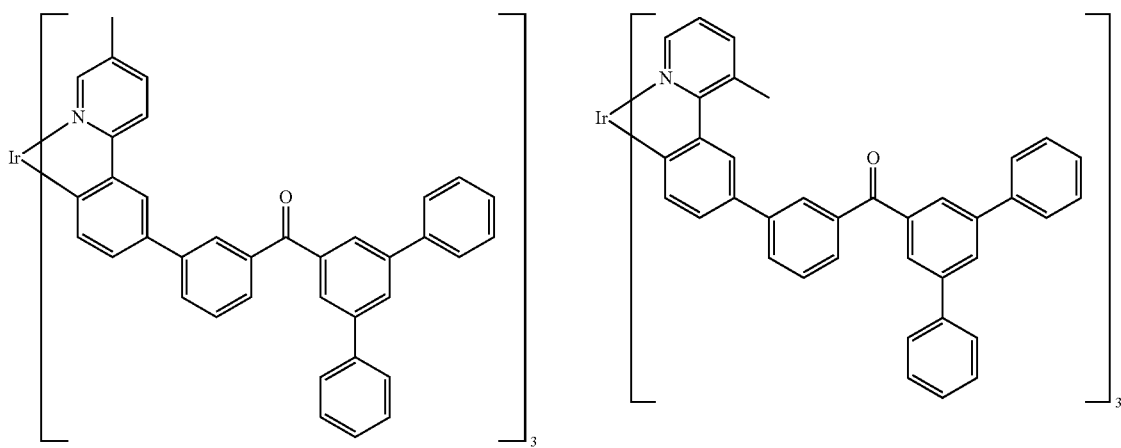
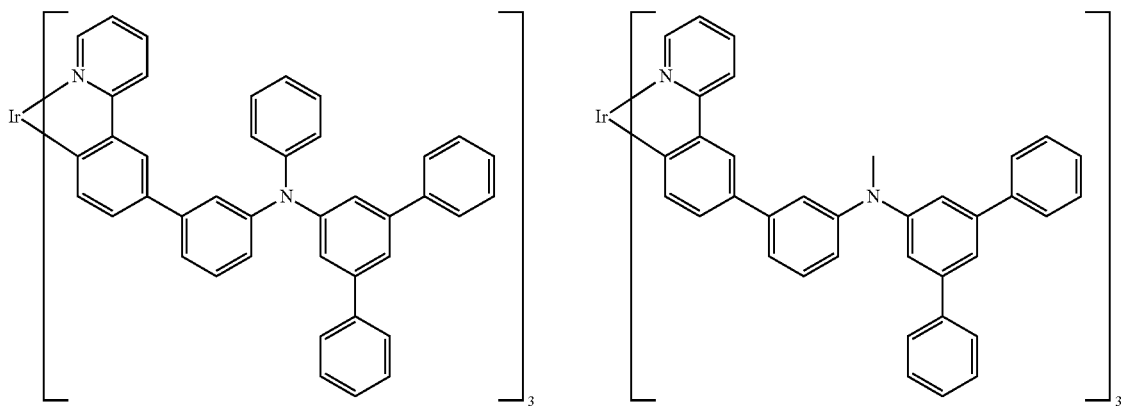

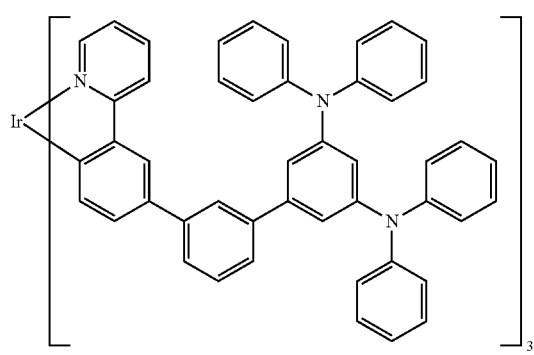
39
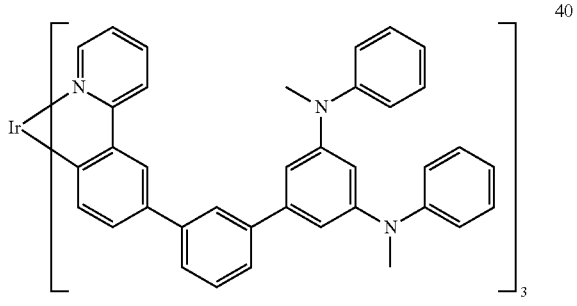
40
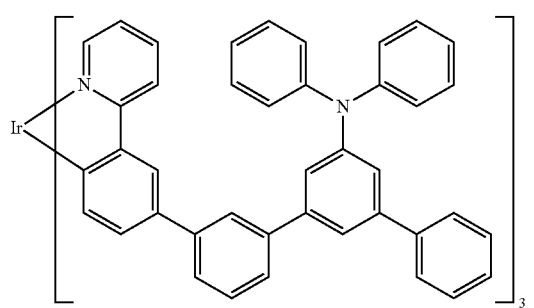
41
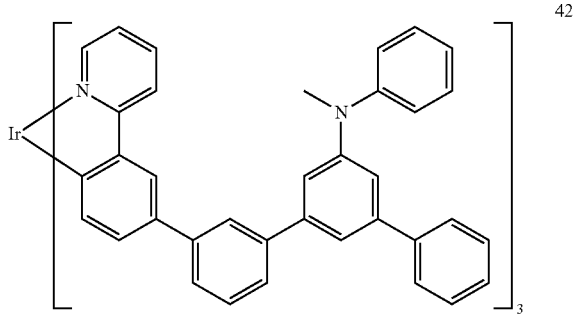
42
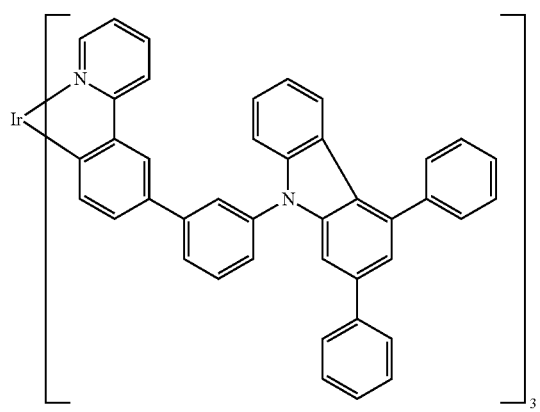
43
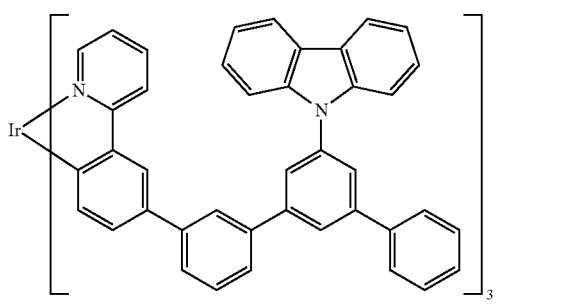
44
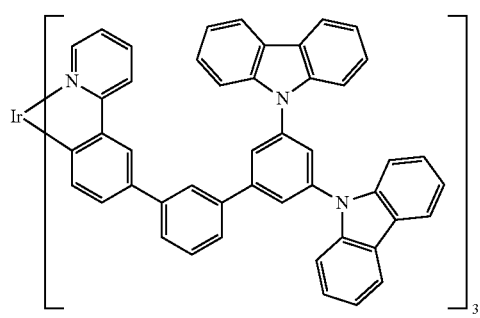
45
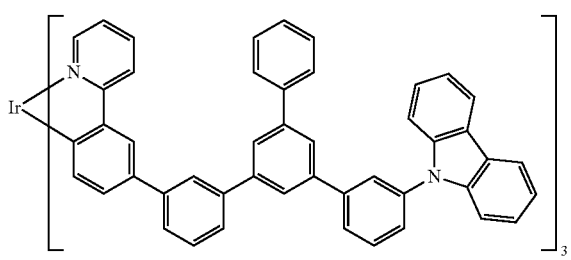
46

-continued
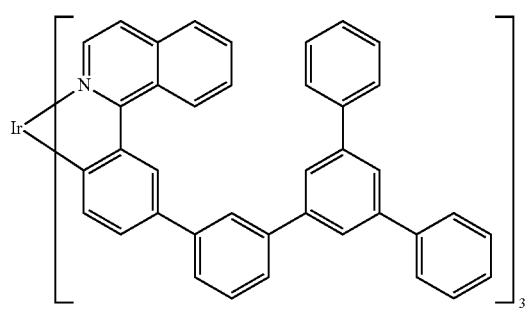
47
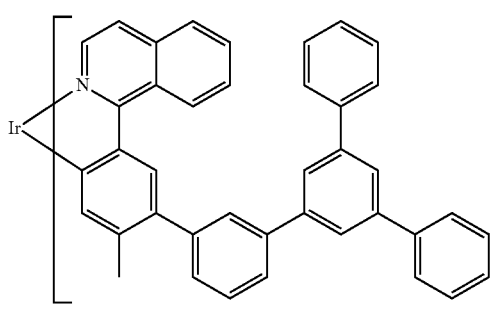
48
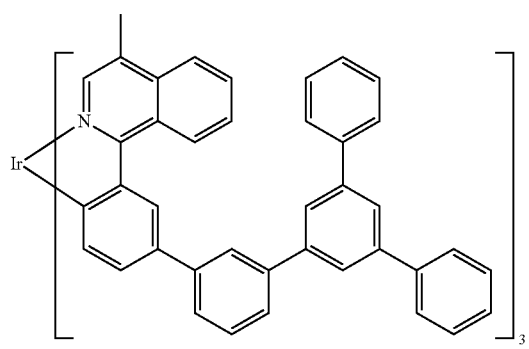
49
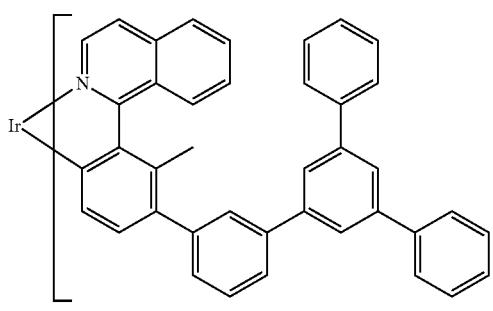
50
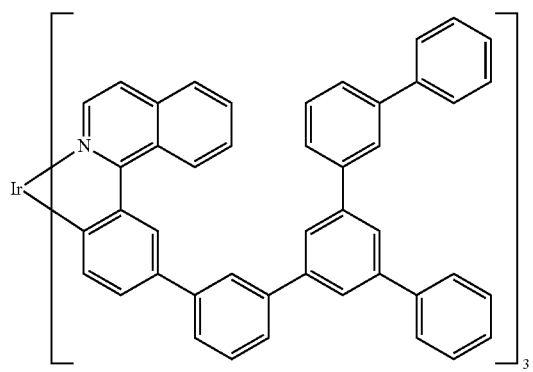
51
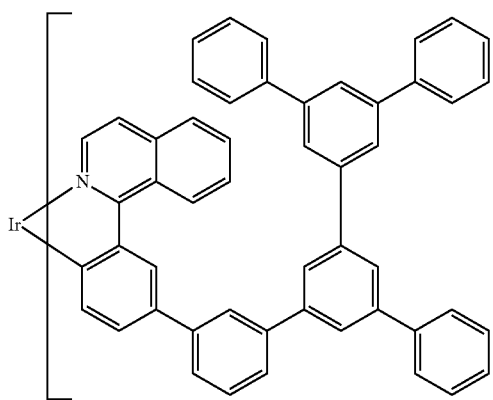
52
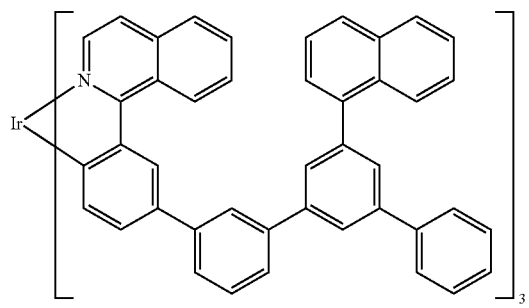
53
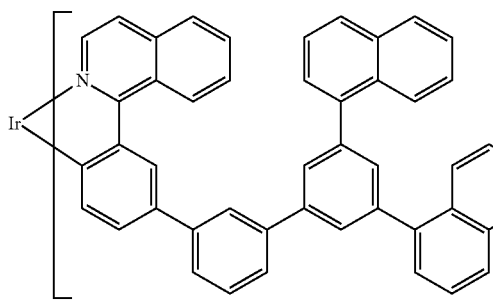
54

-continued
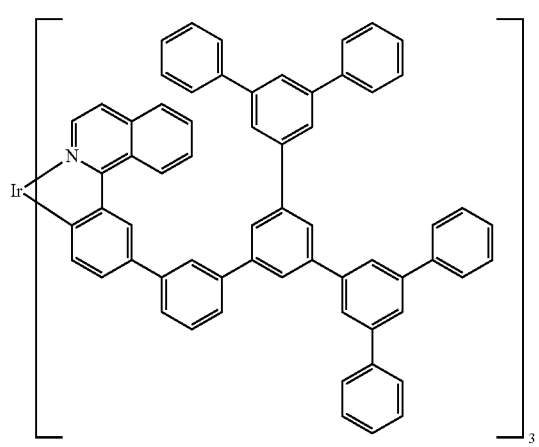
55
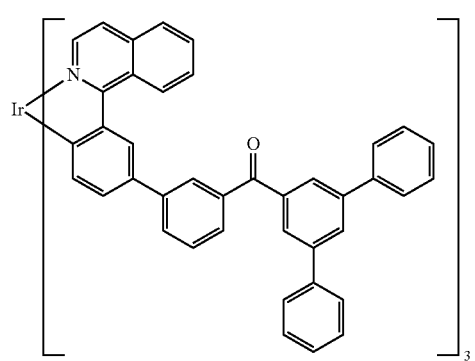
56
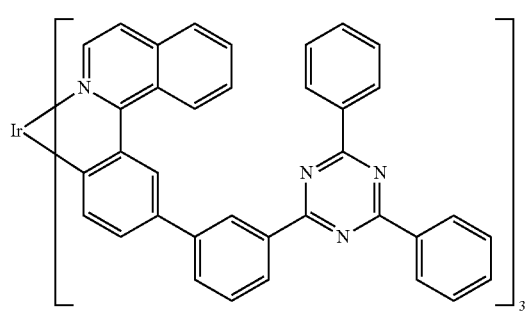
57
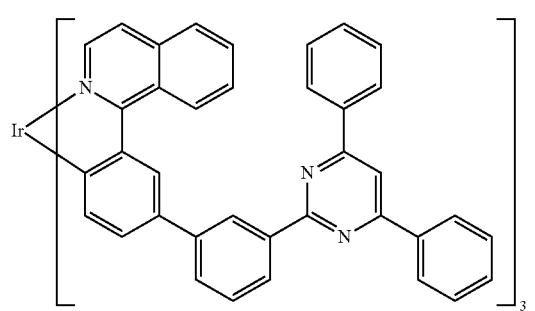
58
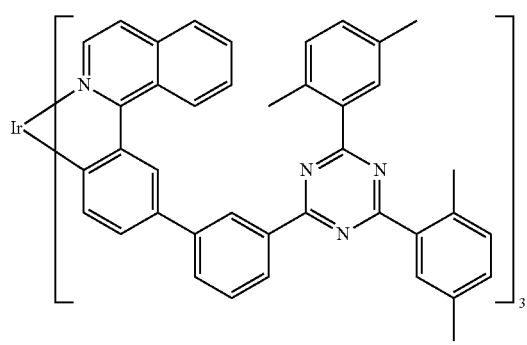
59
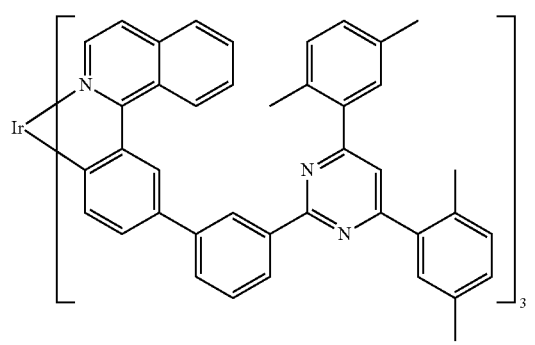
60
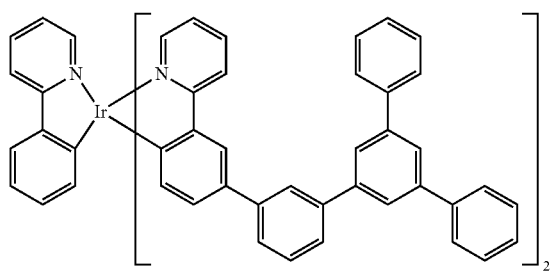
61
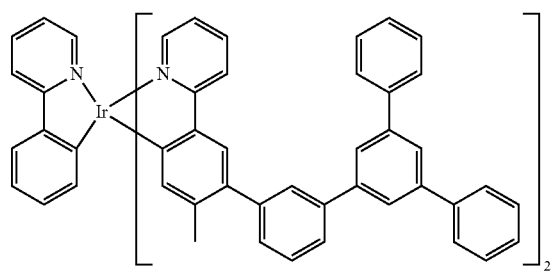
62

-continued
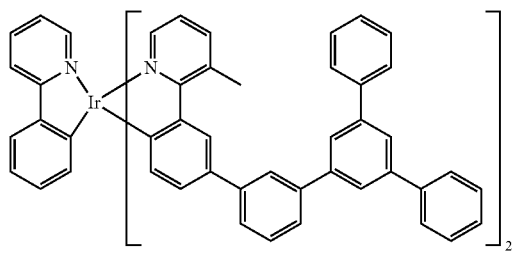
63
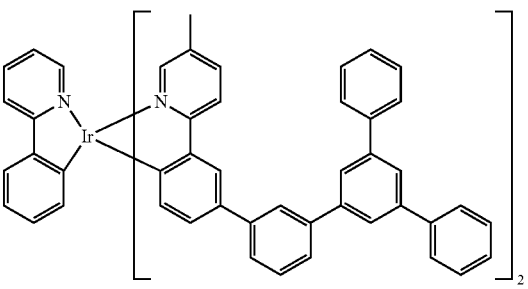
64
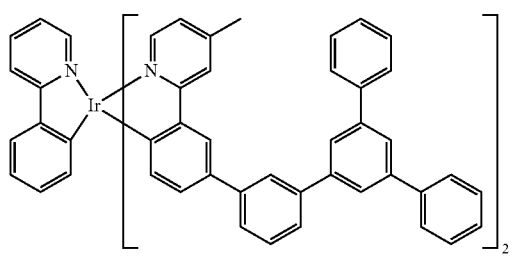
65
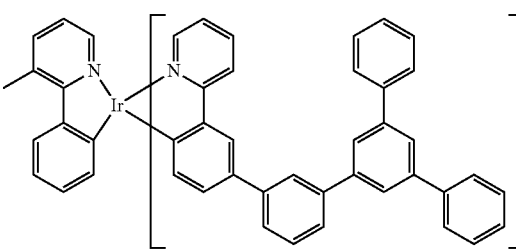
66
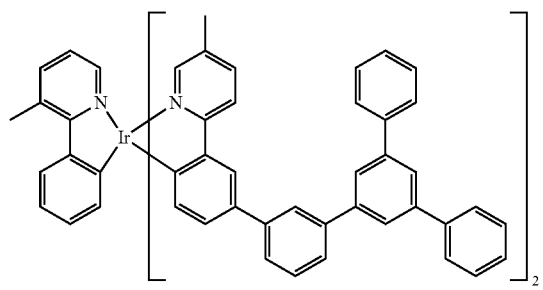
67
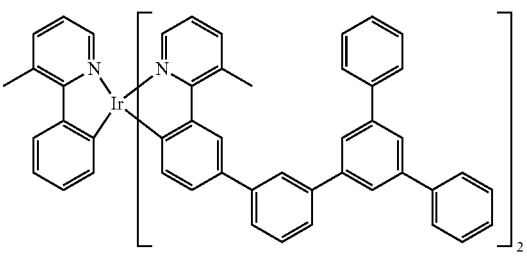
68
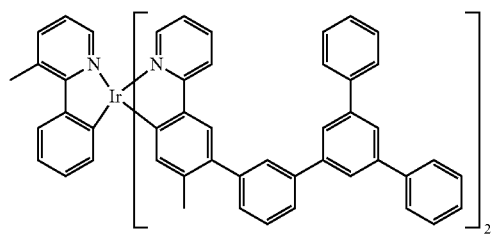
69
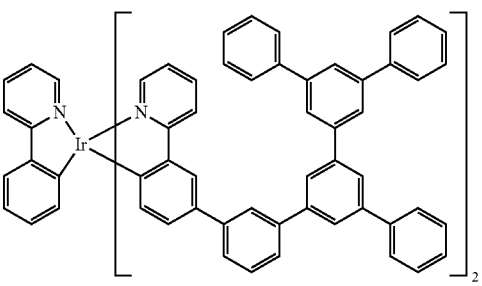
70
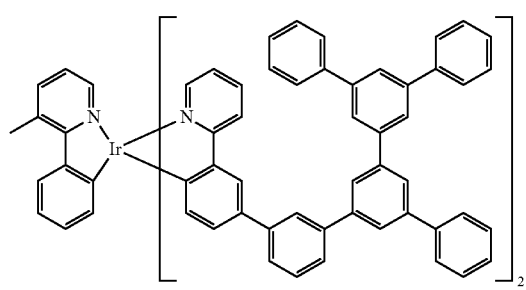
71
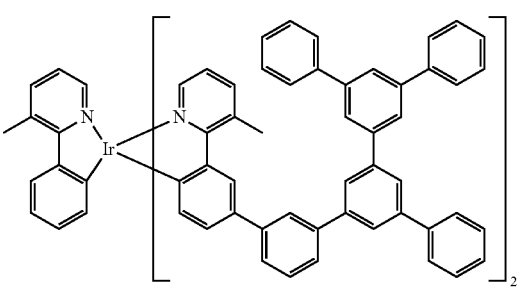
72

-continued
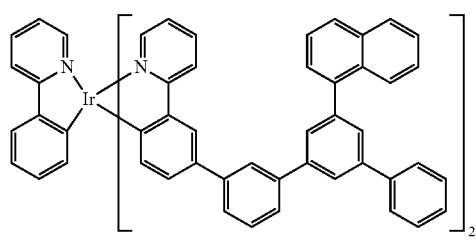
73
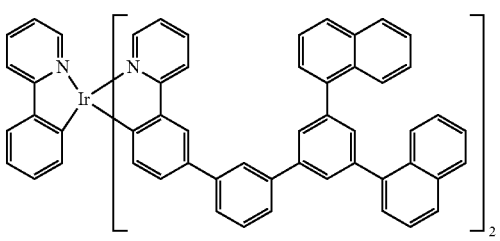
74
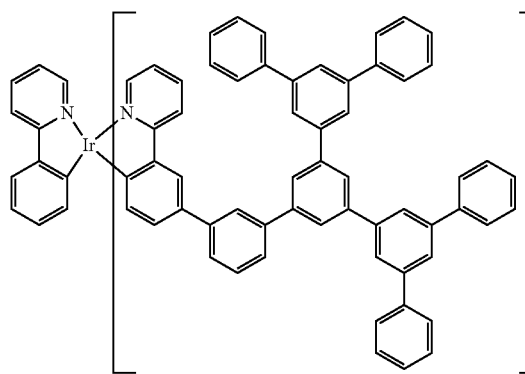
75
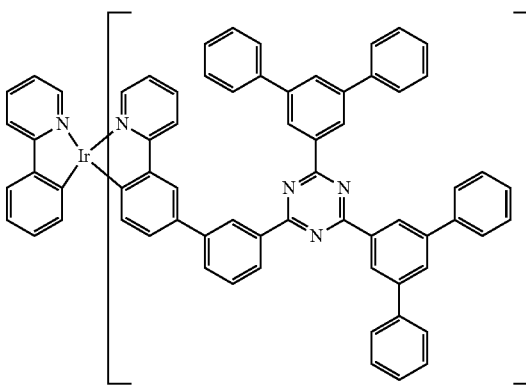
76
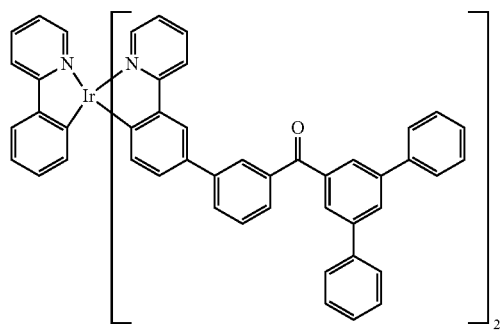
77
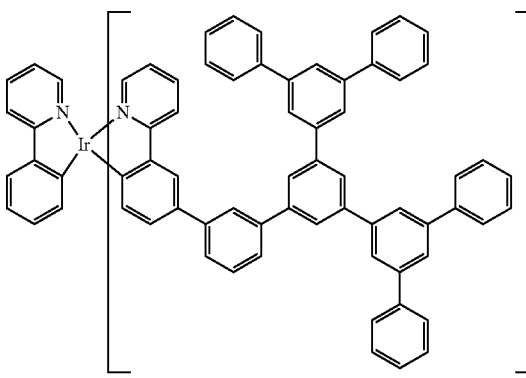
78
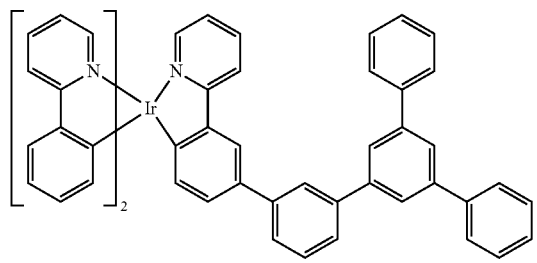
79
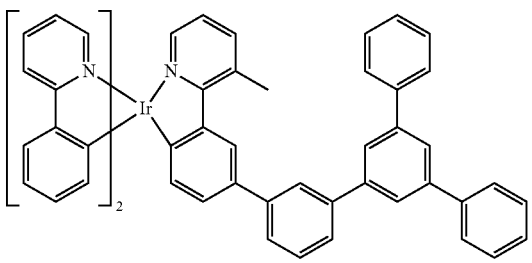
80
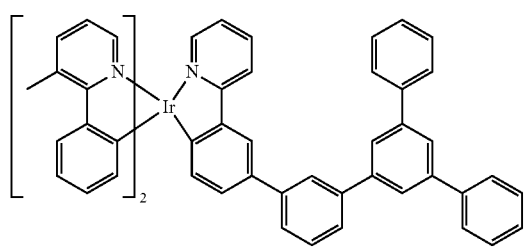
81
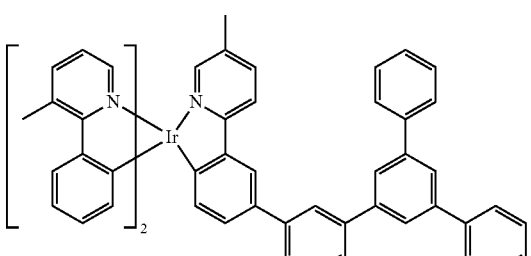
82

-continued
83
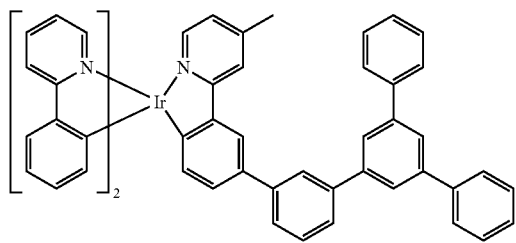
84
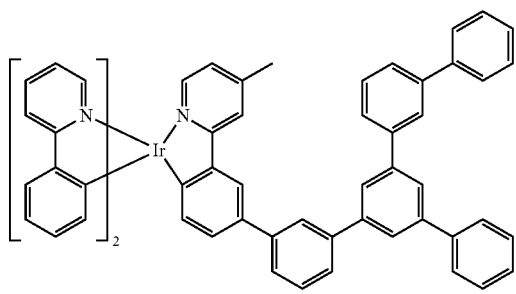
85
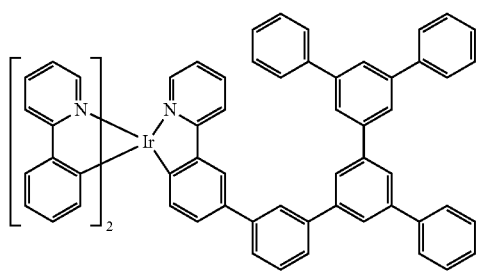
86
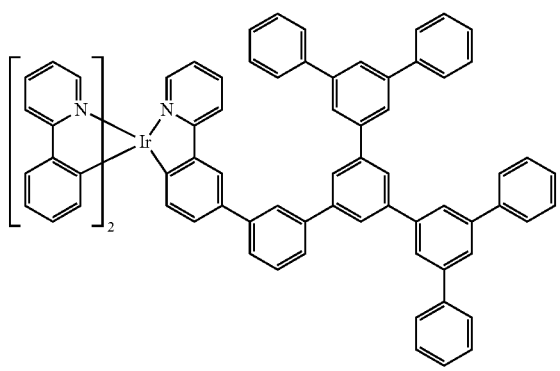
87
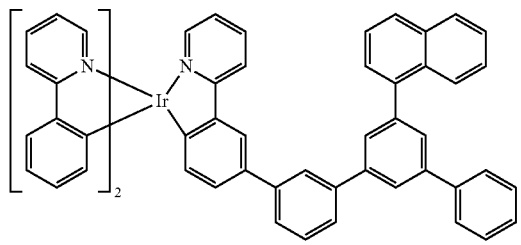
88
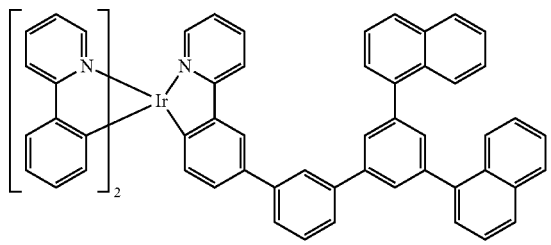
89
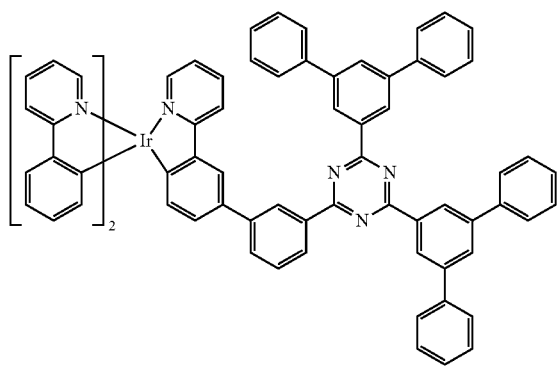
90
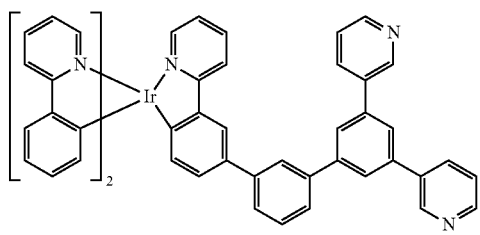

-continued
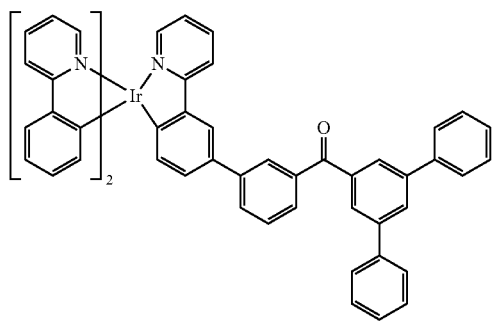
91
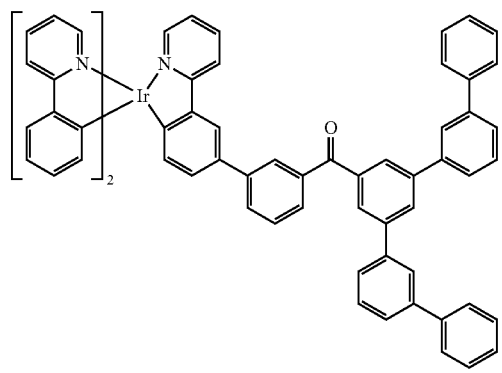
92
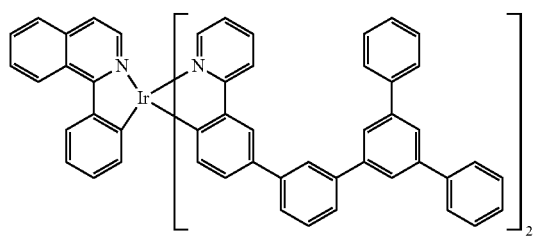
93
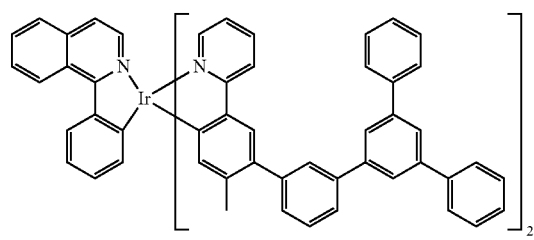
94
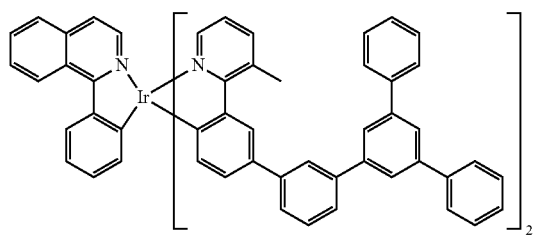
95
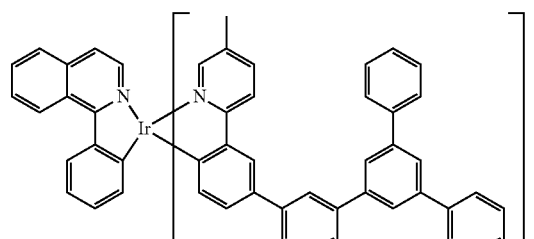
96
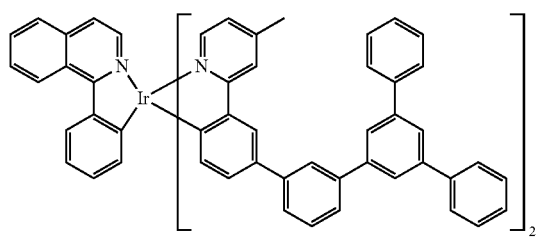
97
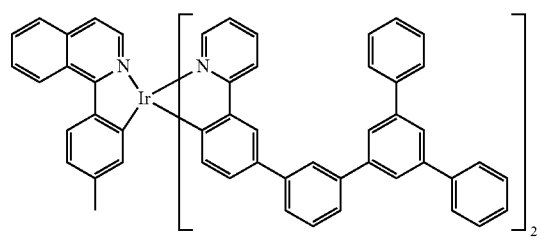
98
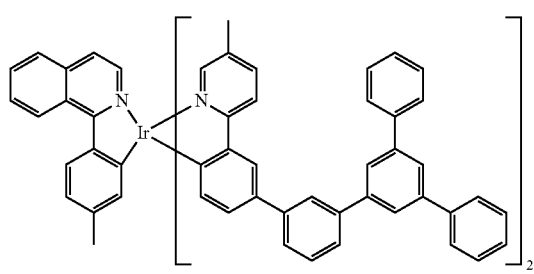
99
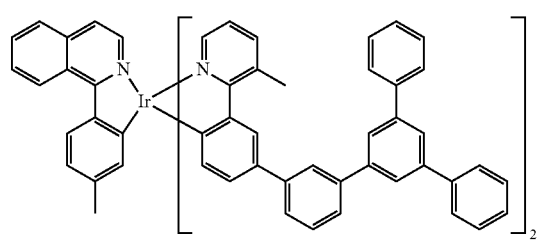
100

-continued
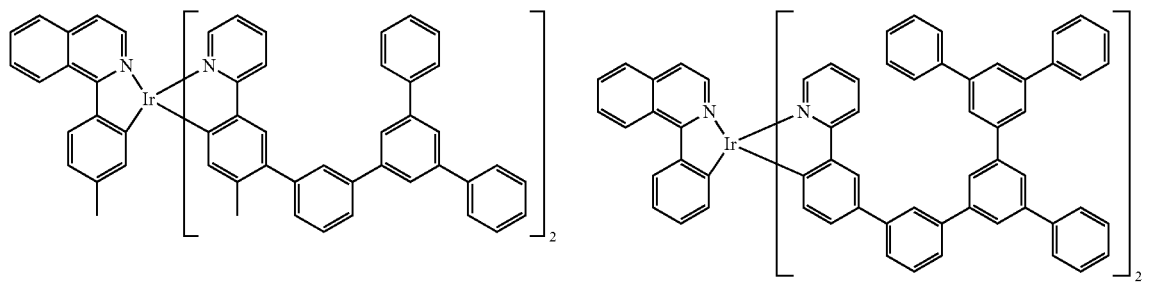
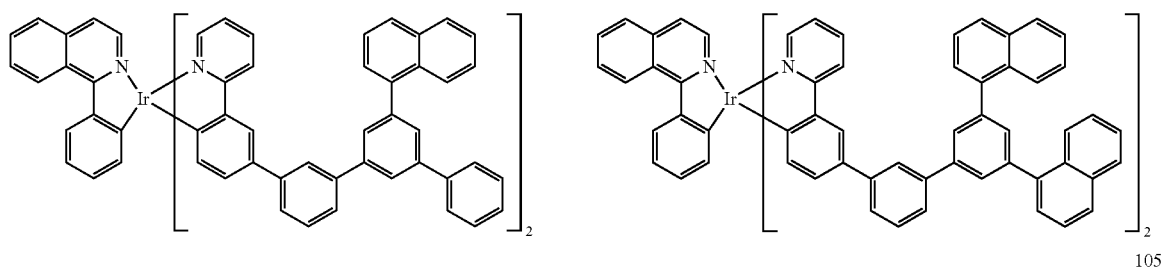
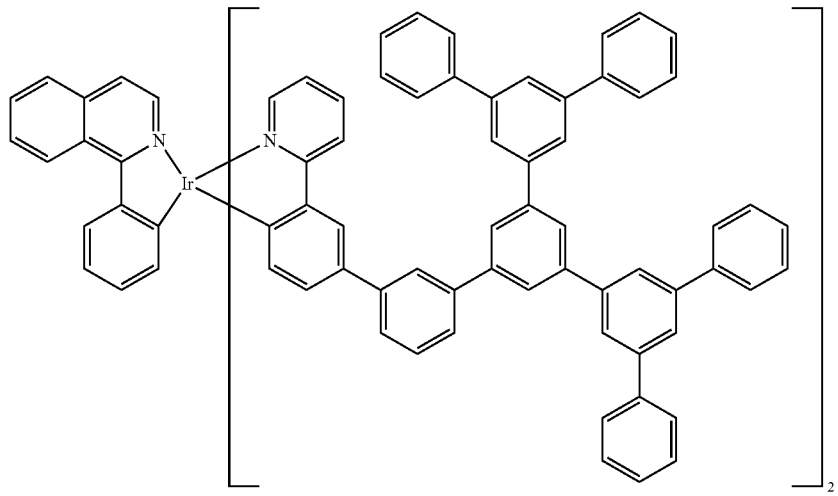
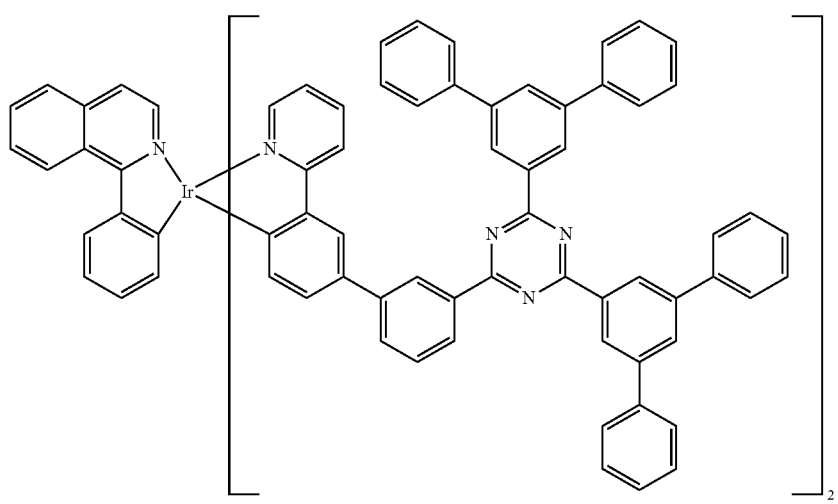

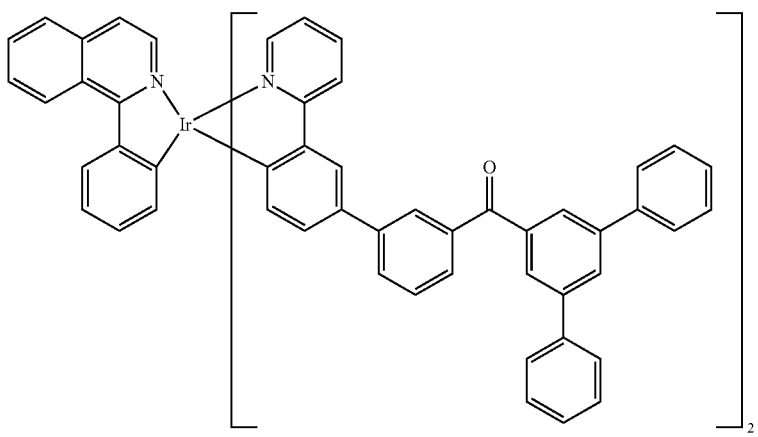
107
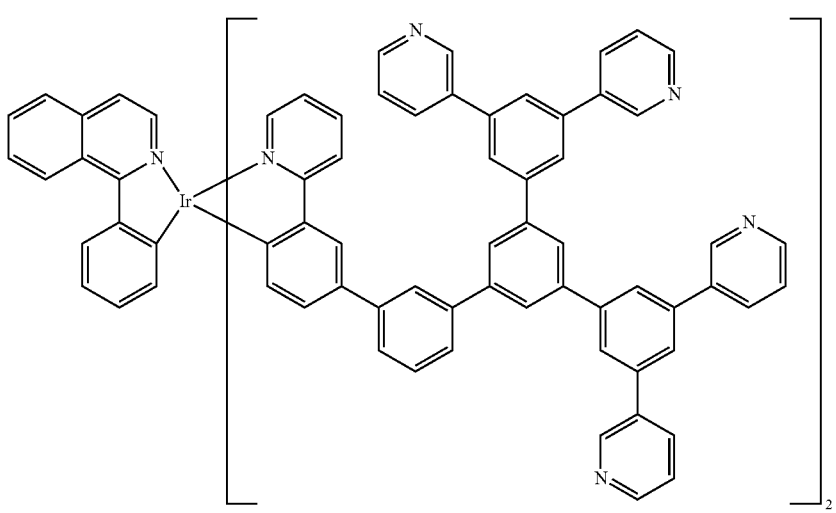
108
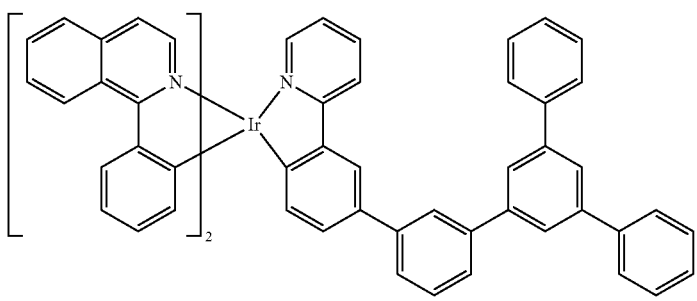
109
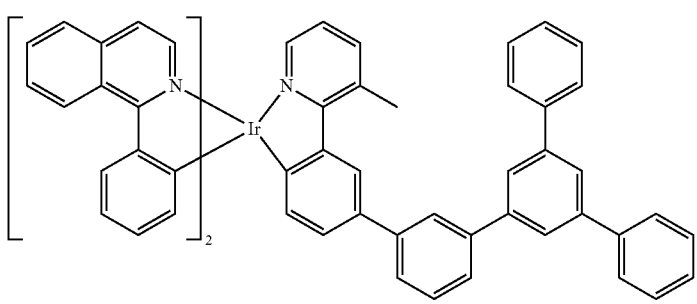
110

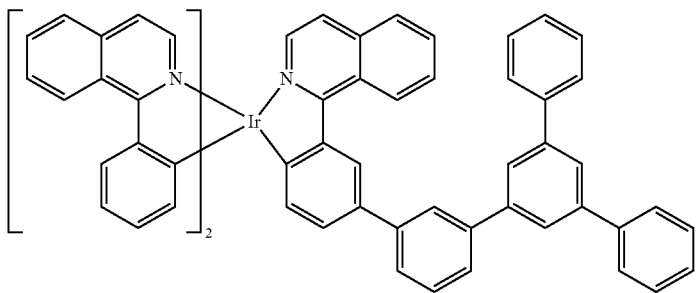
111
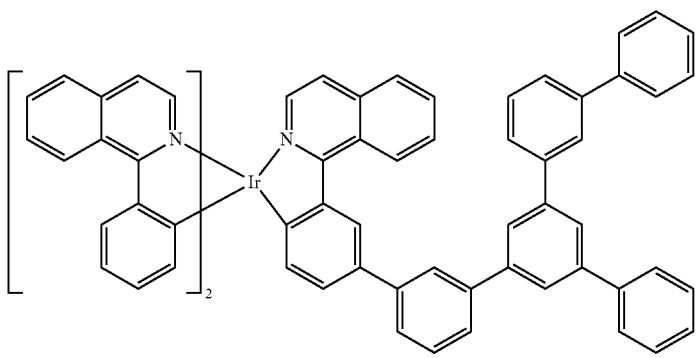
112
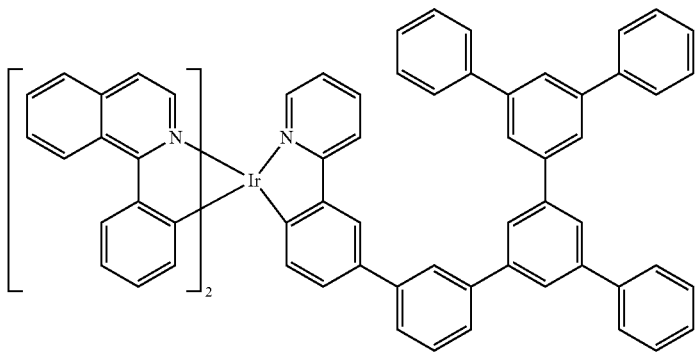
113
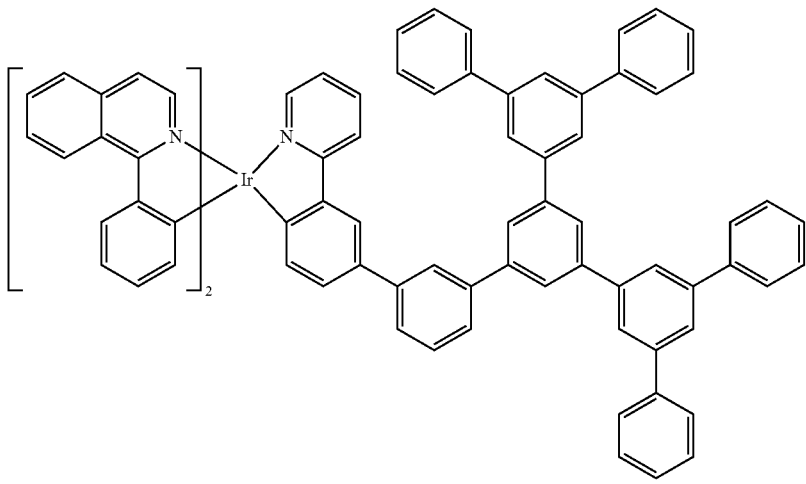
114

-continued
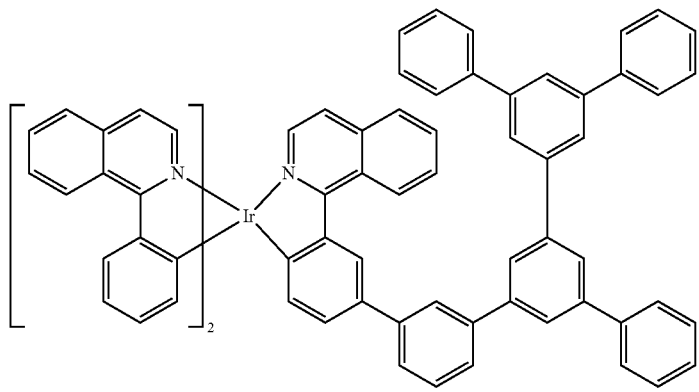
115
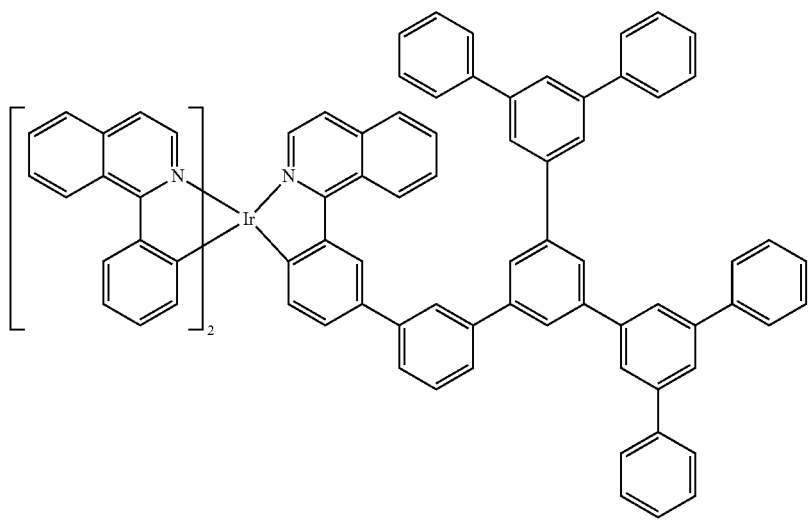
116
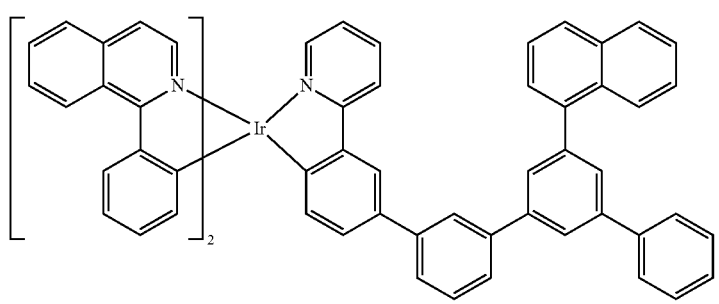
117
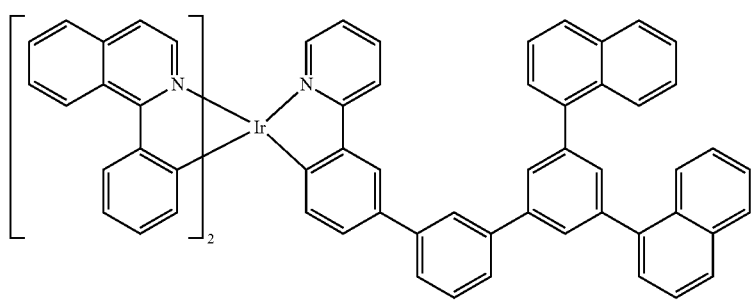
118

119
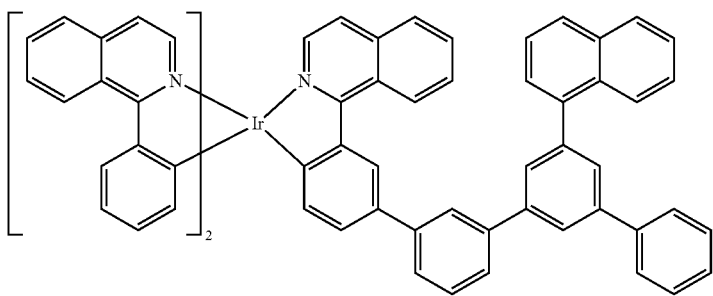
120
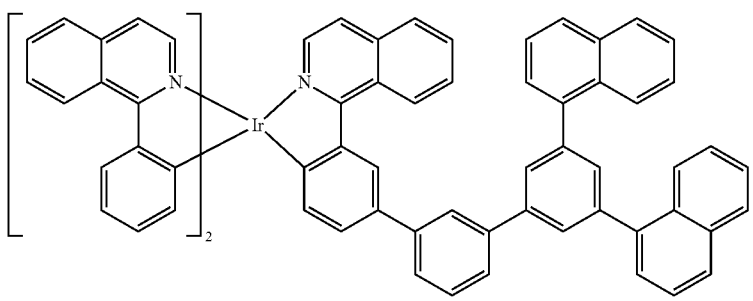
121
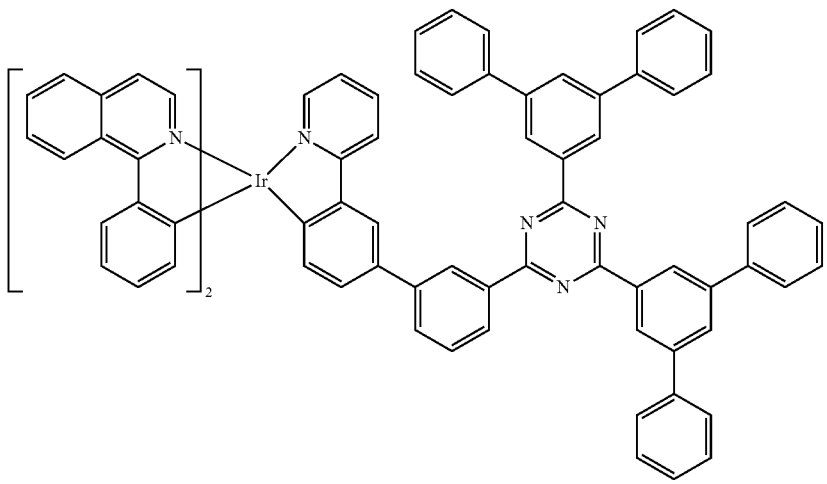
122
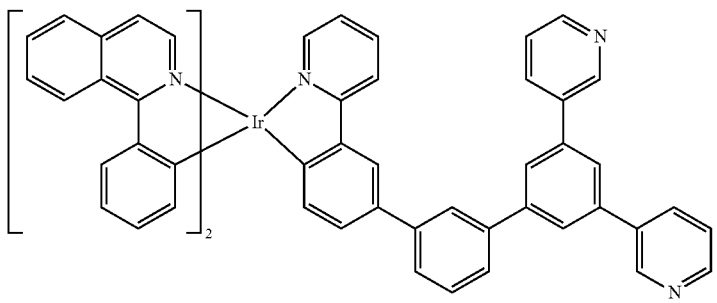

123
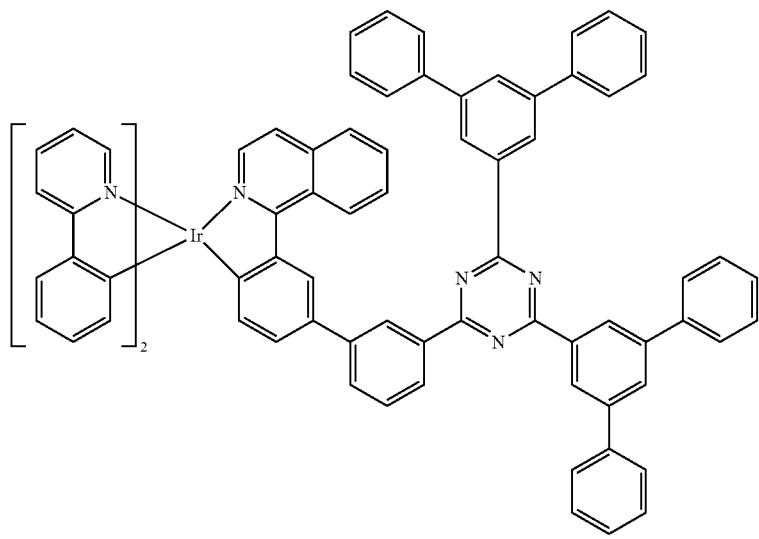
124
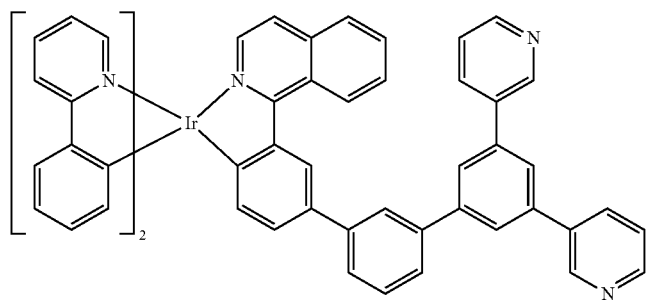
125
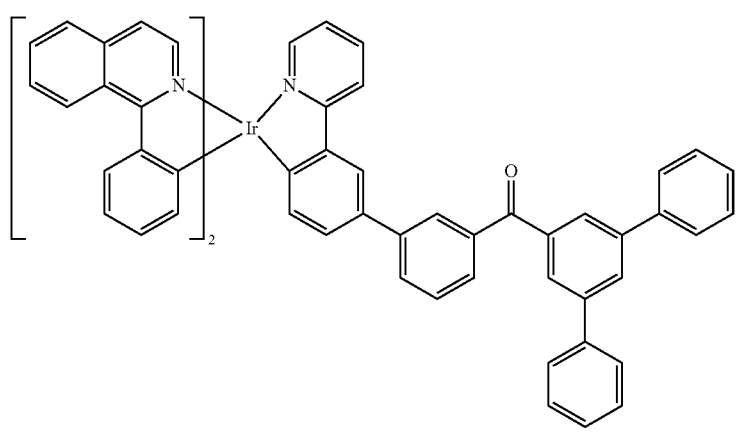

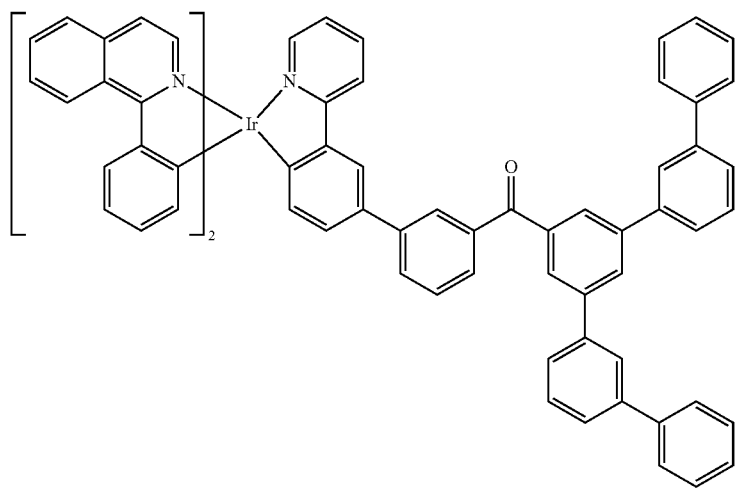
126
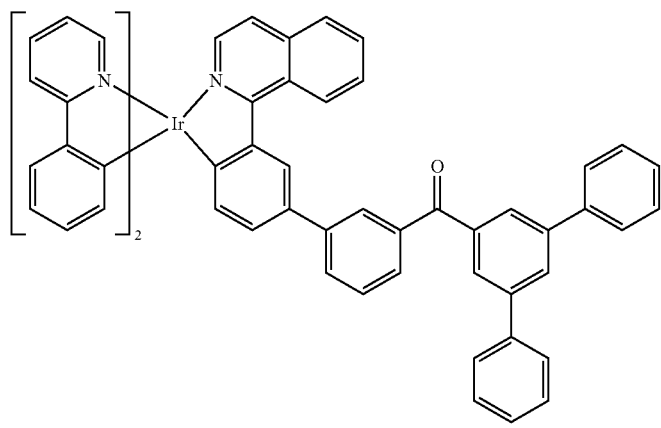
127
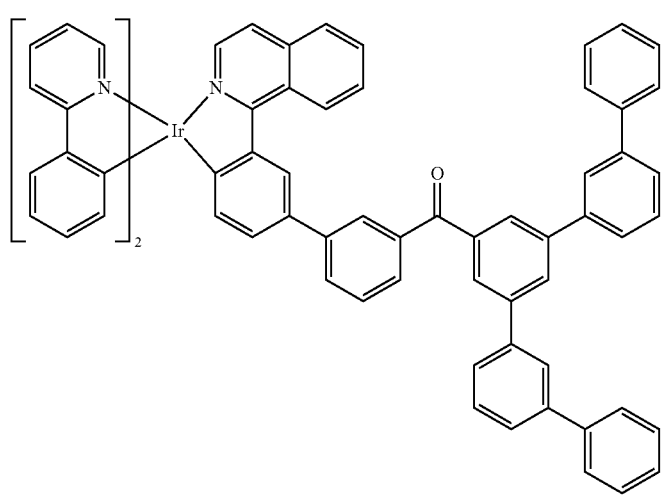
128

129
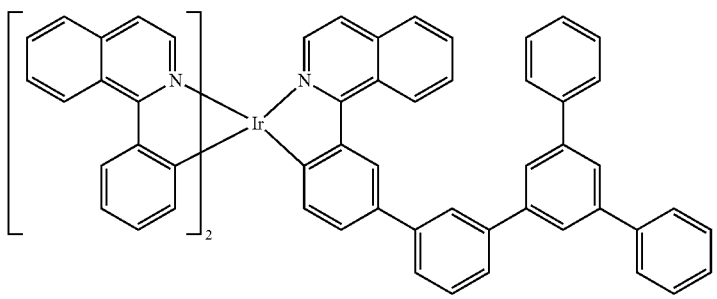
130
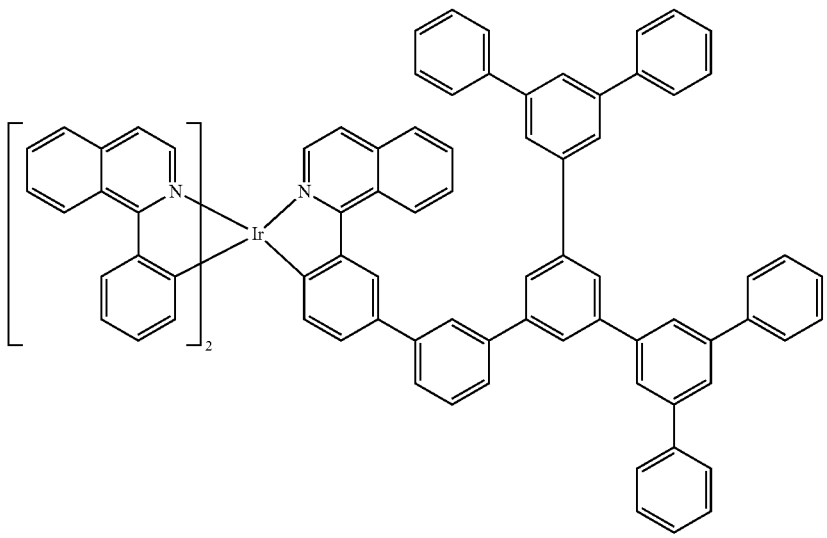
131
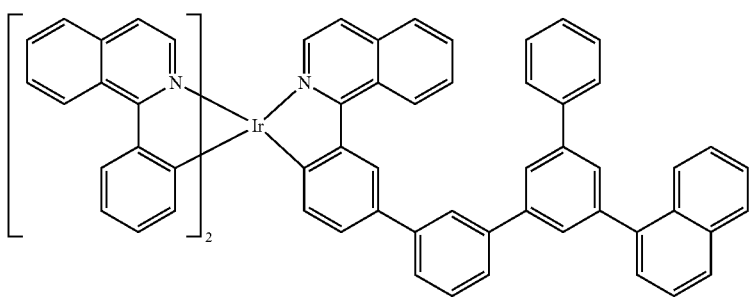
132
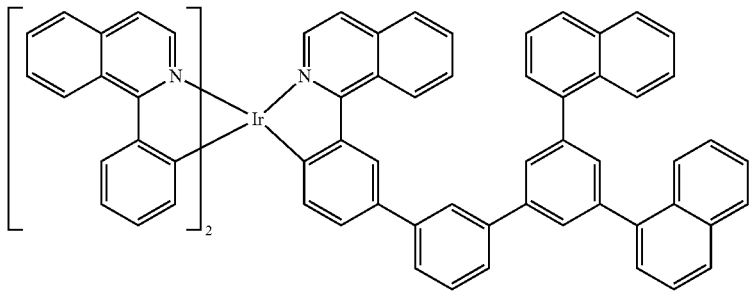

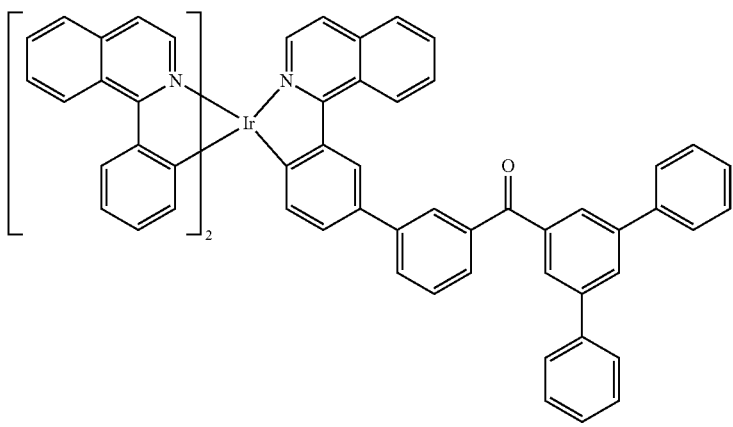
133
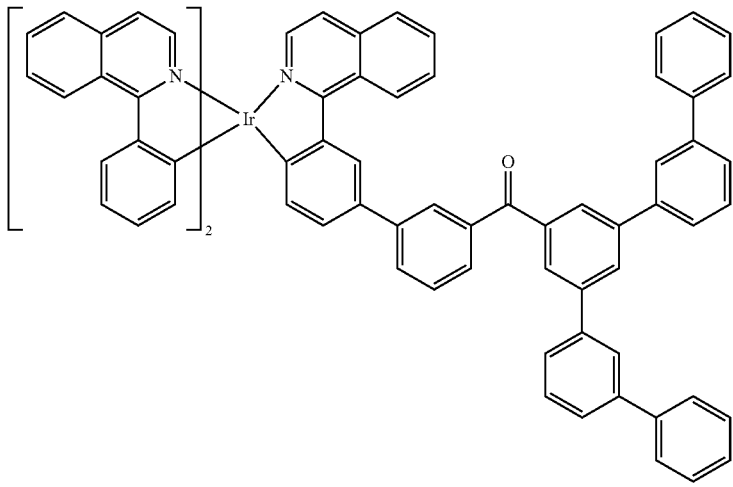
134
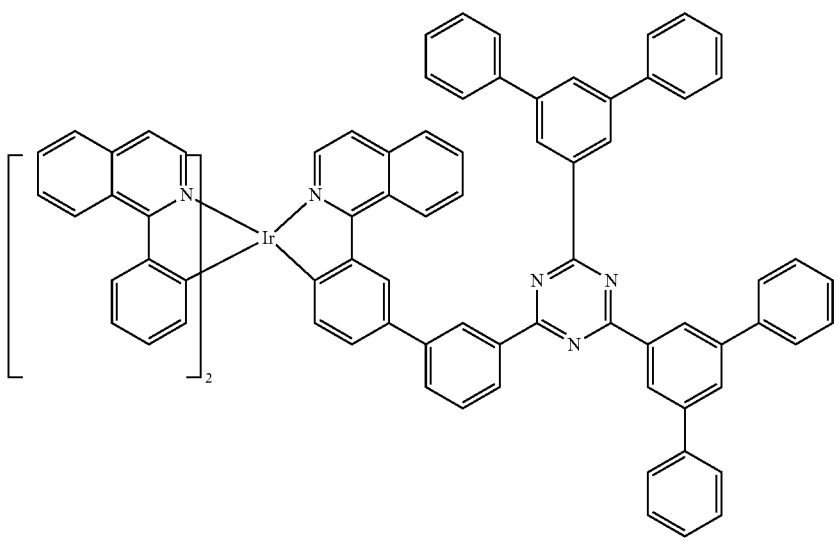
135

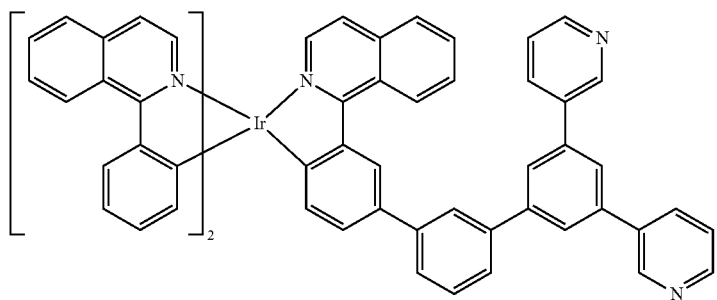
136
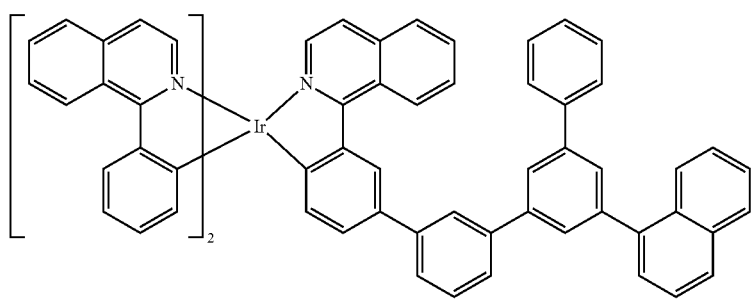
137
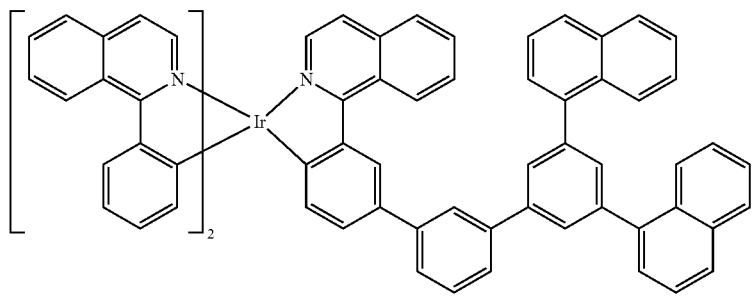
138
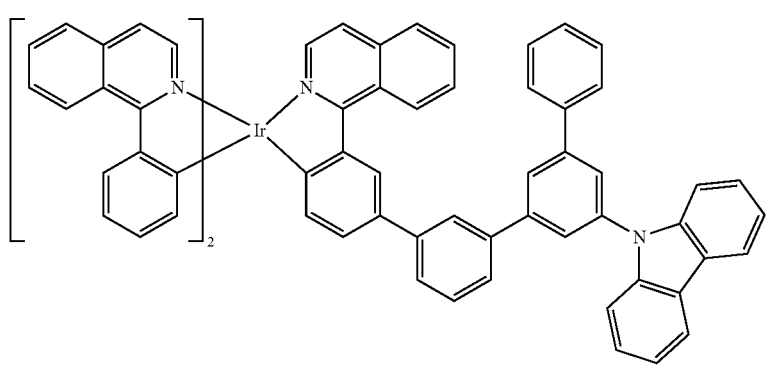
139

140
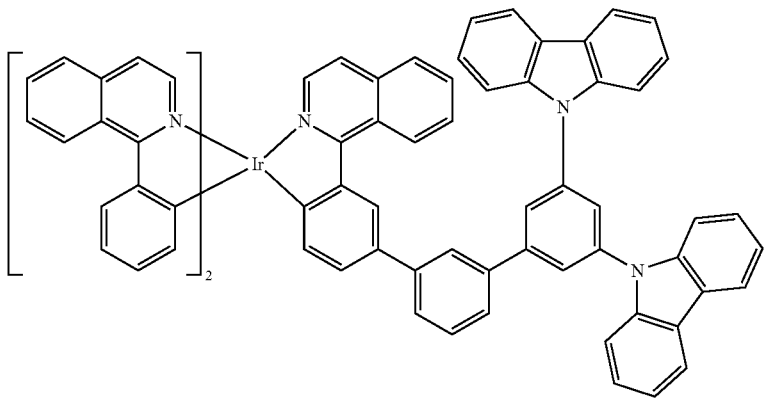
141
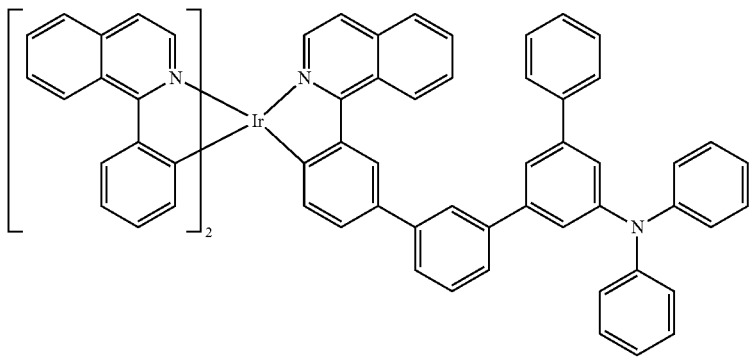
142
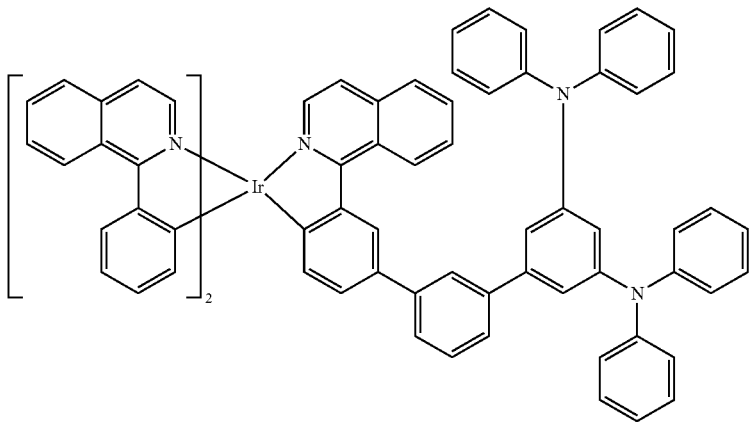
143
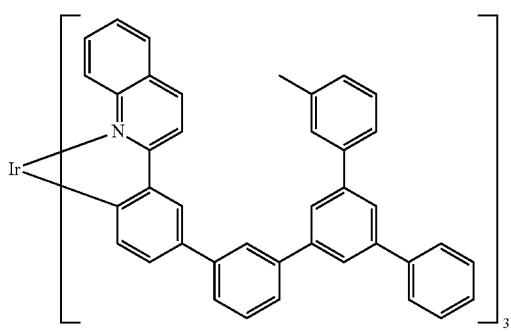
144
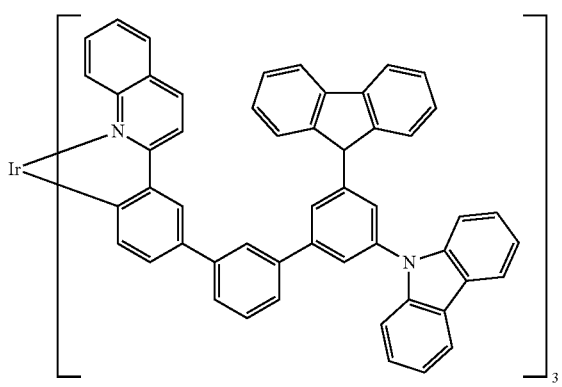

-continued
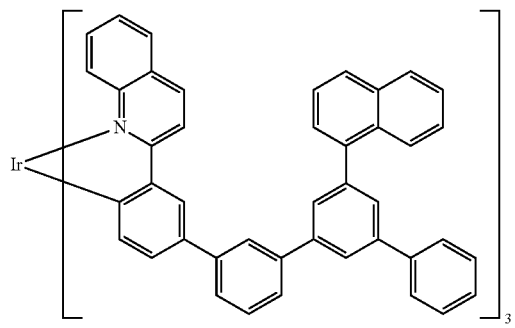
145
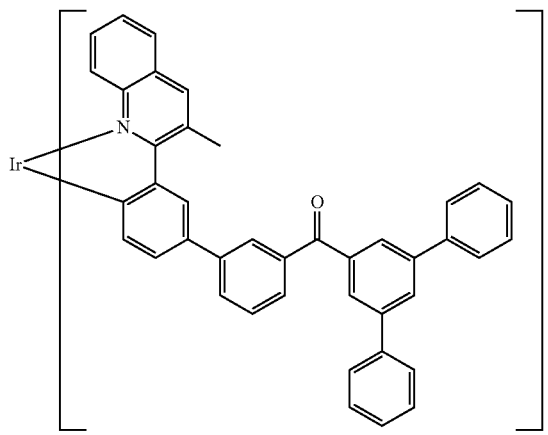
146
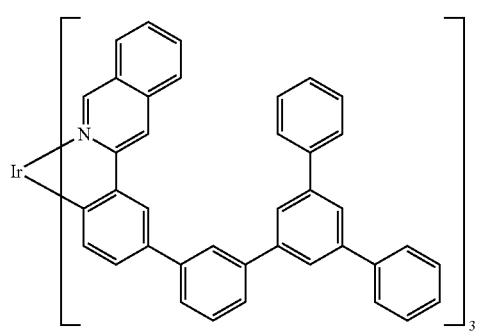
147
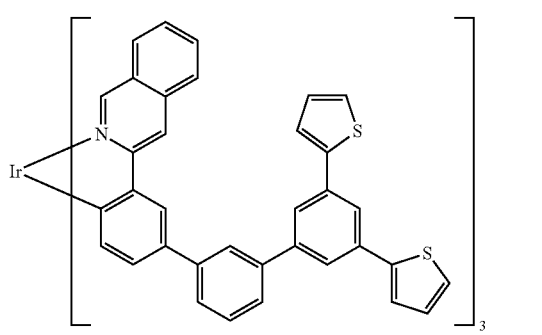
148
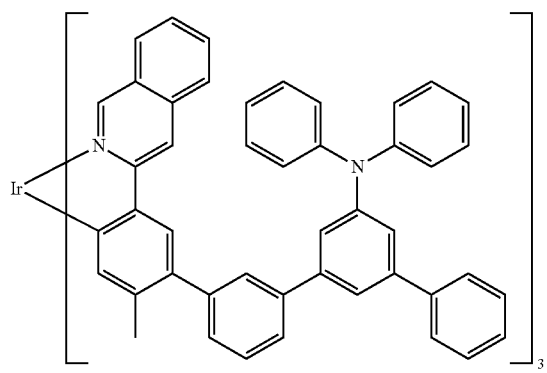
149
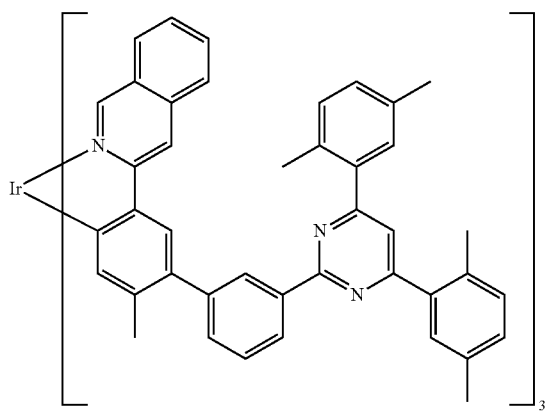
150
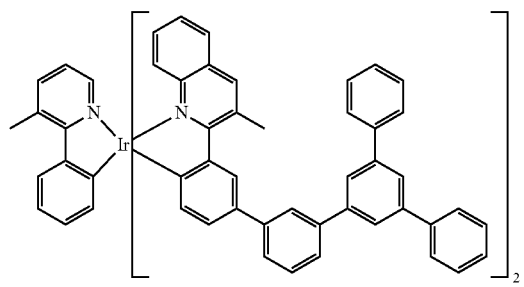
151
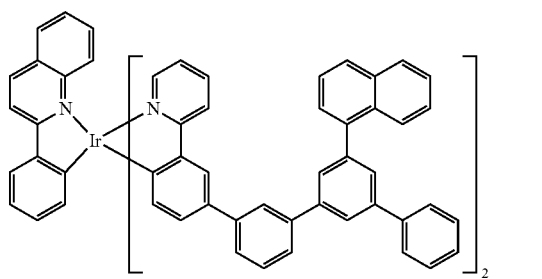
152

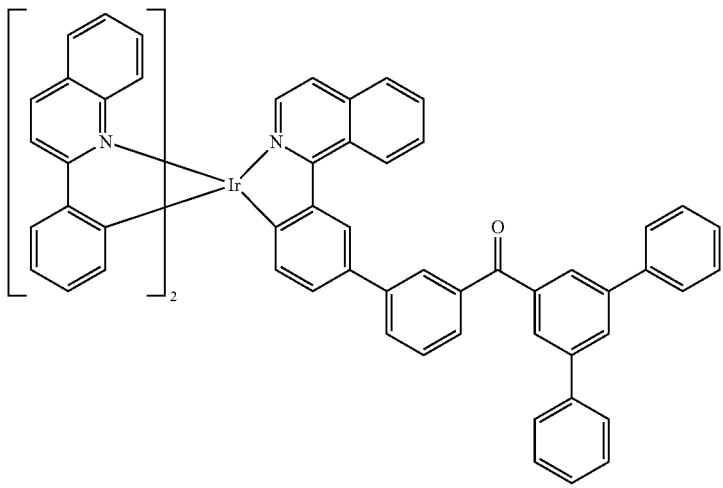

153

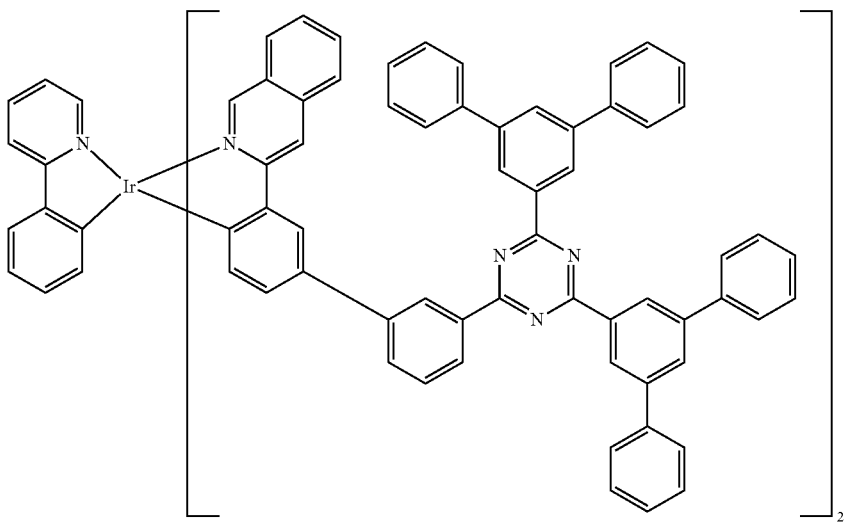

154

The complexes of the formula (1) described above and the preferred embodiments mentioned above can be used as active component in an electronic device. An electronic device is taken to mean a device which comprises an anode, a cathode and at least one layer, where this layer comprises at least one organic or organometallic compound. The electronic device according to the invention thus comprises an anode, a cathode and at least one layer which comprises at least one compound of the formula (1) indicated above. Preferred electronic devices here are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) or organic laser diodes (O-lasers), comprising, in at least one layer, at least one compound of the formula (1) indicated above. Particular preference is given to organic electroluminescent devices. Active components are generally the organic or inorganic materials, which are introduced between the anode and cathode, for example charge-injection, charge-transport or charge-blocking materials, but in particular emission materials and matrix materials. The compounds according to the invention exhibit particularly good properties as emission material in organic electroluminescent devices. Organic electroluminescent devices are therefore a preferred embodiment of the invention.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, charge-generation layers and/or organic or inorganic p/n junctions. It is likewise possible for interlayers, which have, for example, an exciton-blocking function and/or control the charge balance in the electroluminescent device, to be introduced between two emitting layers. However, it should be pointed out that each of these layers does not necessarily have to be present. The organic electroluminescent device may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to three-layer systems, where the three layers exhibit blue, green and orange or red emission (for the basic structure see, for example, WO 2005/011013), or systems which comprise more than three emitting layers.

In a preferred embodiment of the invention, the organic electroluminescent device comprises the compound of the formula (1) or the preferred embodiments mentioned above as emitting compound in one or more emitting layers.

If the compound of the formula (1) is employed as emitting compound in an emitting layer, it is preferably employed in combination with one or more matrix materials. The mixture of the compound of the formula (1) and the matrix material comprises between 1 and 99% by weight, preferably between 2 and 40% by weight, particularly preferably between 3 and 30% by weight, in particular between 5 and 25% by weight, of the compound of the formula (1), based on the entire mixture comprising emitter and matrix material. Correspondingly, the mixture comprises between 99 and 1% by weight, preferably between 98 and 60% by weight, particularly preferably between 97 and 70% by weight, in particular between 95 and 75% by weight, of the matrix material, based on the entire mixture comprising emitter and matrix material.

Suitable matrix materials for the compounds according to the invention are ketones, phosphine oxides, sulfoxides and sulfones, for example in accordance with WO 2004/013080, WO 2004/093207, WO 2006/005627 or WO 2010/006680, triarylamines, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 07/063754 or WO 08/056746, indenocarbazole derivatives, for example in accordance with the unpublished applications DE 102009023155.2 and DE 102009031021.5, azacarbazoles, for example in accordance with EP 1617710, EP 1617711, EP 1731584, JP 2005/347160, bipolar matrix materials, for example in accordance with WO 07/137725, silanes, for example in accordance with WO 2005/111172, azaboroles or boronic esters, for example in accordance with WO 06/117052, triazine derivatives, for example in accordance with WO 2010/015306, WO 2007/063754 or WO 2008/056746, zinc complexes, for example in accordance with EP 652273 or in accordance with WO 2009/062578, diaza- or tetraazasilole derivatives, for example in accordance with WO 2010/054729, diazaphosphole derivatives, for example in accordance with WO 2010/054730, or dibenzofuran derivatives, for example in accordance with WO 2009/148015.

It may also be preferred to employ a plurality of different matrix materials as a mixture, in particular at least one electron-conducting matrix material and at least one hole-conducting matrix material. A preferred combination is, for example, the use of an aromatic ketone, an aromatic phosphine oxide or a triazine with a triarylamine derivative or a carbazole derivative as mixed matrix for the metal complex according to the invention. Preference is likewise also given to mixtures of a hole- or electron-transporting material with a material which is involved in neither hole transport nor electron transport, as disclosed, for example, in the unpublished application DE 102009014513.3.

The cathode preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys of an alkali or alkaline-earth metal and silver, for example an alloy of magnesium and silver. In the case of multilayered structures, further metals which have a relatively high work function, such as, for example, Ag, may also be used in addition to the said metals, in which case combinations of the metals, such as, for example, Mg/Ag, Ca/Ag or Ba/Ag, are generally used. It may also be preferred to introduce a thin interlayer of a material having a high dielectric constant between a metallic cathode and the organic semiconductor. Suitable for this purpose are, for example, alkali metal or alkaline-earth metal fluorides, but also the corresponding oxides or carbonates (for example LiF, $Li_2O$, $BaF_2$, MgO, NaF, CsF, $Cs_2CO_3$, etc.). The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. For some applications, at least one of the electrodes must be transparent or partially transparent in order to enable either irradiation of the organic material (O-SCs) or the coupling-out of light (OLEDs/PLEDs, O-LASERs). Preferred anode materials for transparent or partially transparent anodes are conductive mixed metal oxides. Particular preference is given to indium tin oxide (ITO) or indium zinc oxide (IZO). Preference is furthermore given to conductive doped organic materials, in particular conductive doped polymers.

In general, all materials as used for the layers in accordance with the prior art can be used in the further layers, and the person skilled in the art will be able to combine each of these materials with the materials according to the invention in an electronic device without inventive step.

The device is correspondingly (depending on the application) structured, provided with contacts and finally hermetically sealed, since the lifetime of devices of this type is drastically shortened in the presence of water and/or air.

Preference is furthermore given to an organic electroluminescent device, characterised in that one or more layers are applied by means of a sublimation process, in which the materials are vapour-deposited in vacuum sublimation units at an initial pressure of usually less than $10^{-5}$ mbar, preferably less than $10^{-6}$ mbar. It is also possible for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing, LITI (light induced thermal imaging, thermal transfer printing), ink-jet printing or nozzle printing. Since the compounds of the formula (1) according to the invention have very good solubility in organic solvents, they are particularly suitable for processing from solution. The compounds according to the invention are therefore preferably processed from solution.

The organic electroluminescent device can also be produced as a hybrid system by applying one or more layers from solution and applying one or more other layers by vapour deposition. Thus, for example, it is possible to apply an emitting layer comprising a compound of the formula (1) and a matrix material from solution and to apply a hole-blocking layer and/or an electron-transport layer on top by vacuum vapour deposition.

These processes are generally known to the person skilled in the art and can be applied by him without problems to organic electroluminescent devices comprising compounds of the formula (1) or the preferred embodiments mentioned above.

For processing from solution, solutions or formulations of the compounds of the formula (1) are necessary. It may be preferred here to use mixtures of two or more solvents. Suitable and preferred solvents are, for example, toluene, anisole, o-, m- or p-xylene, methyl benzoate, dimethylanisole, mesitylene, tetralin, veratrol, THF, methyl-THF, THP, chlorobenzene, dioxane or mixtures of these solvents.

The present invention therefore furthermore relates to a solution or formulation comprising at least one compound of the formula (1) and one or more solvents, in particular organic solvents. The way in which solutions of this type can be prepared is known to the person skilled in the art and is described, for example, in WO 2002/072714, WO 2003/019694 and the literature cited therein.

The electronic devices according to the invention, in particular organic electroluminescent devices, are distinguished by the following surprising advantages over the prior art:

1. The compounds of the formula (1) have very good solubility in a multiplicity of common organic solvents and are therefore very highly suitable for processing from solution. In particular, the compounds according to the invention have higher solubility than the related compounds described in the prior art.
2. Organic electroluminescent devices comprising compounds of the formula (1) as emitting materials have an excellent lifetime. In particular, the lifetime is better than in the case of related compounds in accordance with the prior art.
3. Organic electroluminescent devices comprising compounds of the formula (1) as emitting materials have excellent efficiency. In particular, the efficiency is better than in the case of related compounds in accordance with the prior art.

These above-mentioned advantages are not accompanied by an impairment in the other electronic properties.

The invention is explained in greater detail by the following examples without wishing to restrict it thereby. The person skilled in the art will be able to use the descriptions to produce further electronic devices according to the invention without inventive step and thus to carry out the invention throughout the range disclosed.

EXAMPLES

The following syntheses are carried out, unless indicated otherwise, under a protective-gas atmosphere in dried solvents. Starting materials 1, 2, 10 and 11 and the solvents can be purchased commercially, for example from ALDRICH. Compound 4, compound 15 and compound 17 can be prepared in accordance with WO 2002/068435 or analogously to the process described in WO 2002/068435. Compound 7 can be prepared analogously to J. Mater. Chem. 2007, 17, 3714-3719.

Example 1

Synthesis of Compound 6

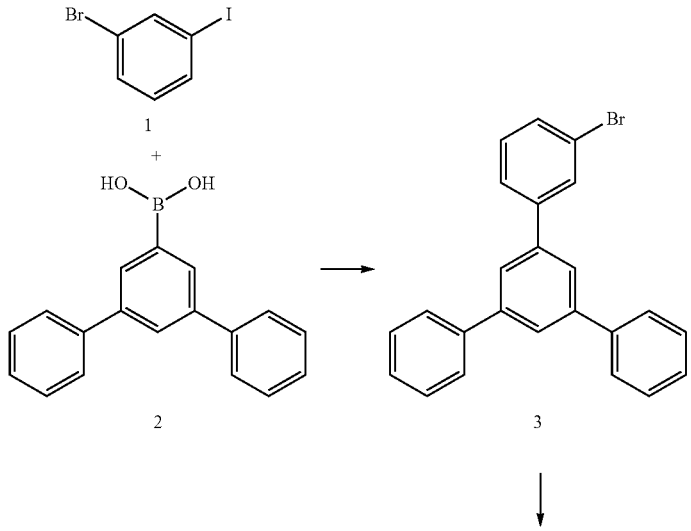

-continued

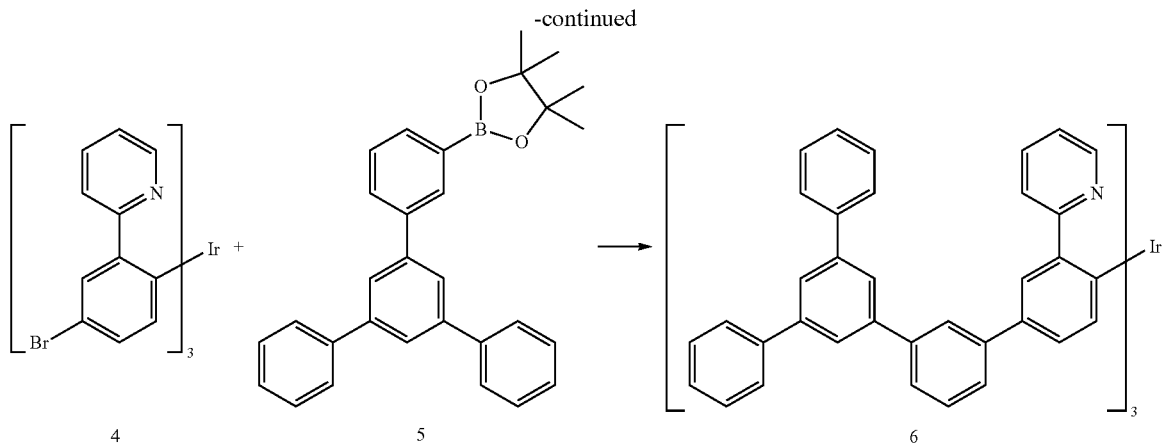

a) Synthesis of 1-bromo-3-([3,1';5,1"]terphen-1-yl)benzene (compound 3)

40.0 g (146 mmol) of [3,1';5,1"]terphenyl-3-boronic acid (2), 18.8 g (146 mmol) of 1-iodo-3-bromobenzene (1) and 109.3 g (730 mmol) of potassium carbonate are suspended in 1350 ml of toluene and 1150 ml of water. 844 mg (0.73 mmol) of tetrakis(triphenylphosphine)palladium(0) are added to this suspension, and the reaction mixture is heated under reflux for 16 h. After cooling, the organic phase is separated off, washed three times with 200 ml of water, dried using sodium sulfate and subsequently evaporated to dryness. The residue is washed with ethanol and recrystallised from ethyl acetate and finally dried under reduced pressure. The yield is 47.6 g (123 mmol), corresponding to 84.5% of theory.

b) Synthesis of 3-([3,1';5,1"]terphen-1-yl)phenyl 1-pinacolylboronate (compound 5)

40.0 g (104 mmol) of 1-bromo-3-([3,1';5,1"]terphen-1-yl)benzene (3), 29.0 g (114 mmol) of bispinacolatodiboron, 29.5 g (301 mmol) of potassium acetate are suspended in 800 ml of dimethyl sulfoxide. 4.24 g (5.2 mmol) of 1,1-bis(diphenylphosphino)ferrocenepalladium(II) dichloride* DCM are added to this suspension, and the reaction mixture is heated under reflux for 16 h. After cooling, 600 ml of ethyl acetate and 400 ml of water are added, and the organic phase is separated off, washed three times with 200 ml of water, dried using sodium sulfate and subsequently evaporated to dryness. The crude product is recrystallised from heptane and finally dried under reduced pressure. The yield is 34.5 g (80 mmol), corresponding to 46.1% of theory.

c) Synthesis of fac-tris[2-(2-pyridinyl-κN)(5-(3-([3,1';5,1"]terphen-1-yl)phenyl)phenyl)κC]iridium(III) (compound 6)

1.7 g (2.0 mmol) of fac-tris[2-(2-pyridinyl-κN)(5-bromophenyl)κC]iridium(III) (4), 7.42 g (17 mmol) of 3-([3,1';5,1"]terphen-1-yl)phenyl 1-pinacolylboronate (5), 2.51 g (12 mmol) of potassium phosphate are suspended in 100 ml of toluene, 100 ml of dioxane and 111 ml of water. 4 mg (0.1 mmol) of palladium(II) acetate and 35 mg (0.2 mmol) of tri-o-tolylphosphine are added to this suspension, and the reaction mixture is heated under reflux for 24 h. After cooling, the organic phase is separated off, washed three times with 200 ml of water, filtered through silica gel, dried using sodium sulfate and subsequently evaporated to dryness. The residue is recrystallised from dioxane/ethanol and finally dried under reduced pressure. The yield is 2.42 g (1.6 mmol), corresponding to 80.9% of theory.

Example 2

Synthesis of Compound 9

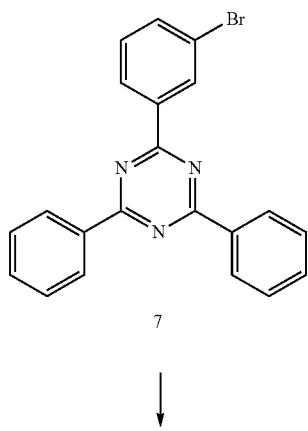

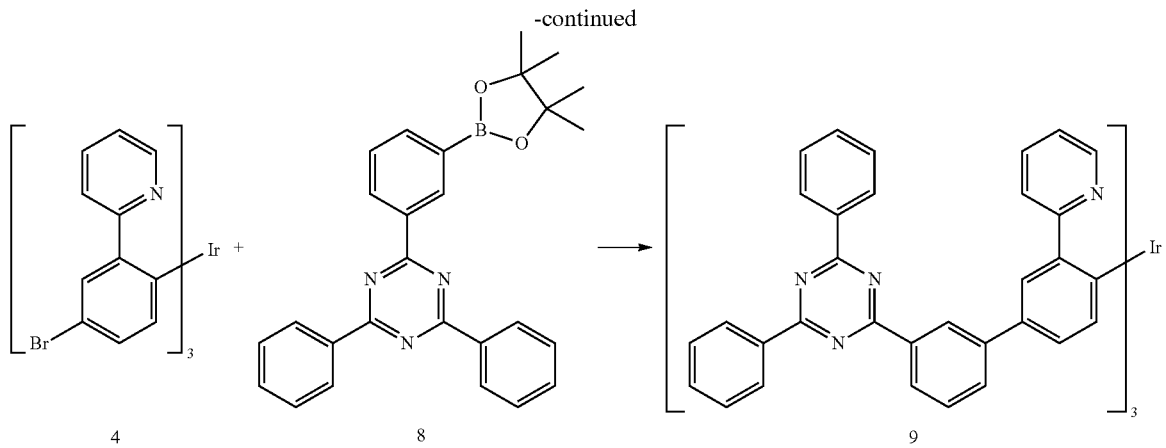

a) Synthesis of 2-(3-pinacolylboronatophenyl)-4,6-diphenyl-1,3,5-triazine (compound 8)

The synthesis is carried out analogously to that of compound 5. The yield is 31.9 g (73 mmol), corresponding to 81.3% of theory.

b) Synthesis of fac-tris[2-(2-pyridinyl-κN)(5-(3-phenyl(4,6-diphenyl-1,3,5-triazinyl)phenyl)κC]iridium (III) (compound 9)

The synthesis is carried out analogously to that of compound 6. The yield is 1.5 g (0.95 mmol), corresponding to 55.6% of theory.

Example 3

Synthesis of Compound 14

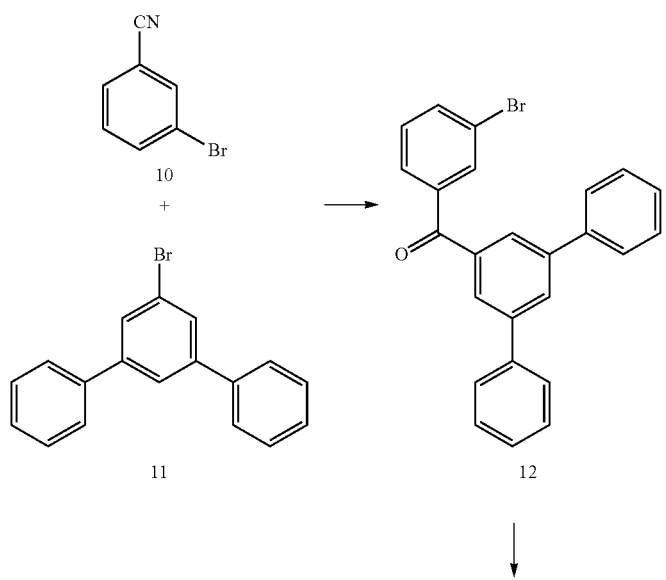

-continued

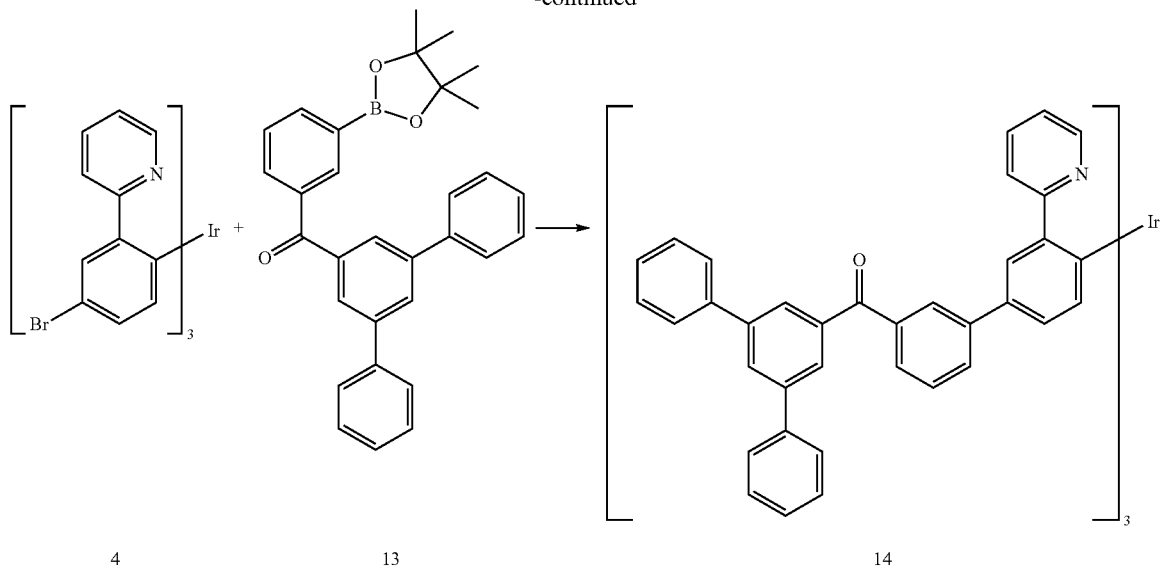

| 4 | 13 | 14 | a) Synthesis of (3-bromophenyl)-[1,1';3',1"]terphenyl-5'-ylmethanone (compound 12)

A solution of 20.0 g (64.7 mmol) of 3-bromo-[3,1';5,1"]terphenyl in 300 ml of tetrahydrofuran is slowly added dropwise to 1.7 g (71.2 mmol) of magnesium turnings, and the mixture is heated under reflux for 3 h. The solution is then cooled to −40° C., and a solution of 11.8 g (65 mmol) of 3-bromobenzonitrile in 100 ml of tetrahydrofuran is added dropwise. After the addition, the solution is heated under reflux for 6 h. After cooling, 600 ml of ethyl acetate and 400 ml of water are added, and the organic phase is separated off, washed three times with 200 ml of water, dried using sodium sulfate and subsequently evaporated to dryness. The residue is recrystallised from ethanol and subsequently dried under reduced pressure. The yield is 21.7 g (53 mmol), corresponding to 81.3% of theory.

b) Synthesis of 3-pinacolylboronatophenyl-[1,1';3',1"]terphenyl-5'-ylmethanone (compound 13)

The synthesis is carried out analogously to that of compound 5. The yield is 15.7 g (34 mmol), corresponding to 76.2% of theory.

c) Synthesis of fac-tris[2-(2-pyridinyl-κN)(5-(3-phenyl-3-[1,1';3',1"]terphenyl-5'-ylmethanone-κC]iridium(III) (compound 14)

The synthesis is carried out analogously to that of compound 6. The yield is 1.7 g (1.03 mmol), corresponding to 57.3% of theory.

Example 4

Synthesis of fac-tris[2-(1-isoquinolinyl-κN)(5-(3-([3,1';5,1"]-terphen-1-yl)phenyl)phenyl)κC]iridium(III) (compound 16)

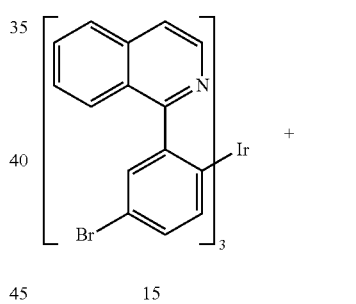

15

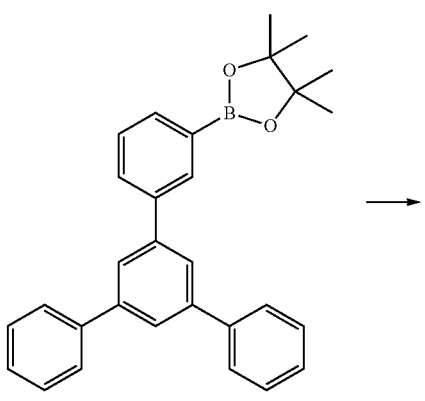

5

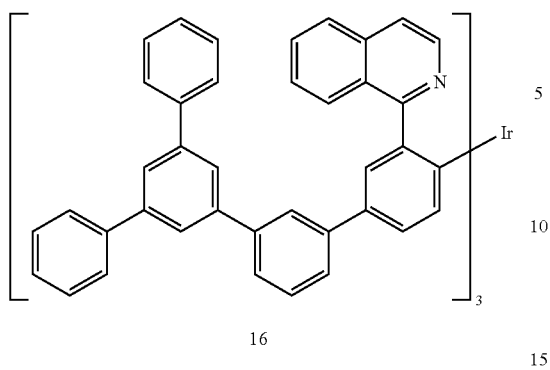

16

The synthesis is carried out analogously to the synthesis of compound 6. The yield is 6.52 g (3.8 mmol), corresponding to 65.6% of theory.

Example 5

Synthesis of fac-tris[2-(2-quinolinyl-κN)(5-(3-([3,1'; 5,1"]-terphen-1-yl)phenyl)phenyl)κC]iridium(III) (compound 18)

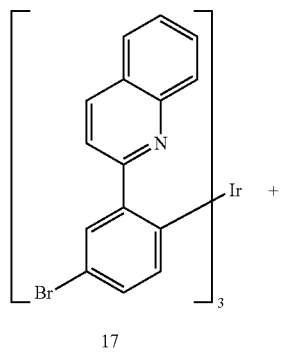

17

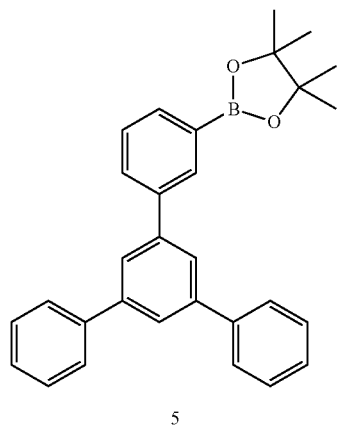

5

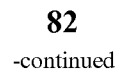

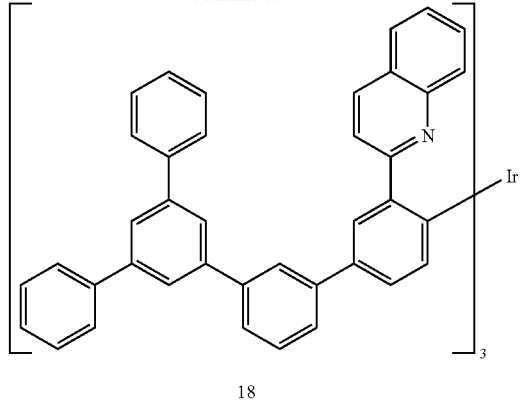

18

The synthesis is carried out analogously to the synthesis of compound 6. The yield is 3.46 g (2.0 mmol), corresponding to 69.2% of theory.

Example 4

Production And Characterisation of Organic Electroluminescent Devices Comprising the Compounds According To the Invention The structures of TEG-1, TER-1, TER-3 (synthesised in accordance with WO 2004/085449), TMM-1 (synthesised in accordance with WO 2010/015306) and TMM-2 (synthesised in accordance with WO 2009/124627) and the compounds TEG-2 to TEG-4, TER-2 and TER-4 according to the invention are depicted below for clarity.

Structures of the Emitters

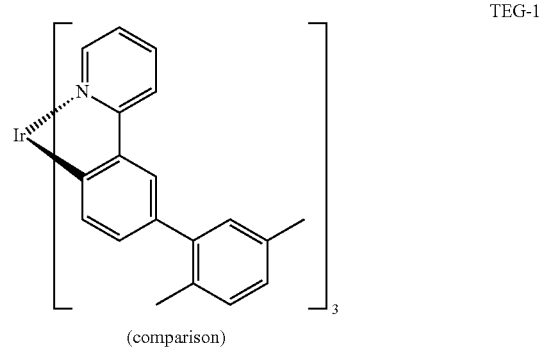

(comparison)

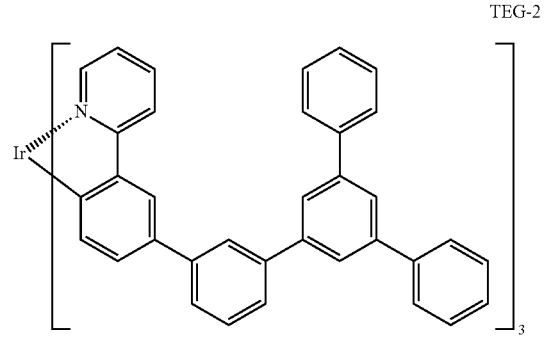

TEG-3
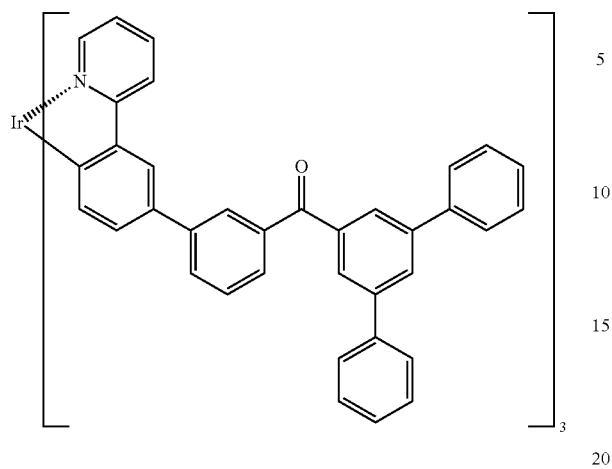
TEG-4
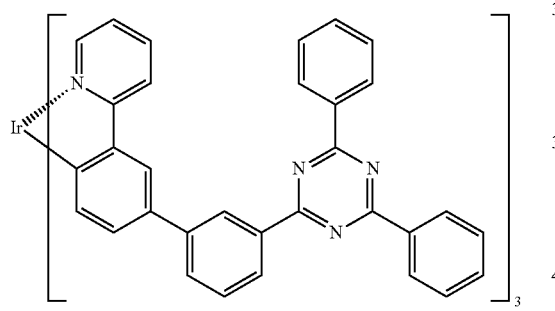
TER-1
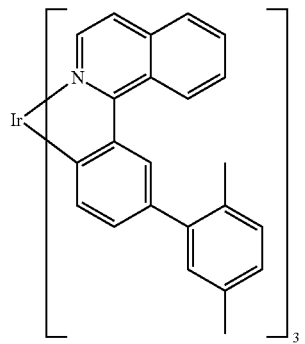
TER-2
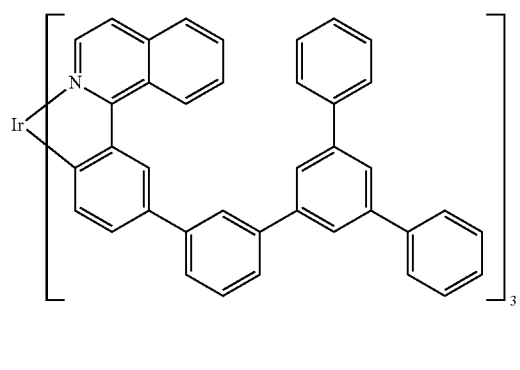
TER-3
TER-4
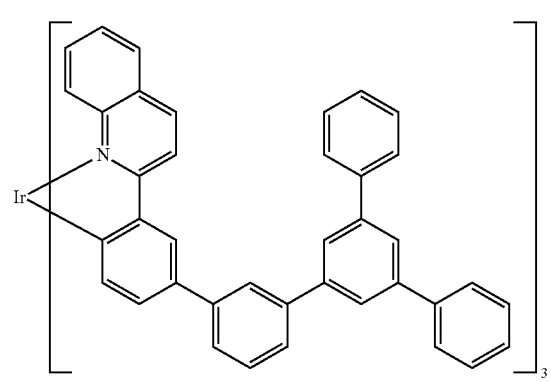

Structures of the Matrices

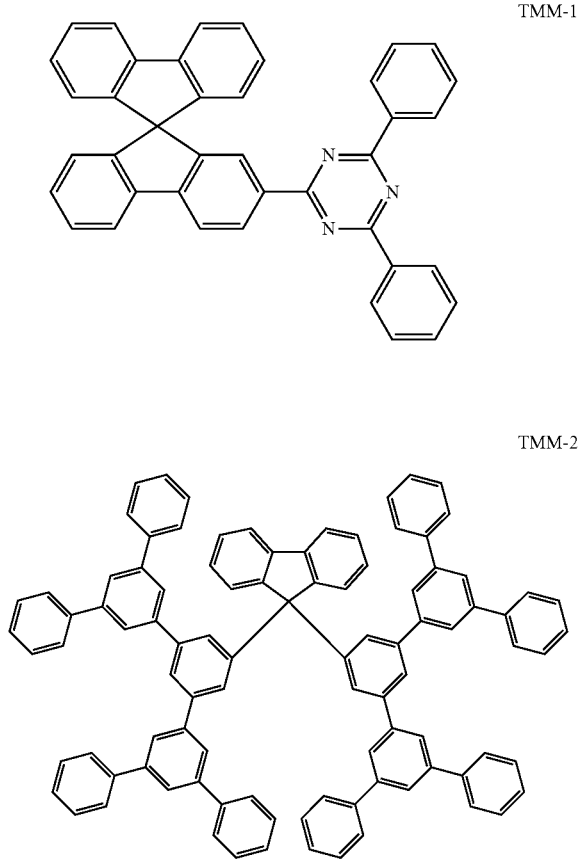

Materials according to the invention can be used from solution, where they result in significantly simpler devices which nevertheless have good properties. The production of such components is based on the production of polymeric light-emitting diodes (PLEDs), which has already been described many times in the literature (for example in WO 2004/037887). In the present case, the compounds according to the invention or likewise soluble comparative compounds (TEG-1, TER-1 and TER-3) are dissolved in toluene. The typical solids content of such solutions is between 16 and 25 g/l if, as here, the layer thickness of 80 nm which is typical for a device is to be achieved by means of spin coating. FIG. 1 shows the typical structure of a device of this type, where the composition 48% by weight of TMM-1, 48% by weight of TMM-2 and 4% by weight of TER is used for a red-emitting device. Structured ITO substrates and the material for the so-called buffer layer (PEDOT, actually PEDOT:PSS) are commercially available (ITO from Technoprint and others, PEDOT:PSS as Clevios Baytron P aqueous dispersion from H.C. Starck). The interlayer used serves for hole injection; in this case, HIL-012 from Merck was used. The emission layer is applied by spin coating in an inert-gas atmosphere, in the present case argon, and dried by heating at 120° C. for 10 min. Finally, a barium and aluminium cathode is applied by vacuum vapour deposition. A hole-blocking layer and/or an electron-transport layer can also be applied between the emitting layer and the cathode by vapour deposition, and the interlayer can also be replaced by one or more layers, which merely have to satisfy the condition of not being detached again by the subsequent processing step of deposition of the emitting layer from solution.

The devices are characterised by standard methods, and the OLED examples mentioned have not yet been optimised. Table 1 summarises the data obtained. In the case of the processed devices, it is apparent here that the materials according to the invention are superior in efficiency and/or lifetime to those previously available.

TABLE 1

Results with solution-processed materials in the device configuration of FIG. 1 and of the above-mentioned composition for red-emitting devices

| Ex. | EML 80 nm | Max. eff. [cd/A] | Voltage [V] at 100 cd/m$^2$ | CIE (x, y) | Lifetime [h], initial brightness 1000 cd/m$^2$ |
|---|---|---|---|---|---|
| 5 comp. | TMM-1:TMM-2:TEG-1 | 23 | 3.6 | 0.33/0.63 | 17000 |
| 6 | TMM-1:TMM-2:TEG-2 | 29 | 3.7 | 0.33/0.63 | 38000 |
| 7 | TMM-1:TMM-2:TEG-3 | 27 | 4.2 | 0.32/0.63 | 21000 |
| 8 | TMM-1:TMM-2:TEG-4 | 30 | 4.3 | 0.33/0.63 | 32000 |
| 9 comp. | TMM-1:TMM-2:TER-1 | 6 | 5.9 | 0.34/0.62 | 5000 |
| 10 | TMM-1:TMM-2:TER-2 | 8 | 5.2 | 0.34/0.62 | 12000 |
| 11 comp. | TMM-1:TMM-2:TER-3 | 8 | 5.8 | 0.34/0.62 | 6000 |
| 12 | TMM-1:TMM-2:TER-4 | 9 | 5.2 | 0.34/0.62 | 15000 |

The invention claimed is:

1. A compound of the formula (1)

 formula (1)

where the compound contains a moiety $M(L)_n$ of the formula (2) or formula (3):

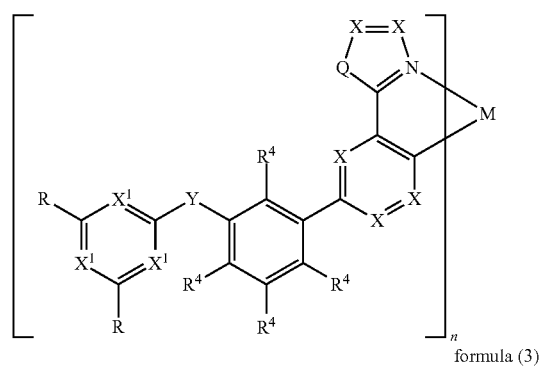

formula (2)

formula (3)

where the following applies to the symbols and indices used:

M is a metal selected from the group consisting of iridium, rhodium, platinum and palladium;

X and $X^1$ are, identically or differently on each occurrence, $CR^1$ or N;

Q is, identically or differently on each occurrence, $R^1C=CR^1$, $R^1C=N$, O, S, Se or $NR^1$;

V is, identically or differently on each occurrence, O, S, Se or $NR^1$;

Y is, identically or differently on each occurrence, a single bond or a divalent group selected from $C(R^1)_2$, $C(=O)$, O, S, SO, $SO_2$, $NR^1$, $PR^1$ or $P(=O)R^1$;

R is selected from the groups of the following formulae (8) to (24):

formula (8)

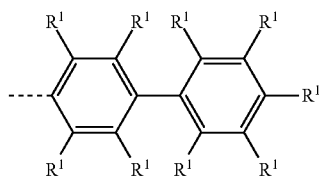

formula (9)

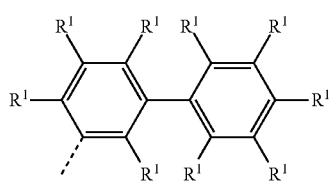

formula (10)

formula (11)

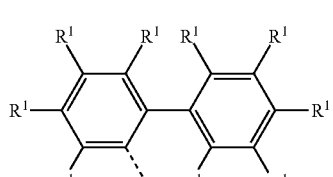

formula (12)

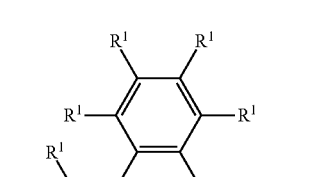

formula (13)

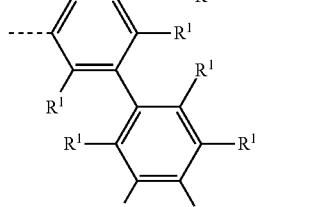

formula (14)

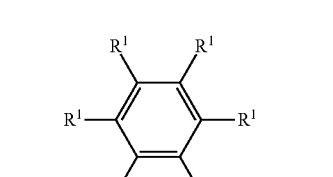

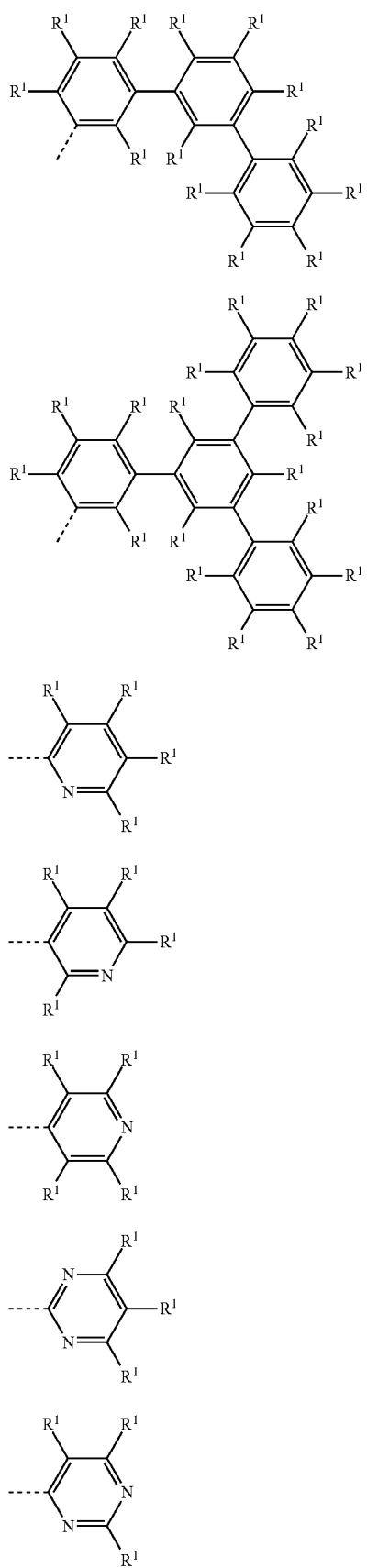

formula (15)

formula (16)

formula (17)

formula (18)

formula (19)

formula (20)

formula (21)

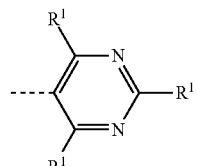

formula (22)

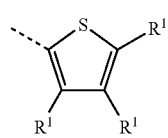

formula (23)

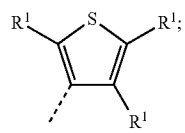

formula (24)

R¹ is, identically or differently on each occurrence, H, D, F, Cl, Br, I, N(R²)₂, CN, NO₂, Si(R²)₃, B(OR²)₂, C(=O)R², P(=O)(R²)₂, S(=O)R², S(=O)₂R², OSO₂R², a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which is optionally substituted by one or more radicals R², where one or more non-adjacent CH₂ groups is optionally replaced by R²C=CR², C≡C, Si(R²)₂, Ge(R²)₂, Sn(R²)₂, C=O, C=S, C=Se, C=NR², P(=O)(R²), SO, SO₂, NR², O, S or CONR² and where one or more H atoms is optionally replaced by D, F, Cl, Br, I, CN or NO₂, or an aryloxy or heteroaryloxy group having 5 to 60 aromatic ring atoms, which is optionally substituted by one or more radicals R², or a diarylamino group, diheteroarylamino group or arylheteroarylamino group having 10 to 40 aromatic ring atoms, which is optionally substituted by one or more radicals R², or a combination of two or more of these groups;

R² is, identically or differently on each occurrence, H, D, F, Cl, Br, I, N(R³)₂, CN, NO₂, Si(R³)₃, B(OR³)₂, C(=O)R³, P(=O)(R³)₂, S(=O)R³, S(=O)₂R³, OSO₂R³, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which is optionally substituted by one or more radicals R³, where one or more non-adjacent CH₂ groups is optionally replaced by R³C=CR³, C≡C, Si(R³)₂, Ge(R³)₂, Sn(R³)₂, C=O, C=S, C=Se, C=NR³, P(=O)(R³), SO, SO₂, NR³, O, S or CONR³ and where one or more H atoms is optionally replaced by D, F, Cl, Br, I, CN or NO₂, or an aromatic or heteroaromatic ring system having 5 to 60 aromatic ring atoms, each of which is optionally substituted by one or more radicals R³, or an aryloxy or heteroaryloxy group having 5 to 60 aromatic ring atoms, which is optionally substituted by one or more radicals R³, or a diarylamino group, diheteroarylamino group or arylheteroarylamino group having 10 to 40 aromatic ring atoms, which is optionally substituted by one or more radicals R³, or a combination of two or more of these groups; or two or more adjacent radicals R² optionally form a mono- or polycyclic, aliphatic or aromatic ring system with one another;

R³ is, identically or differently on each occurrence, H, D, F or an aliphatic, aromatic and/or heteroaromatic hydrocarbon radical having 1 to 20 C atoms, in which, in addition, one or more H atoms is optionally replaced by F; two or more substituents R³ here optionally form a mono- or polycyclic, aliphatic or aromatic ring system with one another;

R⁴ is, identically or differently on each occurrence, H or D;

L' is, identically or differently on each occurrence, a co-ligand;

n is 1, 2 or 3 when M is iridium or rhodium and is 1 or 2 when M is platinum or palladium;

m is 0, 1, 2, 3 or 4; and optionally a plurality of ligands L linked to one another or linked to L' via bridge Z to form a tridentate, tetradentate, pentadentate or hexadentate ligand system.

2. The compound according to claim 1, wherein the symbol X stands, identically or differently on each occurrence, for CR¹.

3. The compound according to claim 1, wherein all symbols X1 stand, identically or differently on each occurrence, for CR1 or in that all symbols X1 stand for N.

4. The compound according to claim 1, wherein the symbol Y stands, identically or differently on each occurrence, for a single bond or a divalent group selected from C(=O) or NR1.

5. The compound according to claim 1, wherein the symbol Y stands, identically or differently on each occurrence, for a single bond.

6. The compound according to claim 1, wherein

M is iridium or platinum;

X is, identically or differently on each occurrence, CR¹;

X¹ is selected so that all symbols X¹ stand, identically or differently on each occurrence, for CR¹ or in that all symbols X¹ stand for N;

Q is, identically or differently on each occurrence, R¹C=CR¹ or R¹C=N;

V is, identically or differently on each occurrence, O, S or NR¹;

Y is, identically or differently on each occurrence, a single bond or a divalent group selected from C(=O) or NR¹; and R⁴ is H.

7. The compound according to claim 1, wherein

M is iridium;

X is, identically or differently on each occurrence, CR¹;

X¹ is selected so that all symbols X¹ stand, identically or differently on each occurrence, for CR¹ or in that all symbols X¹ stand for N;

Q is, identically or differently on each occurrence, R¹C=CR¹;

V is, identically or differently on each occurrence, S;

Y is, identically or differently on each occurrence, a single bond; and

R⁴ is H.

8. The compound according to claim 1, wherein the moieties of the formula (2) or (3) are selected from the moieties of the following formulae (4), (5), (6) and (7):

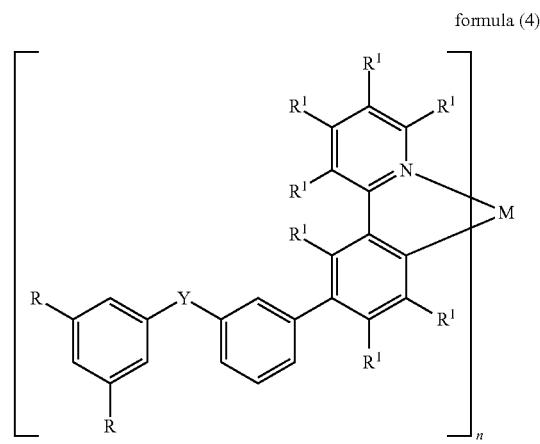

formula (4)

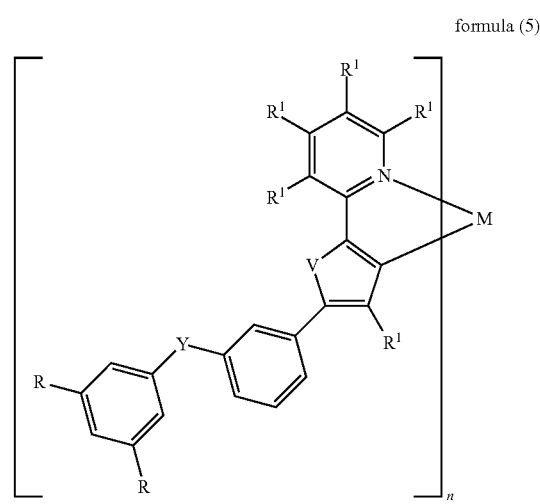

formula (5)

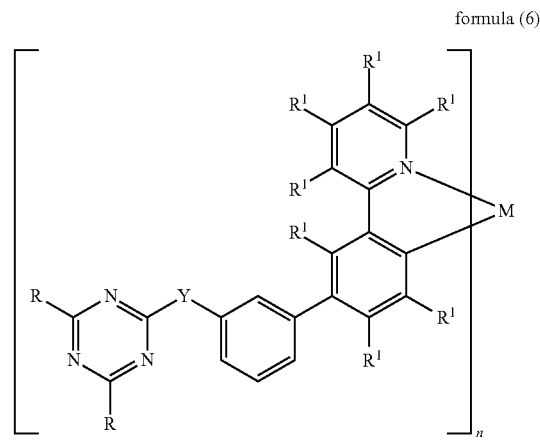

formula (6)

-continued formula (7)

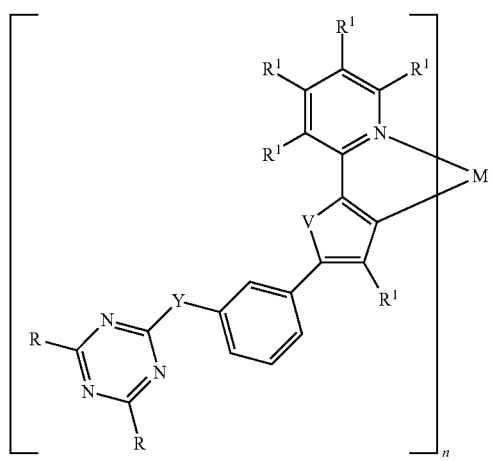

other symbols used have the meanings given in claim 1.

9. The compound according to claim 1, wherein the symbol R stands, identically or differently on each occurrence, for a straight-chain alkyl group having 1 to 10 C atoms or for a branched or cyclic alkyl group having 3 to 10 C atoms, each of which is optionally substituted by one or more radicals $R^1$, and where one or more non-adjacent $CH_2$ groups is optionally replaced by O and where one or more H atoms is optionally replaced by D, F or CN, or an aromatic or heteroaromatic ring system having 5 to 30 aromatic ring atoms, which optionally in each case is substituted by one or more radicals $R^1$.

10. The compound according to claim 1, wherein the symbol R stands, identically or differently on each occurrence, for a straight-chain alkyl group having 1 to 10 C atoms or for a branched or cyclic alkyl group having 3 to 10 C atoms, each of which is optionally substituted by one or more radicals $R^1$, and where one or more non-adjacent $CH_2$ groups is optionally replaced by O and where one or more H atoms is optionally replaced by D, F or CN, or an aromatic or heteroaromatic ring system having 5 to 20 aromatic ring atoms, which optionally in each case is substituted by one or more radicals $R^1$.

11. The compound according to claim 1, wherein the compound is of the formulae (25) to (28):

formula (25)

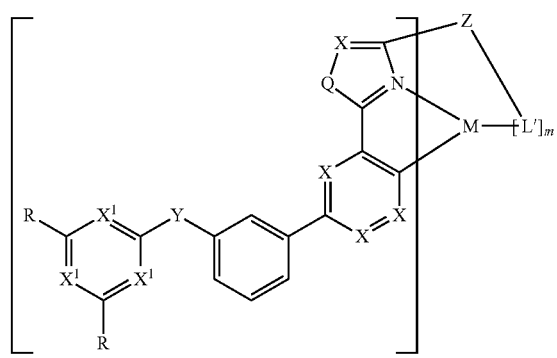

-continued formula (26)

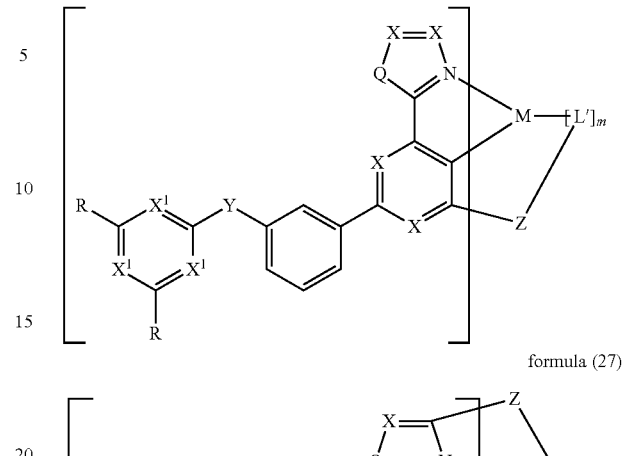

formula (27)

formula (28)

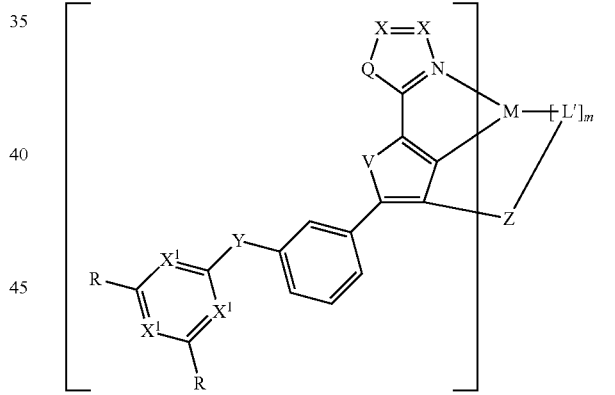

where the symbols used have the meanings given in claim 1, and Z represents a bridging unit containing 1 to 80 atoms from the third, fourth, fifth and/or sixth main group (IUPAC group 13, 14, 15 or 16) or a 3- to 6-membered homo- or heterocycle which covalently bonds the part-ligands L to one another or L to L'.

12. The compound according to claim 1, wherein the ligand L' is selected from the group consisting of carbon monoxide, nitrogen monoxide, alkyl cyanides, aryl cyanides, alkyl isocyanides, aryl isocyanides, amines, phosphines, phosphites, arsines, stibines, nitrogen-containing heterocycles, carbenes, hydride, deuteride, the halides $F^-$, $Cl^-$, $Br^-$ and $I^-$, alkylacetylides, arylacetylides, cyanide, cyanate, isocyanate, thiocyanate, isothiocyanate, aliphatic or aromatic alcoholates, aliphatic or aromatic thioalcoholates, amides, carboxylates, aryl groups, $O^{2-}$, $S^{2-}$, carbides, nitrenes, $N^{3-}$, diamines, imines, diimines, heterocycles containing two nitrogen atoms, diphosphines, 1,3-diketonates derived from 1,3-diketones, 3-ketonates derived from 3-ketoesters, carboxylates derived from aminocarboxylic acids, salicyliminates derived from salicylimines, dialcoholates derived from dialcohols, borates of nitrogen-containing heterocycles; or selected from bidentate ligands which are composed of the combination of two groups of the following formulae (42) to (69), where one group is bonded via a neutral nitrogen atom or a carbene atom and the other group is bonded via a negatively charged carbon atom or a negatively charged nitrogen atom, and the ligand L' is formed from the groups of the formulae (42) to (69) by these groups bonding to one another, in each case at the position denoted by #,

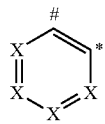

formula (42)

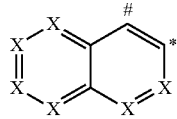

formula (43)

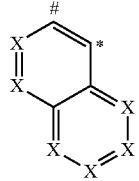

formula (44)

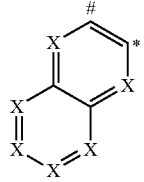

formula (45)

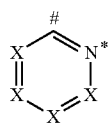

formula (46)

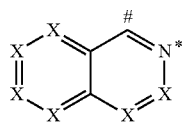

formula (47)

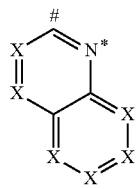

formula (48)

-continued

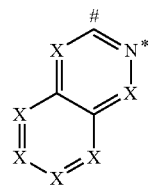

formula (49)

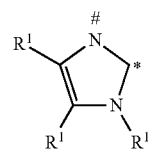

formula (50)

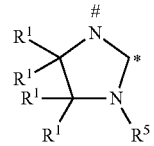

formula (51)

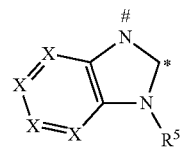

formula (52)

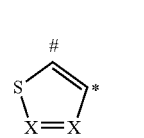

formula (53)

formula (54)

formula (55)

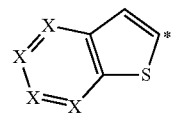

formula (56)

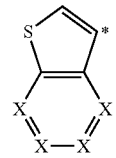

formula (57)

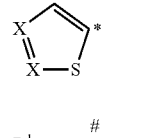

formula (58)

-continued

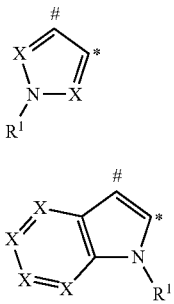
formula (59)

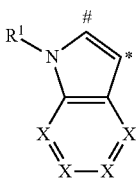
formula (60)

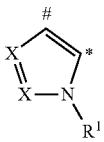
formula (61)

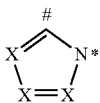
formula (62)

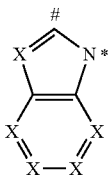
formula (63)

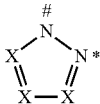
formula (64)

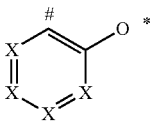
formula (65)

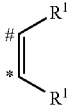
formula (66)

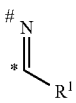
formula (67)

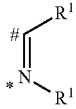
formula (68)

formula (69)

where * indicates the position of the coordination to the metal, and the symbols used have the meanings described in claim 1;

or selected from $\eta^5$-cyclopentadienyl, $\eta^5$-pentamethylcyclopentadienyl, $\eta^6$-benzene or $\eta^7$-cycloheptatrienyl, each of which is optionally substituted by one or more radicals $R^1$;

or selected from 1,3,5-cis-cyclohexane derivatives, 1,1,1-tri(methylene)-methane derivatives or 1,1,1-trisubstituted methanes.

13. The compound according to claim 1, wherein the ligand L' is selected from the group consisting of halophosphines, trialkylphosphines, triarylphosphines or alkylarylphosphines.

14. A process for the preparation of the compound according to claim 1 which comprises reacting the corresponding free ligands with metal alkoxides of the formula (74), with metal ketoketonates of the formula (75), with metal halides of the formula (76) or with dimeric metal complexes of the formula (77):

$$M(OR^1)_n$$ formula (74)

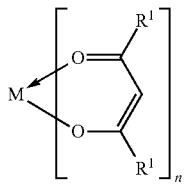 formula (75)

$$MHal_n$$ formula (76)

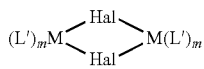 formula (77)

where the symbols M, m, n and $R^1$ have the meanings indicated in claim 1, and Hal=F, Cl, Br or I.

15. An electronic device comprising at least one compound according to claim 1.

16. The electronic device as claimed in claim 15, wherein the device is selected from the group consisting of an organic electroluminescent device (OLED, PLED), an organic integrated circuit (O-IC), an organic field-effect transistor (O-FET), an organic thin-film transistor (O-TFT), an organic light-emitting transistor (O-LET), an organic solar cell (O-SC), an organic optical detector, an organic photoreceptor, an organic field-quench device (O-FQD), a light-emitting electrochemical cell (LEC) and an organic laser diode (O-laser).

17. An organic electroluminescent device comprising a compound according to claim 1 as an emitting compound in one or more emitting layers in combination with a matrix material.

18. The organic electroluminescent device as claimed in claim 17, wherein the matrix material is selected from the group consisting of ketone, phosphine oxide, sulfoxide, sulfone, triarylamine, carbazole derivative, indolocarbazole derivative, indenocarbazole derivative, azacarbazole derivative, bipolar matrix material, silane, azaborole, boronic ester, triazine derivative, zinc complex, diaza- or tetraazasilole derivatives, diazaphosphole derivative, dibenzofuran derivative and any one mixture of matrix materials.

19. A solution or formulation comprising at least one compound according to claim 1 and one or more solvents.

* * * * *